United States Patent [19]
Reichard et al.

[11] Patent Number: 6,063,926
[45] Date of Patent: May 16, 2000

[54] SUBSTITUTED OXIMES AS NEUROKININ ANTAGONISTS

[75] Inventors: Gregory A. Reichard, Morris Plains; Cheryl A. Alaimo, Somerset; Neng-Yang Shih, North Caldwell; Pauline C. Ting, New Providence; Nicholas I. Carruthers, North Plainfield; Brian J. Lavey, Chatham, all of N.J.

[73] Assignee: Schering Corporation, Kenilworth, N.J.

[21] Appl. No.: 09/195,429

[22] Filed: Nov. 18, 1998

[51] Int. Cl.[7] ............... C07D 401/00; C07D 211/68; C07D 211/44; C07D 211/26
[52] U.S. Cl. ............ 546/187; 546/189; 546/190; 546/194; 546/217; 546/231
[58] Field of Search .............. 546/187, 189, 546/190, 194, 217, 231

[56] References Cited

U.S. PATENT DOCUMENTS

| | | | |
|---|---|---|---|
| 5,350,852 | 9/1994 | Emonds-Alt et al. | 544/336 |
| 5,688,960 | 11/1997 | Shankar | 546/202 |
| 5,691,362 | 11/1997 | McCormick et al. | 514/339 |
| 5,696,267 | 12/1997 | Reichard et al. | 546/217 |
| 5,789,422 | 8/1998 | Reichard et al. | 514/327 |

FOREIGN PATENT DOCUMENTS

| | | |
|---|---|---|
| 630887 | 12/1994 | European Pat. Off. |
| 0 699 674 | 3/1996 | European Pat. Off. |
| 2717802 | 9/1995 | France |
| WO94/10146 | 5/1994 | WIPO |
| WO 94/29309 | 12/1994 | WIPO |
| WO95/05377 | 2/1995 | WIPO |
| WO95/12577 | 5/1995 | WIPO |
| WO 96/34857 | 11/1996 | WIPO |
| WO96/39386 | 12/1996 | WIPO |

OTHER PUBLICATIONS

Maggi et al, *Eur. J. Pharmacol.*, 166, (1989), p. 435–440.
Ellis et al, *J. Pharmacol. Exp. Ther.*, 267, 1 (1993), p. 95–101.
Chung et al, *Molecular Pharmacol.*, 48 (1995), p. 711–716.
Abstract of FR 2,717,802.

*Primary Examiner*—John Kight
*Assistant Examiner*—Raymond Covington
*Attorney, Agent, or Firm*—Anita W. Magatti

[57] ABSTRACT

Compounds within the genus represented by the structural formula I

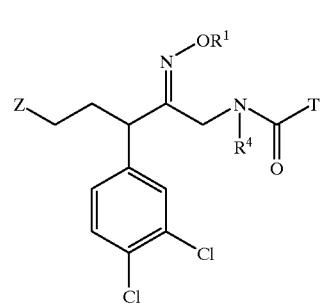

or a pharmaceutically acceptable salt thereof, wherein:

T is substituted phenyl or substituted pyridyl;

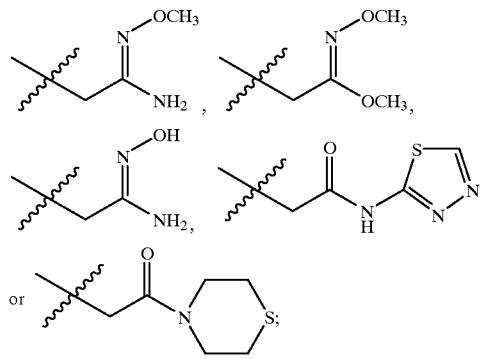

$R^4$ is methyl or ethyl; and
Z is substituted piperidinyl.

7 Claims, No Drawings

SUBSTITUTED OXIMES AS NEUROKININ ANTAGONISTS

BACKGROUND OF THE INVENTION

The present invention relates to a genus of substituted oximes useful as antagonists of tachykinin receptors, in particular as antagonists of the neuropeptides neurokinin-1 receptor ($NK_1$) and/or neurokinin-2 receptor ($NK_2$) and/or neurokinin-3 receptor ($NK_3$).

Neurokinin receptors are found in the nervous system and the circulatory system and peripheral tissues of mammals, and therefore are involved in a variety of biological processes. Neurokinin receptor antagonists are consequently expected to be useful in the treatment or prevention of various mammalian disease states, for example asthma, cough, chronic obstructive pulmonary disease (COPD), bronchospasm, emesis, neurodegenerative disease, ocular disease, inflammatory diseases such as arthritis, central nervous system conditions such as migraine and epilepsy, nociception, psychosis and various gastrointestinal disorders such as Crohn's disease.

In particular, $NK_1$ receptors have been reported to be involved in microvascular leakage and mucus secretion, and $NK_2$ receptors have been associated with smooth muscle contraction, making $NK_1$ and $NK_2$ receptor antagonists especially useful in the treatment and prevention of asthma.

Some $NK_1$ and $NK_2$ receptor antagonists have previously been disclosed: arylalkylamines were disclosed in U.S. Pat. No. 5,350,852, issued Sep. 27, 1994, and spirosubstituted azacycles were disclosed in WO 94/29309, published Dec. 22, 1994.

U.S. Pat. No. 5,696,267 discloses compounds represented by the generic structure

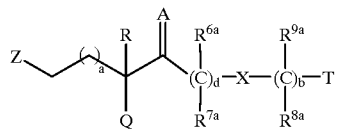

or a pharmaceutically acceptable salt thereof, wherein:

a is 0, 1, 2 or 3;
R is H, $C_{1-6}$ alkyl, —OH or $C_2$—$C_6$ hydroxyalkyl;
A is an optionally substituted oxime, hydrazone or olefin;
X is a bond, —C(O)—, —O—, —$NR^6$—, —$S(O)_e$—, —$N(R^6)C(O)$—, —$C(O)N(R^6)$— —$OC(O)NR^6$—, —OC(=S)$NR^6$—, —$N(R^6)C(=S)O$—, —C(=$NOR^1$)—, —$S(O)_2N(R^6)$—, —$N(R^6)S(O)_2$—, —$N(R^6)C(O)O$—or —OC(O)—;
b, d and e are independently 0, 1 or 2;
T is H, phthalimidyl, aryl, heterocycloalkyl, heteroaryl, cycloalkyl or bridged cycloalkyl;
Q is —$SR^6$, —$N(R^6)(R^7)$, —$OR^6$, phenyl, naphthyl or heteroaryl;
$R^{6a}$, $R^{7a}$, $R^{8a}$, $R^{9a}$, $R^6$ and $R^7$ are H, $C_{1-6}$ alkyl, $C_2$—$C_6$ hydroxyalkyl, $C_1$—$C_6$ alkoxy-$C_1$—$C_6$ alkyl, phenyl or benzyl; or $R^6$ and $R^7$, together with the nitrogen to which they are attached, form a ring;
$R^{9a}$ is $R^6$ or —$OR^6$;
Z is morpholinyl, optionally N-substituted piperazinyl, optionally

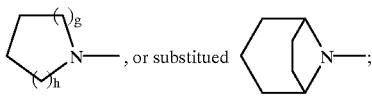

g is 0–3 and h is 1–4, provided the sum of h and g is 1–7; wherein aryl, heterocycloalkyl, heteroaryl, cycloalkyl and bridged cycloalkyl groups are optionally substituted.

We have found that certain compounds within that generic structure show surprisingly greater activity as neurokinin antagonists than those previously specifically disclosed.

SUMMARY OF THE INVENTION

Compounds of the present invention are represented by the formula I

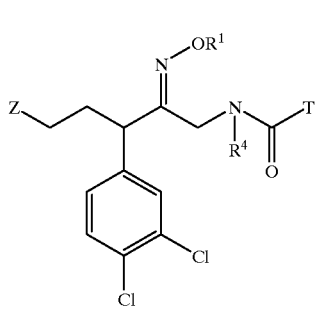

or a pharmaceutically acceptable salt thereof, wherein:

T is $R^2$-phenyl or $R^3$-pyridyl;
$R^1$ is H, methyl, ethyl, —$CH_2CN$, —$CH_2C(O)NH_2$, —$(CH_2)_3SO_3H$, —$CH_2C(O)NHCH_3$, —$CH_2C(O)NHOH$, —$CH_2C(O)NHOCH_3$, —$CH_2C(O)NHCH_2CN$, —$CH_2F$, —$CH_2C(O)NHCH_2SO_3H$,

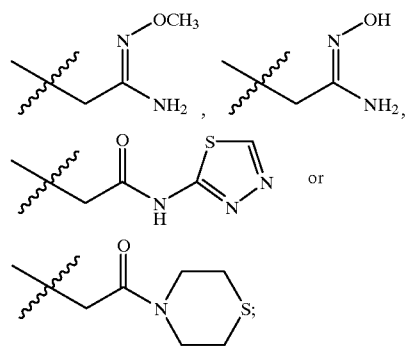

$R^2$ is 2–3 substituents independently selected from the group consisting of chloro, methyl and methoxy;
$R^3$ is 2 to 3 substituents independently selected from the group consisting of chloro and methyl;
$R^4$ is methyl or ethyl; and
Z is

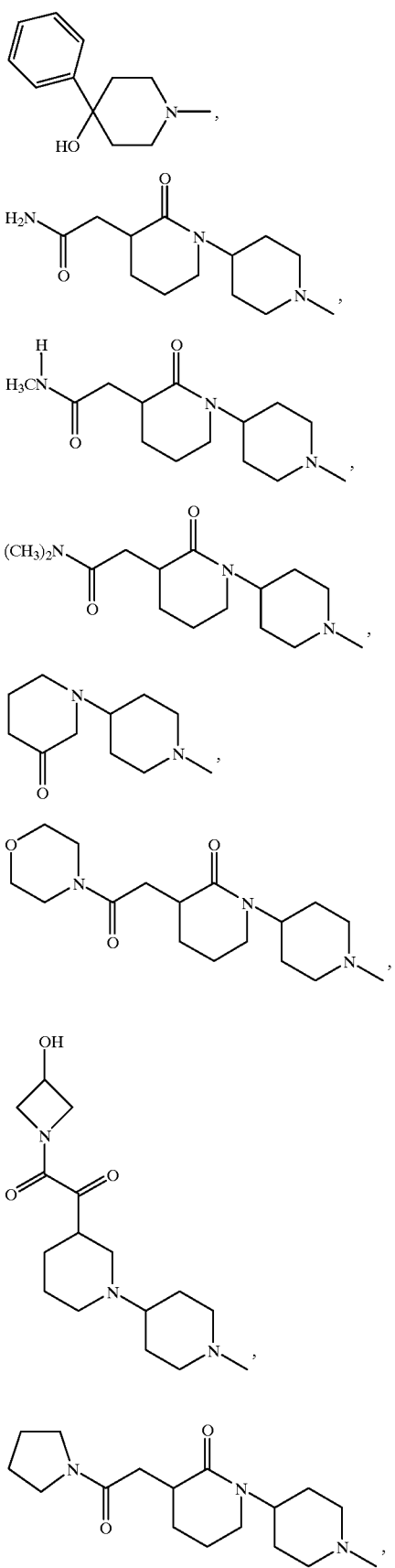

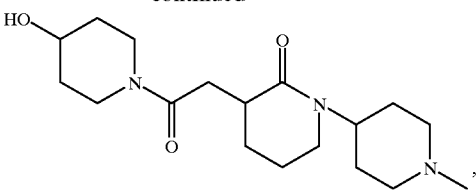

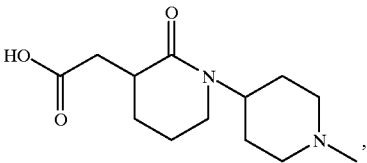

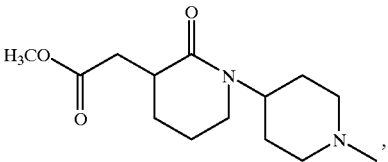

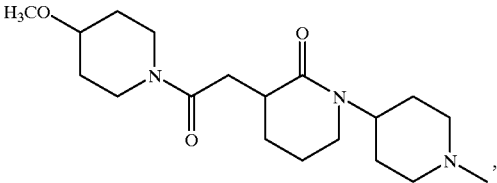

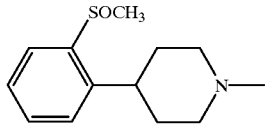

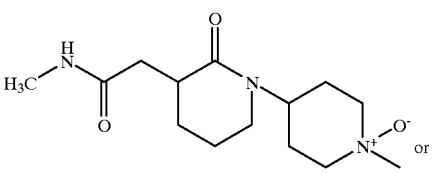 or

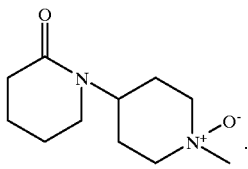

Preferred are Z-isomers of compounds of formula I.

Preferred are compounds of formula I wherein T is $R^2$—phenyl, with compounds wherein $R^2$ is two chloro substituents, two methyl substituents (preferably 3,5-dichloro or 3,5-dimethyl), or two methoxy and one methyl substituent (i.e., 3,5-methoxy4-methyl) being more preferred; compounds wherein $R^2$ is two chloro groups are especially preferred.

Also preferred are compounds of formula I wherein $R^1$ is methyl, —$CH_2F$, —$CH_2CN$, —$(CH_2)_3SO_3H$,

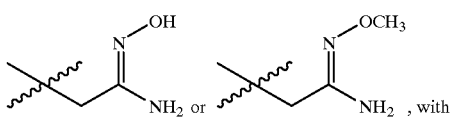

with methyl being more preferred.

$R^4$ is preferably methyl.

Another group of preferred compounds is that wherein Z is,

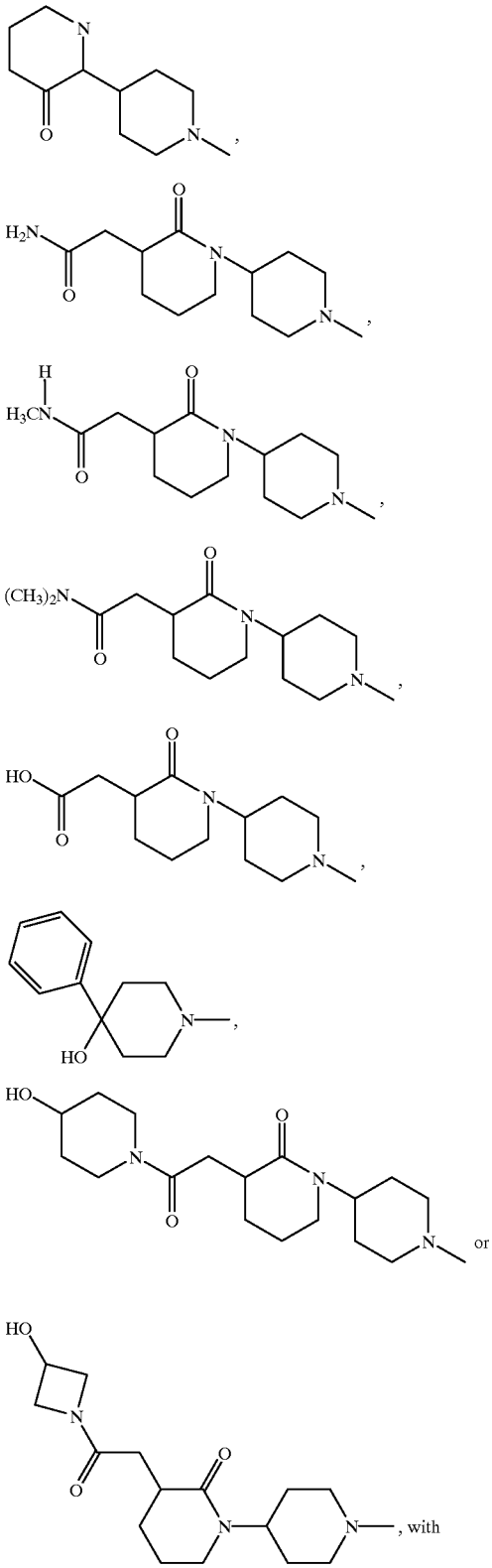

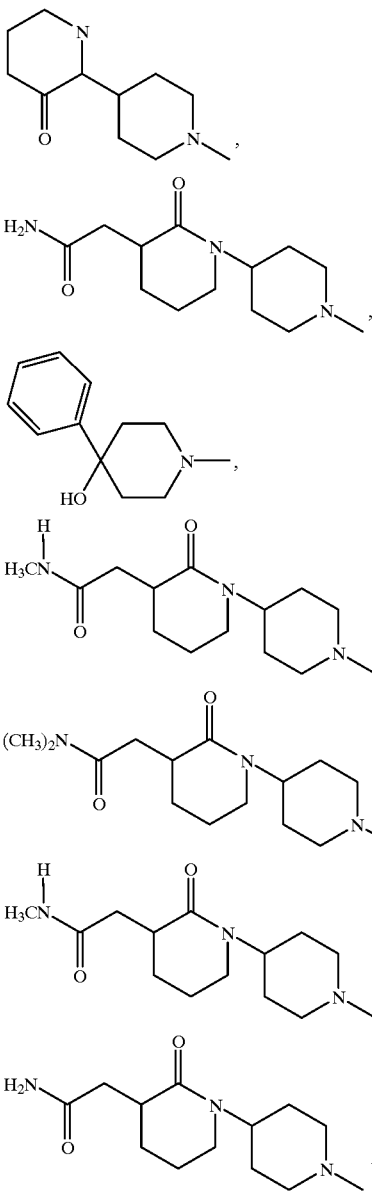

being more and being preferred, and
especially preferred.

This invention also relates to the use of a compound of formula I in the treatment of asthma, cough, chronic obstructive pulmonary disease (COPD), bronchospasm, emesis, neurodegenerative disease, ocular disease, inflammatory diseases such as arthritis, central nervous system conditions such as migraine and epilepsy, nociception, psychosis, and various gastrointestinal disorders such as Crohn's disease.

In another aspect, the invention relates to a pharmaceutical composition comprising a compound of formula I in a pharmaceutically acceptable carrier. The invention also relates to the use of said pharmaceutical composition in the treatment of asthma, cough, chronic obstructive pulmonary disease (COPD), bronchospasm, emesis, neurodegenerative disease, ocular disease, inflammatory diseases such as arthritis, central nervous system conditions such as migraine and epilepsy, nociception, psychosis, and various gastrointestinal disorders such as Crohn's disease.

DETAILED DESCRIPTION

In the structural formulas shown throughout the specification and claims, hydrogen atoms may be understood, e.g., the partial structure

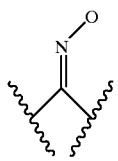

is the same as

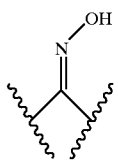

and methyl groups may appear as a line e.g.,

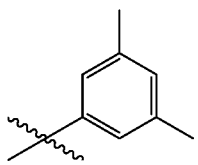

is the same as

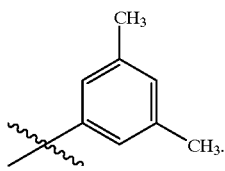

Some formulas may include a methyl group shown as a line, and the point of attachment to another atom shown as a line through which a wavy line is drawn, i.e.,

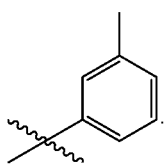

Compounds of formula I can have at least one asymmetric carbon atom and all isomers, including diastereomers, enantiomers and rotational isomers, as well as E and Z isomers of the oxime, hydrazone and olefin groups, are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of formula I.

Those skilled in the art will appreciate that for some compounds of formula I, one isomer will show greater pharmacological activity than other isomers.

Compounds of the invention have at least one amino group which can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, tartaric, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

Compounds of formula I can be prepared using methods well known to those skilled in the art, for example by procedures disclosed in WO 96/34857. The skilled artisan will recognize that other procedures may be applicable, and that the procedure may be suitably modified to prepare other compounds within the scope of formula I.

Compounds of formula I as defined above can be prepared as shown in the following reaction scheme relating to the broader scope of compounds disclosed in WO 96/34857. In the reaction scheme, the variables are as defined above for the PCT application:

Step 1:

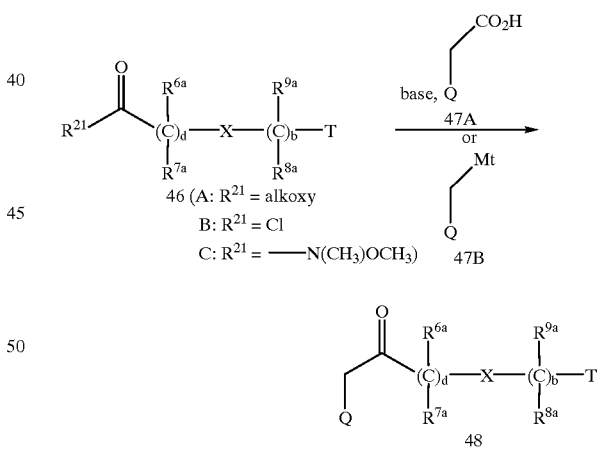

In step 1, a compound of formula 47A. wherein Q is as defined above, is reacted with a base such as lithium diisopropylamide (LDA), KHMDS or KH in an inert organic solvent such as THF or DME to generate a dianion. An acid chloride, ester or amide of formula 46A, 46B, or 46C is added to give a ketone of formula 48. Preferable reaction temperatures ranges from −78° C. to 30° C.

Alternatively, compounds of formula 48 can be generated by the reaction of a compound of formula 46, preferably 46C, with a metallated species of formula $QCH_2Mt$ where Mt is a metal, such as lithium or MgHal, wherein "Hal" is halogen. The metallated species $QCH_2Mt$ can be generated by conventional procedures, such as treatment compounds of formula QCH₂Hal with Mg or by treating QCH₃ with an organolithium base.

Step 2:

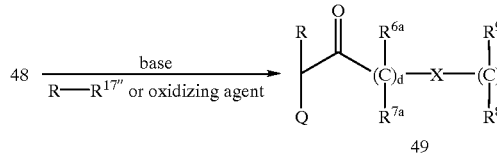

In step 2, for compounds disclosed in the PCT application wherein R is not hydrogen, the ketone 48 is reacted with a suitable base, such as LDA or KH in an inert organic solvent such as THF. For compounds wherein R is alkyl or hydroxyalkyl, a compound R-R$^{17''}$, wherein R$^{17''}$ is leaving group such as Br, I or triflate is added. For compounds of the PCT application wherein R is OH, an appropriate oxidizing agent such as dimethyldioxirane or Davis reagent is added. Preferable reaction temperatures range from −78° to 50° C. For compounds of the present invention, corresponding to compounds of the PCT application wherein R is H, the ketone 48 is used directly in Step 3.

Step 3:

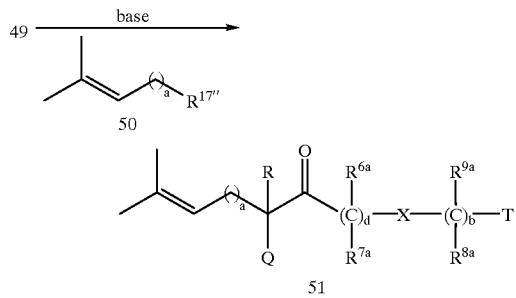

In step 3, ketone 49 is reacted with a base such as LDA in a solvent such as THF, then an olefin of formula 50 is added, wherein R$^{17''}$ is as defined above, to give the adduct 51. Preferable reaction temperatures range from −78° C. to 60° C.

Step 4:

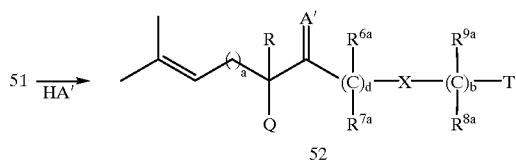

In step 4, ketone 51 is reacted with HA', wherein A' is NH—OR$^1$, in an organic solvent such as pyridine or ethanol at a temperature from 25° C. to 150° C. to give a compound of formula 52.

Step 5:

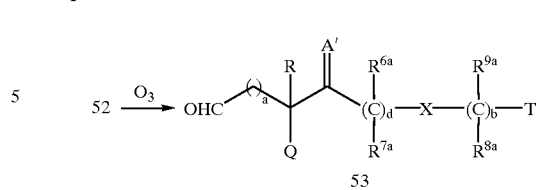

In step 5, a compound of formula 52 is oxidized by ozonolysis to give an aldehyde of formula 53. Suitable organic solvents include EtOAc, CH₃OH, ethanol, CH₂Cl₂ or the like. Preferable reaction temperatures are from −78 to 0° C.

Step 6:

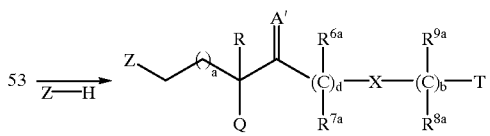

In step 6, an aldehyde of formula 53 is reacted with a compound of formula Z—H, wherein Z is as defined above. The reaction is preferably carried out with a suitably substituted amine (as its acid salt e.g. HCl or maleate or as its free base) and a hydride source such as NaBH₃CN or sodium triacetoxyborohydride in a suitable solvent (e.g. CH₃OH, CH₃CH₂OH, or CF₃CH₂OH for NaBH₃CN, or THF, 1,2-dichloroethane, CH₃CN or CF₃CH₂OH for triacetoxyborohydride), with 3A sieves to obtain the desired product. Any suitable temperature can be used with preferable temperatures between 0° C. and 25° C.

Alternatively, a compound of formula I can be prepared from 51 by the following reaction scheme, wherein the variables are as defined for the cited PCT application:

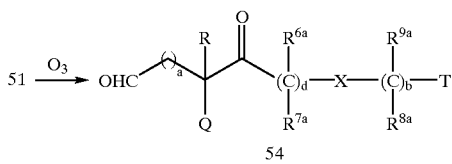

Compound 51 is oxidized to a compound of formula 54 under conditions similar to those described for step 5 above. The aldehyde of formula 54 is reacted with a compound of formula Z—H in a manner similar to that described in Step 6, and the resultant ketone is then reacted with a compound of the formula HA' as described above in Step 4 to obtain the compound of formula I.

Reactive groups not involved in the above processes can be protected during the reactions with conventional protecting groups which can be removed by standard procedures after the reaction. The following Table 1 shows some typical protecting groups:

TABLE 1

| Group to be Protected | Group to be Protected and Protecting Group |
|---|---|
| —COOH | —COOalkyl, —COObenzyl, —COOphenyl, —COOallyl |
| >NH | >NCOalkyl, >NCObenzyl, >NCOphenyl, >NCH$_2$OCH$_2$CH$_2$Si(CH$_3$)$_3$, >NC(O)OC(CH$_3$)$_3$, >N-benzyl, >NSi(CH$_3$)$_3$, >NSi(CH$_3$)$_2$—C(CH)$_3$ |
| —NH$_2$ | 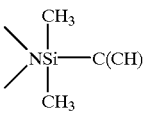 (succinimide) |
| —OH | —OCH$_3$, —OCH$_2$OCH$_3$, —OSi(CH$_3$)$_3$, —OSi(CH$_3$)$_2$—C(CH)$_3$, —Oallyl or —OCH$_2$phenyl |

Compounds of formula I have been found to be antagonists of NK$_1$ and/or NK$_2$ and/or NK$_3$ receptors, and are therefore useful in treating conditions caused or aggravated by the stimulation of said receptors.

The present invention also relates to a pharmaceutical composition comprising a compound of formula I and a pharmaceutically acceptable carrier. Compounds of this invention can be administered in conventional oral dosage forms such as capsules, tablets, powders, cachets, suspensions or solutions, or in injectable dosage forms such as solutions, suspensions, or powders for reconstitution The pharmaceutical compositions can be prepared with conventional excipients and additives, using well known pharmaceutical formulation techniques. Pharmaceutically acceptable excipients and additives include non-toxic and chemically compatibile fillers, binders, disintegrants, buffers, preservatives, anti-oxidants, lubricants, flavorings, thickeners, coloring agents, emulsifiers and the like.

The daily dose of a compound of formula I for treating asthma, cough, bronchspasm, inflammatory diseases, migraine, nociception and gastrointestinal disorders is about 0.1 mg to about 20 mg/kg of body weight per day, preferably about 0.5 to about 15 mg/kg. For an average body weight of 70 kg, the dosage range is therefore from about 1 to about 1500 mg of drug per day, preferably about 50 to about 200 mg, more preferably about 50 to about 500 mg/kg per day, given in a single dose or 2–4 divided doses. The exact dose, however, is determined by the attending clinician and is dependent on the potency of the compound administered, the age, weight, condition and response of the patient.

Following are examples of preparing starting materials and compounds of formula I. As used herein, Me is methyl, Bu is butyl, Br is bromo, Ac is acetyl, Et is ethyl and Ph is phenyl.

Preparation 1

1-[[(3,5-bis(trifluoromethyl)phenyl]methoxy]-3-(3,4-dichlorophenyl)-5-(4-hydroxy-4-phenyl-1-piperidinyl)-2-pentanone

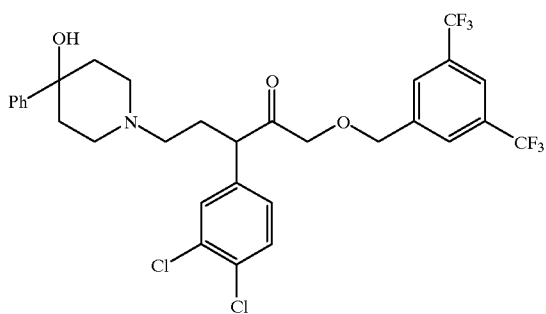

Treat a solution of (cis)-[[[(3,5-bis(trifluoromethyl)phenyl]methoxy]methyl]4-(3,4-dichlorophenyl)-4-hydroxy-4-phenyl-1-piperidinebutanol (2.0 g, 3.08 mmol) in acetone (90 mL, 0° C.) with Jones reagent (9 mL of H$_2$CrO$_4$ in H$_2$SO$_4$ (ca. 8 M)). Stir the light orange suspension at 0° C. for 1 h, then partition between CH$_2$Cl$_2$ (150 mL) and saturated aqueous NaHCO$_3$ (150 mL). Extract the aqueous layer with CH$_2$Cl$_2$ (3×150 mL), back extract the combined organic layers with saturated aqueous NaHCO$_3$ (150 mL), dry (Na$_2$SO$_4$) and concentrate to give 1.94 g crude product. Purify by silica gel chromatography (column: 4 cm×15 cm; eluant: EtOAc:hexane: triethylamine (66:33:2)) to obtain 1.64 g (2.53 mmol, 82%) of the title compound as a colorless foam. HRMS (FAB, M+H$^+$): m/e calc'd for [C$_{31}$H$_{30}$NO$_3$Cl$_2$F$_6$]$^+$: 648.1507, found 648.1496.

Preparation 2

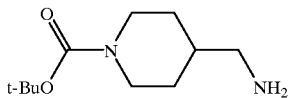

Step 1:

Dissolve 4-aminomethyl-piperidine (30.00 g, 0.263 mol) in CH$_3$OH (500 mL), cool to −30° C. under N$_2$, add di-t-butyl dicarbonate (38.23 g, 0.175 mol) in CH$_3$OH (100 mL) dropwise, warm slowly to 23° C. and stir for 16 h. Concentrate, add CH$_2$Cl$_2$ (700 mL), wash with saturated aqueous NaCl (2×200 mL), dry organic solution (MgSO$_4$), filter and concentrate to give 36.80 g of a 86:14 mixture of the title compound and 1,1-dimethylethyl 4-[(1,1-dimethylethyloxycarbonyl)methyl]-1-piperidinecarboxylate.

Step 2A:

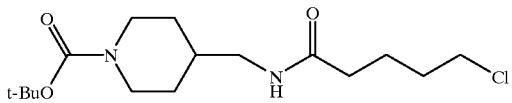

Dissolve the product (19.64 g, 0.0916 mol, 22.84 g of the mixture) of Step 1 in dry CH$_2$Cl$_2$ (350 mL) and cool to 0° C. under N$_2$. Add pyridine (10.87 g, 11.1 mL, 0.137 mol) then chlorovaleryl chloride (15.63 g, 13.0 mL, 0.101 mol), warm slowly to 23° C. and stir for 16 h. Add saturated aqueous NH$_4$Cl (300 mL), separate layers and extract with CH$_2$Cl$_2$ (2×250 mL). Dry combined organic extracts (MgSO$_4$), filter and concentrate. Purify by chromatography (1000 mL of flash silica gel; eluant: 1:1 EtOAc:hexane, then EtOAc). Combine appropriate fractions and concentrate to give 25.36 g (0.0762 mol, 84%) as a colorless oil. MS (Cl/CH$_4$): m/e 333 (M+1)

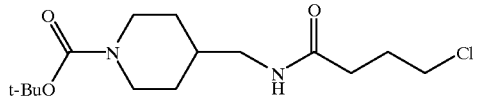

Step 2B:

Treat the product of Step 1 in a procedure similar to that described for Step. 2A, using chlorobutryl chloride. MS (FAB): m/e 319 (M+1)

Step 3:

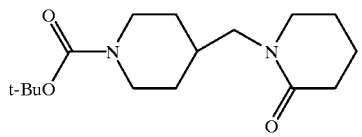

Prep. 2A:

Wash NaH (3.84 g, 0.160 mol, 6.40 g of 60 wt %) with hexane (25 mL), suspend in dry THF (150 mL) and cool to 0° C. under N$_2$. Add the product (25.35 g, 0.0762 mol) of Step. 2A in dry THF (150 mL) dropwise. Stir at 23° C. for 30 mins, reflux for 6 h, and stir at 23° C. for 16 h. Cool to 0° C. and add water (150 mL) and 1 N HCl (150 mL). Concentrate and extract with EtOAc (3×200 mL). Wash combined organic extracts with saturated aqueous NaCl, dry (MgSO$_4$), filter and concentrate. Purify by chromatography (600 mL of flash silica gel; eluant: 5% CH$_3$OH—CH$_2$Cl$_2$). Combine appropriate fractions and concentrate to give 21.62 g (0.0729 mol, 96%) of the title compound as a yellow oil. MS (FAB): m/e 297 (M+1)

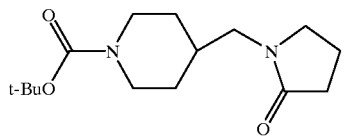

Prep. 2B:

Treat the product of Step 2B in a procedure similar to that described for Prep. 2A. MS (FAB): m/e 283 (M+1).

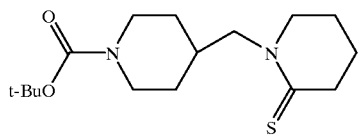

Prep. 2C:

Combine the product (1.50 g, 5.06 mmol) of Prep. 2A and Lawesson reagent (1.13 g, 2.78 mmol) in dry THF (20 mL) under N$_2$. Stir at 23° C. for 20 h. Concentrate and purify by chromatography (200 mL of flash silica gel; eluant: 1:3 EtOAc:hexane, 1:2 EtOAc:hexane, then 1:1 EtOAc:hexane). Combine appropriate fractions and concentrate to give 1.30 g (4.16 mmol, 82%) as a green oil. MS (FAB): m/e 313 (M+1).

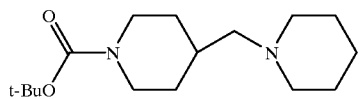

Prep. 2D:

Dissolve the product (2.50 g, 8.43 mmol) of Prep. 2A in dry THF (30 mL), add borane-DMS (16.9 mL of 2.0 M in THF, 33.74 mmol) and reflux for 20 h. Cool to 0° C. and add CH$_3$OH (20 mL). Concentrate, add EtOH (50 mL) and K$_2$CO$_3$ (4.66 g, 33.74 mmol). Reflux for 4 h and cool to 23° C. Add water (100 mL), concentrate and extract with CH$_2$Cl$_2$ (4×50 mL). Dry combined organic extracts (MgSO$_4$), filter and concentrate. Purify by chromatography (200 mL of flash silica gel; eluant: 7% CH$_3$OH—CH$_2$Cl$_2$). Combine appropriate fractions and concentrate to give 1.72 g (6.09 mmol, 72%) of the title compound as a colorless oil. MS (FAB): m/e 283 (M+1).

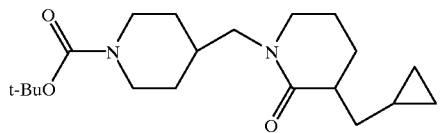

Prep. 2E:

Dissolve the product (1.50 g, 5.06 mmol) of Prep. 2A in dry THF (20 mL) and cool to −78° C. under N$_2$. Add [(CH$_3$)$_3$Si]$_2$NLi (5.5 mL of 1.0 M in THF, 5.5 mmol) and stir at −78° C. for 1 h. Add bromomethylcyclopropane (0.820 g, 0.59 mL, 6.07 mmol), warm slowly to 23° C. and stir for 16 h. Add saturated aqueous NH$_4$Cl (40 mL), extract with EtOAc (3×30 mL), wash combined organic extracts with saturated aqueous NaCl, dry (MgSO$_4$), filter and concentrate. Purify by chromatography (175 mL of flash silica gel; eluant: 2% CH$_3$OH—CH$_2$Cl$_2$ then 4% CH$_3$OH—CH$_2$Cl$_2$). Combine appropriate fractions and concentrate to give 0.93 g (2.65 mmol, 53%) of the title compound as a colorless oil. MS (FAB): m/e 351 (M+1)

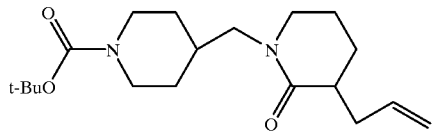

Prep. 2F:

Treat the product of Prep. 2A in a procedure similar to that described for Prep. 2E, using allyl bromide. MS (Cl/CH$_4$): m/e 337 (M+1).

Step 4: Separately dissolve the products of Prep. 2A to 2F in CH$_2$Cl$_2$, add trifluoroacetic acid and stir at 23° C. for 4 h. Concentrate, add 1 N NaOH, extract with CH$_2$Cl$_2$, dry the combined organic extracts (MgSO4), filter and concentrate to obtain the corresponding substituted piperidines:

| Prep. | Substituted Piperidine | Data |
|---|---|---|
| 2-A | | MS (Cl/CH$_4$): m/e 197 (M + 1) |
| 2-B | | MS (Cl/CH$_4$): m/e 183 (M + 1) |
| 2-C | | MS (Cl/CH$_4$): m/e 213 (M + 1) |
| 2-D | | MS (Cl/isobutane): m/e 183 (M + 1) |
| 2-E | | MS (Cl/CH$_4$): m/e 251 (M + 1) |
| 2-F | | MS (Cl/CH$_4$): m/e 237 (M + 1) |

Preparation 3

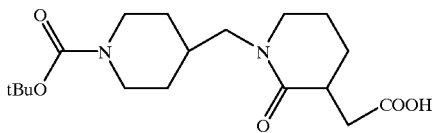

Step 1: Using the procedures of Preparation 2, substitute 4-amino-1-benzylpiperidine for 4-aminomethyl-1-(1,1-dimethylethyloxycarbonyl)-piperidine in Prep. 2, Step 2A and proceed through Prep. 2, Step 3.

Step 2: Treat palladium hydroxide (2.0 g) in EtOAc (100 mL) with the product of Step 1 (25.0 g, 0.0918 mol) in EtOAc (200 mL) and (tBOC)$_2$O in EtOAc (200 mL). Shake the resulting mixture on a Parr shaker at 50 psi of H$_2$ pressure for 3 h then add more palladium hydroxide catalyst (2 g) and shake for 16 h. Filter off catalyst and wash with EtOAc. Concentrate and purify by chromatography (silica gel; eluant: 5% CH$_3$OH—CH$_2$Cl$_2$). Combine appropriate fractions and concentrate to give 24.37 g of the product as a white solid. MS (FAB): m/e 283 (M+1).

Step 3: Treat the product of Step 2 according to a procedure similar to that described for Preparation 2F. MS (Cl/CH$_4$): m/e 267 (M−55).

Step 4A: Treat the product of Step 3 (5.17 g, 16.0 mmol) in EtOAc (90 mL) and H$_2$O (90 mL) with NaIO$_4$ (20.57 g, 96.2 mmol) and RuO$_2$ (0.064 g, 0.48 mmol). Stir at 23° C. for 5 h, add 1 N HCl (20 mL) and filter. Wash solid with EtOAc and H$_2$O. Separate layers of filtrate and extract with EtOAc. Dry combined organic extracts (MgSO$_4$), charcoal, and concentrate to give 5.10 g of the title compound. MS (FAB): m/e 341 (M+1).

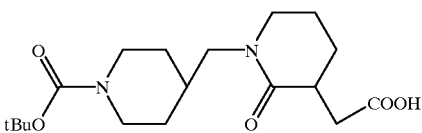

Step 4B: Treat the product of Preparation 2F according to a procedure similar to that described in Step 4A to give the protected amino acid.

Step 5A: The substituted piperazines 3A5 to 3H5 as well as 3N5 and 3O5 are prepared in a similar procedure using the appropriate amine. Treat the product of Step 4A (1.00 g, 2.94 mmol) in CH$_2$Cl$_2$ (20 mL) with carbonyl-diimidazole (0.57 g, 3.53 mmol) and stir at 23° C. for 4 h. Add the appropriate amine and stir for 16 h. Add 1 N HCl and extract with CH$_2$Cl$_2$. Dry the combined organic extracts (MgSO$_4$), filter, and concentrate. Purify by chromatography (silica gel; eluant: CH$_3$OH—CH$_2$Cl$_2$). Combine appropriate fractions and concentrate to give 3A5 to 3H5 and 3N5-3O5.

Step 5B: The compounds 3I5 to 3K5 are prepared in a similar procedure to that described in Step 5A substituting the product of Step 4B for the product of Step 4A using the appropriate amine.

Preparation 3L5: Treat the product of Preparation 3, Step 2 according to a procedure similar to that described for Preparation 2F, substituting the product of Example 18L, Step 2, in place of allyl bromide to obtain the title compound.

| Prep | Substituted Piperidine | MS |
|---|---|---|
| 3A5 | | (FAB) m/e 368 (M + 1) |

-continued

| Prep | Substituted Piperidine | MS |
|------|------------------------|-----|
| 3B5 | | (Cl/CH$_4$) m/e 355 (M + 1) |
| 3C5 | | (Cl/CH$_4$) m/e 284 (M − 55) |
| 3D5 | | (FAB) m/e 410 (M + 1) |
| 3E5 | | (FAB) m/e 394 (M + 1) |
| 3F5 | | (FAB) m/e 396 (M + 1) |
| 3G5 | | (FAB) m/e 384 (M + 1) |
| 3H5 | | (FAB) m/e 424 (M + 1) |
| 3I5 | | (FAB) m/e 398 (M + 1) |
| 3J5 | | (Cl/CH$_4$) m/e 354 (M + 1) |

| Prep | Substituted Piperidine | MS |
|---|---|---|
| 3K5 | (structure: tBuO-C(O)-N-piperidine-CH2-N-piperidinone-CH2-C(O)-N-morpholine) | (Cl/CH₄) m/e 424 (M + 1) |
| 3L5 | (structure: tBuO-C(O)-N-piperidine-N-piperidinone-CH2-C(O)-NH-OMe) | (FAB) m/e 370 (M + 1) |
| 3N5 | (structure: tBuO-C(O)-N-piperidine-N-piperidinone-CH2-C(O)-N-piperazine-N-CH3) | (FAB) m/e 423 (M + 1) |
| 3O5 | (structure: tBuO-C(O)-N-piperidine-N-piperidinone-CH2-C(O)-N-thiomorpholine) | (FAB) m/e 426 (M + 1) |

Step 6: The compounds 3A6 to 3N6 are prepared by treating the products 3A5 to 3O5 (Step 5] according to a procedure similar to Prep. 2, Step 4. Preparation of 3O6 is carried out by treating the product of Preparation 3, Step 1 according to a procedure similar to that described for Preparation 3, Step 2, omitting the (t-BOC)₂O to obtain the title compound.

| Preparation | Substituted Piperidine | MS |
|---|---|---|
| 3A6 | (structure: HN-piperidine-N-piperidinone-CH2-C(O)-NMe2) | (Cl/CH₄) m/e 268 (M + 1) |
| 3B6 | (structure: HN-piperidine-N-piperidinone-CH2-C(O)-NHMe) | (Cl/CH₄) m/e 254 (M + 1) |
| 3C6 | (structure: HN-piperidine-N-piperidinone-CH2-C(O)-NH2) | (FAB) m/e 240 (M + 1) |

-continued
| Preparation | Substituted Piperidine | MS |
|---|---|---|
| 3D6 | 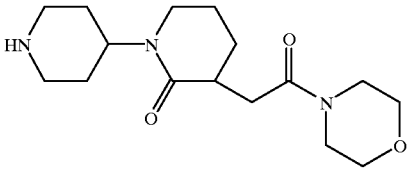 | (Cl/CH₄) m/e 310 (M + 1) |
| 3E6 | 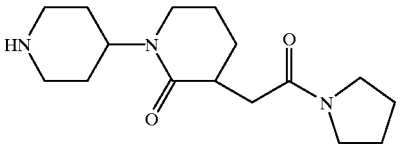 | (Cl/CH₄) m/e 294 (M + 1) |
| 3F6 | 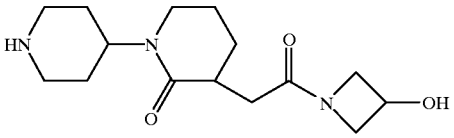 | (Cl/CH₄) m/e 284 (M + 1) |
| 3G6 | 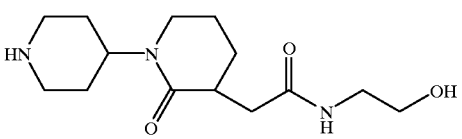 | (Cl/CH₄) m/e 296 (M + 1) |
| 3H6 | 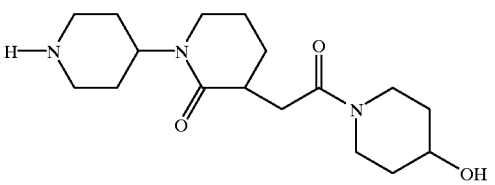 | (FAB) m/e 324 (M + 1) |
| 3I6 | 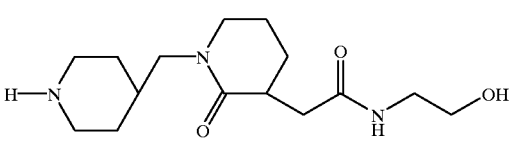 | (Cl/CH₄) m/e 298 (M + 1) |
| 3J6 | 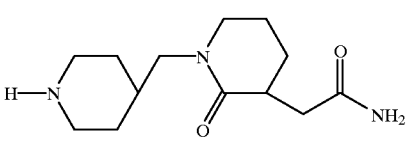 | (Cl/CH₄) m/e 254 (M + 1) |
| 3K6 | 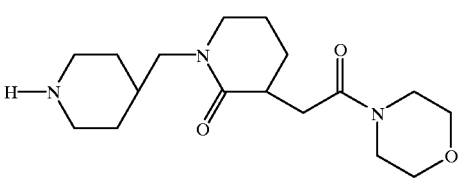 | (Cl/CH₄) m/e 324 (M + 1) |
| 3L6 | 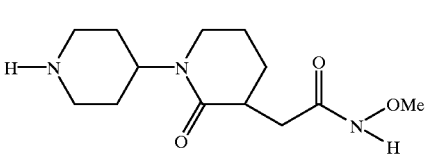 | |

-continued

| Preparation | Substituted Piperidine | MS |
|---|---|---|
| 3M6 | | (FAB) m/e 323 (M + 1) |
| 3N6 | | (FAB) m/e 326 (M + 1) |
| 3O6 | | (FAB) m/e 183 (M + 1) |

Preparation 4

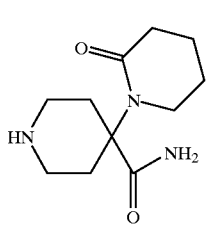

Preparation 4A

Step 1: Treat N-benzyl-piperidone (8.00 g, 0.0423 mol) in $CH_2Cl_2$ with $(CH_3)_3SiCN$ (4.82 g, 0.0486 mol) and $ZnI_2$ (0.68 g, 0.0021 mol). Stir at 23° C. for 16 h and concentrate. Add $CH_3OH$ saturated with $NH_3$ (30 mL) and heat at 40° C. Concentrate the resulting mixture, add $CH_2Cl_2$ (200 mL), dry ($MgSO_4$), filter and concentrate to give 11.06 g of the desired product as a yellow oil. MS ($Cl/CH_4$): m/e 189 (M−26).

Step 2: Treat the product of Step 1 according to a procedure similar to that of Preparation 2, Steps 2A and 3. MS ($Cl/CH_4$): m/e 298 (M+1).

Step 3: Treat the product of Step 2 (1.50 g, 5.04 mmol) in t-BuOH (25 mL) with KOH (0.99 g, 17.64 mmol) and reflux for 30 min. Cool to 23° C. and concentrate. Add saturated NaCl (40 mL), extract with $CH_2Cl_2$ (3×40 mL), dry ($MgSO_4$), filter and concentrate. Purify by flash chromatography (silica gel; eluant: 10% $CH_3OH$—$CH_2Cl_2$). Combine appropriate fractions and concentrate to give 0.98 g of the desired product as a yellow solid. M.p.=184–186° C. MS (FAB): m/e 298 (M−17).

Step 4: Treat the product of Step 3 (0.97 g, 3.08 mmol) in $CH_3OH$ (25 mL) with palladium hydroxide (0.40 g). Shake on Parr shaker at 50 psi of $H_2$ pressure for 16 h. Filter, wash with $CH_3OH$ and concentrate to give 0.69 g of the title compound as a white solid. m.p.=180–185° C. MS (FAB): m/e 210 (M−15)

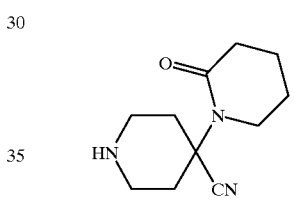

Preparation 4B

Step 1: Treat the product of Prep. 4A, Step 2 (1.50 g, 5.04 mmol) in $CH_2Cl_2$ (25 mL) with trichloroethyl chloroformate (TROC-Cl) (1.39 g, 6.55 mmol). Stir at 23° C. for 16 h. Add 0.25 N NaOH (40 mL), extract with $CH_2Cl_2$ (3×40 mL), dry ($MgSO_4$), filter and concentrate. Purify by flash chromatography (silica gel; eluant: 1:1 EtOAc: hexane to 2:1 EtOAc:hexane). Combine appropriate fractions and concentrate to give 1.31 g of the desired compound as a white solid. m.p.=185–186° C. MS ($Cl/CH_4$): m/e 382 (M+1).

Step 2: Treat the product of Step 1 (1.30 g, 3.40 mmol) in THF (20 mL) with HOAc (1.9 mL, 34.0 mmol) and zinc (2.22 g, 34.0 mmol). Stir at 23° C. for 18 h. Add $H_2O$ (10 mL), filter and wash with EtOAc. Add 6.25 N NaOH to filtrate, extract with $CH_2Cl_2$, dry ($MgSO_4$), filter and concentrate to give 0.70 g of the title compound as a white solid. MS ($Cl/CH_4$): m/e 208 (M+1).

Preparation 4C

Step 1: Treat 4-cyano-4-phenylpiperidine in $CH_3OH$ with 50% $KOH/H_2O$ and heat in a sealed tube at 180° C. for 2 h. Cool to 23° C. and concentrate give the desired compound.

Step 2: Treat the product of Step 1 with di-t-butyl-dicarbonate according to a procedure similar to that in Preparation 2 Step 1 to give the protected amino acid.

Step 3: Couple the product of Step 2 with morpholine according to a procedure similar to Example 8 using DMF as a solvent.

Step 4: Deprotect the amine using a procedure similar to Prep. 2, Step 4, optionally substituting HCl for TFA.

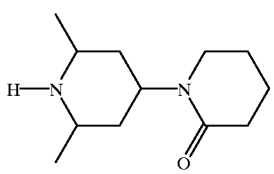

Preparation 4D

Step 1 Cool acetaldehyde (4.6 g, 105 mmol) and dimethylacetone dicarboxylate (7.1 g, 35 mmol) to 0° C. and treat with benzylamine (5.2 g, 49 mmol), 12 N HCl, (4.1 mL), and H$_2$O (3 mL). Stir at 23° C. for 16 h. Concentrate the reaction mixture, add acetone (20 mL), filter and concentrate. Add 6 N HCl (30 mL) and heat at 80° C. for 16 h. Cool the resulting solution to 23° C., basify to pH 10 with KOH pellets and extract with CH$_2$Cl$_2$ (3×80 mL). Dry combined organic extracts (MgSO$_4$), filter and concentrate. Purify by flash chromatography (silica gel; eluant: 10% EtOAc-hexane). Combine appropriate fractions and concentrate to give 1.8 g of yellow oil. MS (FAB) m/e 218 (M+1).

Step 2: Treat the product of Step 1 (1.7 g, 8.3 mmol) in CH$_3$OH (10 mL) with H$_2$NOH•HCl (1.2 g, 16.8 mmol) and CH$_3$CO$_2$Na (2.05 g, 25 mmol). Reflux for 4 h then cool to 23° C. and concentrate. Add saturated NH$_4$Cl and extract with CH$_2$Cl$_2$. Dry combined organic extracts (Na$_2$SO$_4$), filter and concentrate to give 1.6 g of brown oil. MS (FAB) m/e 233 (M+1).

Step 3: Treat the product of Step 2 (1.5 g, 6.46 mmol) in EtOH (20 mL) with Raney nickel (1 g, washed with EtOH). Shake on Parr shaker at 41 psi of H$_2$ pressure for 16 h. Filter the reaction mixture and concentrate. Purify by flash chromatography (silica gel; eluant: 7% CH$_3$OH with NH$_3$—CH$_2$Cl$_2$). Combine appropriate fractions and concentrate to give 0.85 g of a clear oil. MS (FAB) m/e 217 (M+1).

Step 4: Proceed in a similar fashion as described for Preparation 3O6 substituting the product of Step 3 for 4-amino-N-benzylpiperidine. MS (FAB) m/e 211 (M+1).

Preparation 5

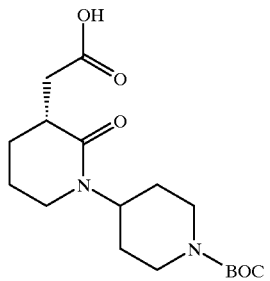

Step 1: Cool a solution of (R)-(+)-4-benzyl-2-oxazolidinone (100 g, 563 mmol) and 1,10-phenanthroline (10 mg) in dry THF (1.25 L) to −78° C. and add n-BuLi via addition funnel at a rate such that the internal temperature remains ≦−70° C. Add n-BuLi (350 mL of 1.6 M in hexane, 350 mmol, 1 eq) until the reaction turns brown from the phenanthroline complex (ca. 349.5 mL). After 15 min, add 3-carbomethoxypropionyl chloride (69.5 mL, 564 mmol, 1 eq) over 10 min via syringe. Stir the resulting solution for 30 min at −78° C. Allow the mixture to warm to 23° C. then pour into EtOAc (2.5 L)/sat. NH$_4$Cl (1 L). Wash the organic layer with saturated NH$_4$Cl (1 L), saturated NaHCO$_3$ (2.5 L) and saturated NaCl (2.5 L), then dry (MgSO$_4$) and concentrate to obtain a yellow solid. Recrystallize the solid from hot isopropanol (820 mL) to give 157.9 g (542 mmol, 98%) of pure product as a colorless crystalline solid, mp 90–92° C.

Step 2: Cool a solution of TiCl$_4$ (419 mL of 1 M in CH$_2$Cl$_2$, 419 mmol) in dry CH$_2$Cl$_2$ (1.35 L) to 0° C. and treat with Ti(Oi-Pr)$_4$ (41.4 mL, 140 mmol) via syringe. After 10 min at 0° C., add diisopropylethyl amine (102.4 mL, 587 mmol) via dry addition funnel. Stir the resulting solution for 15 min at 0° C. then add the product of Step 1 (163.2 g, 561 mmol) in one portion. Stir the solution for 1 h at 0° C. then add freshly distilled acrylonitrile (147 mL, 2.24 mol) via dry addition funnel. Allow the resulting mixture to stand at 4° C. for 18 h then pour the reaction mixture into 25% aq NH$_4$Cl (4 L)/EtOAc (6 L). Wash the organic layer with 12.5% aq NH$_4$Cl (2×4 L), saturated NaHCO$_3$ (4 L), and saturated NaCl (4 L) then dry (MgSO$_4$) and concentrate. Dissolve the crude product in EtOAc and filter through a pad of silica gel (500g). Concentrate the filtrate (6 L) and recrystallize in hot CH$_3$OH (4 ml/g) to give 116.5 g (338.3 mmol, 60%) of the pure product as a colorless crystalline solid, mp. 103–105° C.

Step 3: Treat a solution of the product of Step 2 (25g, 72.6 mmol) in CHCl$_3$ (100 mL) and CH$_3$OH (400 mL) with PtO$_2$ (1.25 g) and place on the Parr shaker @45 psi. Shake for 24 h, then filter the mixture through a pad of Celite. Concentrate the filtrate to give 28.3 g of crude amine•HCl.

Step 4: Treat a solution of the product of Step 3 (72.6 mmol) in 1,2-dichloroethane (500 mL) with HOAc (6 mL, 105 mmol, 1.4 eq) followed by N-Boc-4 piperidone (14.6 g, 73.5 mmol, 1.01 eq,) and NaB(OAc)$_3$H (25.7 g, 122 mmol, 1.7 eq). Stir for 1.0 h, then pour the mixture into CH$_2$Cl$_2$ (1.4 L). Wash with saturated aqueous NaHCO$_3$ (2×560 mL), dry (MgSO$_4$) and concentrate to give 39.1 g of product.

Step 5: Stir a solution of the product of Step 4 (72.6 mmol) in CH$_3$CN (500 mL) for 72 h at 50° C. Cool and concentrate to give 39.3 g of lactam.

Step 6: Treat a solution of the product of Step 5 (39.3g) (containing up to 72.6 mmol of a mixture of N-benzyl and N-methyl-cyclohexyl oxazolidinones) in CH$_3$OH (150 mL), with NaOH (148 mL of 1 N aqueous NaOH, 2.2 eq). Stir for 6 h at 23° C., then concentrate. Add H$_2$O (50 mL) and wash with EtOAc (3×200 mL) to remove the oxazolidinone. Acidify to pH 2 with 40 mL of 15% aq. HCl (4.4 M) and extract with CH$_2$Cl$_2$ (4×200 mL). Dry (MgSO$_4$) the combined extracts and concentrate to give the pure acid as a colorless foam (22.3 g, 65.5 mmol, 96% ee). Recrystallize from hot acetone (18 mL/g, reflux, filter, cool, remove ca. 300 mL solvent on rotovap, seed and sonicate, cool to 10° C., isolate by filtration with 50 mL cold acetone wash) to give 16.5 g (48.5 mmol) of the pure product as a colorless solid, 16.5 g, (48.5 mmol, 67% from the product of Step 2); m.p. 145–147° C., >99% ee by chiral HPLC: Daicel Chiracel OD column, 85:15 hexane/isopropanol with 0.1% TFA).

Step 7: Treat a solution of the product of Step 6 (1 0.0g, 0.029 mol) in CH$_2$Cl$_2$ (100 mL) with HOBT (6.0 g, 0.044 mol), the appropriate amine in THF (or dioxane) (0.044 mol), and DCC (9.1 g, 0.044 mol). Stir at 23° C. for 4 h. Filter and wash with 0.5 N NaOH. Separate layers, extract with CH$_2$Cl$_2$, dry (MgSO$_4$), filter and concentrate. Purify by flash chromatography (silica gel, eluant: EtOAc then 5% CH$_3$OH—EtOAc). Combine appropriate fractions and concentrate to give the product.

Step 8: Treat a solution of the product of Step 7 in CH$_2$Cl$_2$ (125 mL) with TFA (25 mL). Stir at 23° C. for 4 h and concentrate. Add H$_2$O (25 mL) and basiify with 20 wt %

NaOH. Extract with 20% EtOH in CH$_2$Cl$_2$ (7×100 mL), dry (MgSO$_4$), filter, and concentrate to give the products 5A to 5C.

| Preparation | Substituted Piperidine | MS |
|---|---|---|
| 5A | ![5A structure] | (Cl/CH$_4$) m/e 268 (M + 1) |
| 5B | ![5B structure] | (Cl/CH$_4$) m/e 254 (M + 1) |
| 5C | ![5C structure] | (FAB) m/e 240 (M − 55) |

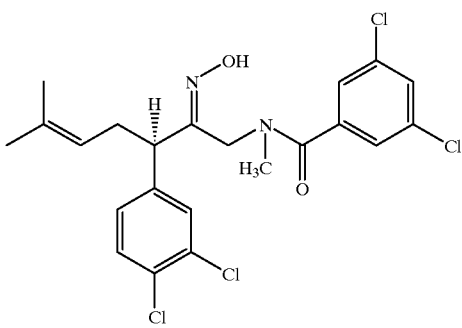

Step 1: Use the procedures of Example 11, Steps 1, 2 and 3, using 3,5-dichlorobenzoyl chloride in place of 3,5-bistrifluorobenzoyl chloride, to obtain the corresponding ketone product.

Step 2: Treat the product of Step 1 with H$_2$NOH HCl using a procedure similar to that described in Example 1 to obtain the title compound. Separation of the Z/E oxime mixture was performed by SiO$_2$ chromatography, eluting with mixtures of EtOAc:CH$_2$Cl$_2$ to obtain the pure Z isomer as a colorless solid.

Method A:
Step 3A: Dissolve the product of Step 2 (134 g) in CH$_2$Cl$_2$ (1.5 L). Treat sequentially with HOBT (44.6 g), BOC-D-phenylglycine (86.3 g) and DEC (65.9 g). Stir the mixture at 23° C. for 18 h, heat at reflux temperature for 2 h, recool to 23° C., treat with saturated NaHCO$_3$ solution (500 mL), separate the organic portion, dry (MgSO$_4$), filter and concentrate. Recrystallize the crude material, once from Et$_2$O and twice from $^i$Pr$_2$O to give 1,1-dimethylethyl-[[[1-[[(3,5-dichlorobenzoyl)methylamine]methyl]-2-(3,4-dichlorophenyl)-5-methyl-hexen-1-ylidene]amino]oxy]-2-oxo-1-phenylethyl]carbamate (51 g). MS(FAB): m/e 722; [α]$_D$$^{23}$=−96.9° (c 0.4 CH$_2$Cl$_2$); m.p. 98–102° C. (dec).

Step 4A: Dissolve the product of Step 3A, (25.2 g) in a 0.5M solution of H$_2$NNH$_2$ in CH$_2$Cl$_2$:CH$_3$OH (2:1) (200 mL) and stir at 23° C. for 30 min. Dilute the reaction mixture with CH$_2$Cl$_2$ (100 mL), wash with H$_2$O (100 mL), dry (MgSO$_4$), filter and concentrate. Purify the product by filtration through a pad of silica gel eluting with CH$_2$Cl$_2$ to give the title compound (15.6 g). MS(FAB): m/e 647.

Method B:
Step 3B: Dissolve the product of Step 2 (750 g) in CH$_2$Cl$_2$ (4.5 L) at 0° C. Treat sequentially with Et$_3$N(233 g), DMAP (2.8 g) and pivaloyl chloride (204 g). Stir the mixture at low temperature, adding additional CH$_2$Cl$_2$ (4 L) to maintain homogeneity. After 20 min., add H$_2$O (100 mL), stir for 10 min., wash with saturated NaHCO$_3$ solution (2 L), H$_2$O (2 L), dry (Na$_2$SO$_4$) and concentrate at 23° C. Purify the oily product by filtration through a pad of silica gel eluting with CH$_2$Cl$_2$ to give 3,5-dichloro-N-[3-(3,4-dichlorophenyl)-2-[[(2,2-dimethyl-3-oxopropoxy]imino]-6-methyl-5-heptenyl]-N-methylbenzamide (846 g).

Step 4B: The product from Step 3B is resolved using a Chiralpak AD™ column, eluting with mixtures of hexane/$^i$PrOH.

Step 5B: Treat the desired enantiomer from Step 4B according to a procedure similar to Method A-Step 4A to afford the title compound.

Preparation 7

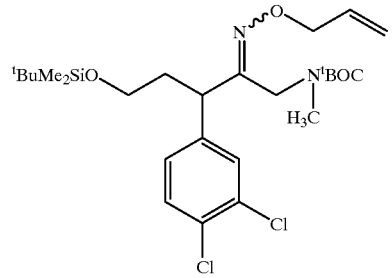

Step 1: Treat a solution of 3,4-dichlorophenylacetic acid (25 g) with N-tBOC-sarcosine methyl ester (24.3 g) (prepared from sarcosine methyl ester HCl and di-t-butyidicarbonate) according to a procedure similar to Example 11, Step 2, to give the desired product (36 g).

Step 2: Treat 2-bromoethanol (107 g) in $CH_2Cl_2$ (2 L) at 0° C. with t-butyidimethylsilylchloride (143 g), $NEt_3$ (130 g) and DMAP (11 g), allow the reaction mixture to warm to 23° C. and stir for 18 h. Wash the mixture with $H_2O$ (250 mL), 20% HCl (250 mL), 20% $NH_4OH$ (250 mL), dry ($MgSO_4$) and concentrate to give 2-(t-butyidimethylsilyloxy)-ethylbromide (197 g).

Step 3: Treat the product of Step 1 (57 g) in DMF (500 mL) at −10° C. with NaH (8.6 g, 60% disp. in oil) and stir for 1 h. Add 2-(t-butyidimethylsilyloxy)ethylbromide (51.3 g) and NaI (6.4 g) and stir for 18 h. Add EtOAc (400 mL) and saturated NaCl solution (300 mL). Separate the organic portion, dry ($MgSO_4$), filter and concentrate. Purify the crude oil by silica gel chromatography eluting with EtOAc/hexane mixtures to give product (60.1 g).

Step 4: Treat the product from Step 3 (28 g) with O-allylhydroxylamine HCl (17 g) according to a procedure similar to Example 1, to give the title compound (24.5 g).

EXAMPLE 1

1-[[(3,5-bis(trifluoromethyl)phenyl]methoxy]-3-(3,4-dichlorophenyl)-5-(4-hydroxy-4-phenyl-1-piperidinyl)-2-pentanone O-methyloxime

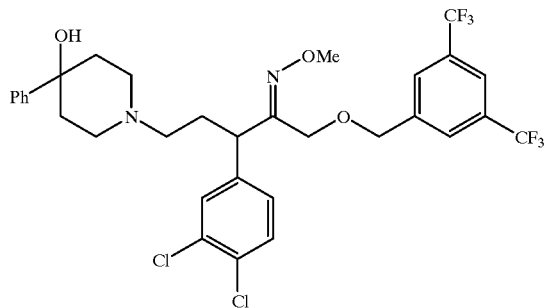

Treat a solution of the product of Preparation 1 (270 mg, 0.417 mmol) in dry pyridine (5 mL) with O-methoxylamine HCl (52 mg, 0.626 mmol, 1.5 eq) and heat to 60° C. for 30 min. Allow the vessel to cool to 23° C. and remove the pyridine in vacuo. Take up the crude product in a minimal amount of $CH_2Cl_2$ (2 mL) and apply to a silica gel column (2.5 cm×15 cm) packed with hexane:EtOAc:triethylamine (66:33:1). Elute with the same solvent system to obtain 190 mg (0.281 mmol, 67%) of the title compound as a colorless foam.

HRMS (FAB, M+H$^+$): m/e calc'd for $[C_{32}H_{33}N_2O_3Cl_2F_6]^+$: 677.1772, found 677.1785.

Example 1 A (Z isomer) is prepared from the product of Preparation 1 in a procedure similar to that described for Example 1, using hydroxyl amine HCl as the starting material:

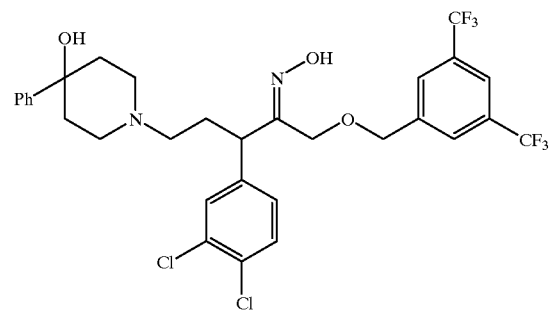

HRMS (FAB, M+H$^+$): calc'd: 663.1616, found 663.1625.

EXAMPLE 2

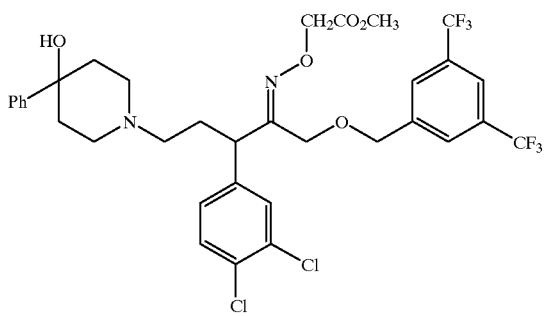

Treat a solution of Example 1A (400 mg, 0.603 mmol) in dry DMF (12 mL) at 0° C. with 60% NaH in mineral oil (48 mg), stir for 40 min and treat with methyl bromoacetate (60 μL, 0.633 mmol, 1.05 eq). Stir for 30 min, pour into EtOAc (250 mL)/half saturated $NaHCO_3$ (200 mL) and extract. Wash the organic layer with water (2×100 mL), then brine (10 mL) and dry over $Na_2SO_4$. Purify the crude mixture by silica gel chromatography (4×15 cm; hex/EtOAc 1:1 we 2% $NEt_3$) to give 361.8 mg (0.492 mmol, 82%) of the pure product as an oil. HRMS (FAB, M+H$^+$): m/e calic'd for $[C_{34}H_{34}Cl_2F_6N_2O_5]^+$: 735.1827, found 735.1839.

Using a similar procedure, treat the product of Example 1A with the appropriate alkyl halide to obtain the following compounds 2A–2C:

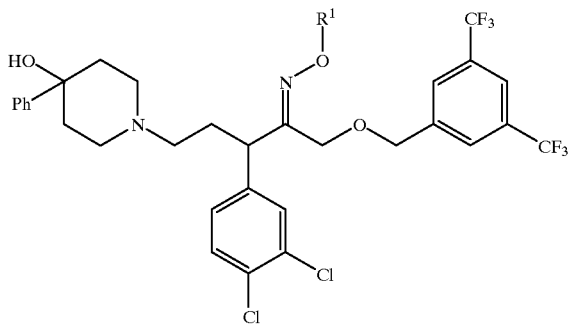

| Ex. | R[1] | Alkyl Halide | HRMS calc'd (FAB, M + H+) | HRMS Found |
|---|---|---|---|---|
| 2A | —CH₂CN | Br-acetonitrile | 702.1725 | 702.1720 |
| 2B | —CH₂CH₂OH | 2-Br-1-(t-Bu-dimethyl-silyloxy)-ethane* | 707.1878 | 707.1856 |
| 2C | —(CH₂)₃-phthalyl | N-(3-Br-propyl)-phthalimide | 850.2249 | 850.2248 |

*Followed by desilylation with 1M TBAF in THF (3 h, 23° C.).

EXAMPLE 3

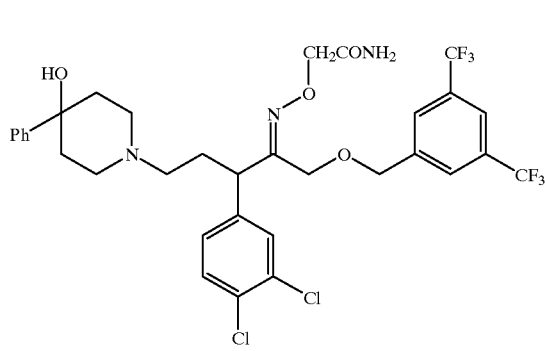

Treat a solution of the product of Example 2 (57 mg, 0.078 mmol) in MeOH (3 mL) at 0° C. with gaseous ammonia for 5 min. After venting 2–3 times, seal the vessel with a polypropylene cap and stir until TLC shows the reaction is complete (20 h) to give (56 mg, 0.078 mmol, >99%) of the pure product as a colorless powder. HRMS (FAB, M+H+): m/e calc'd for $[C_{33}H_{33}Cl_2F_6N_3O_4]^+$: 720.1831, found 720.1841.

EXAMPLE 4

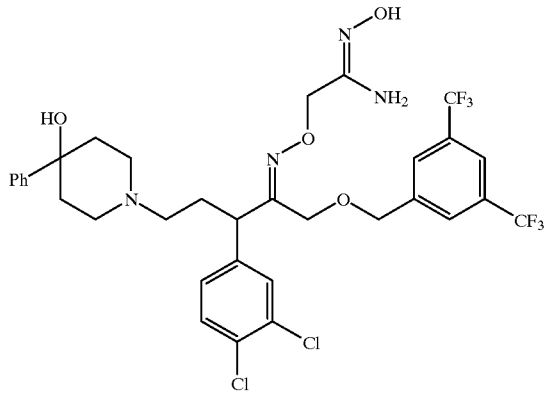

Treat a suspension of H₂NOH•HCl (47 mg, 0.68 mmol, 5 eq) in ethanol with KOH in MeOH (680 L, 0.68 mmol, 5 eq), sonicate for 5 min and then add to a solution of Example 2A (95 mg, 0.135 mmol) in ethanol (5 mL). Heat for 2.5 h at 60° C., filter, concentrate in vacuo and purify by silica gel chromatography (2.5×14 cm; CH₂Cl₂/MeOH (NH₃) 95:5) to give 98.3 mg (0.134 mmol, 99%) of the product as a film. HRMS (FAB): 735.1956 (M+H+).

EXAMPLES 5, 5A AND 5B

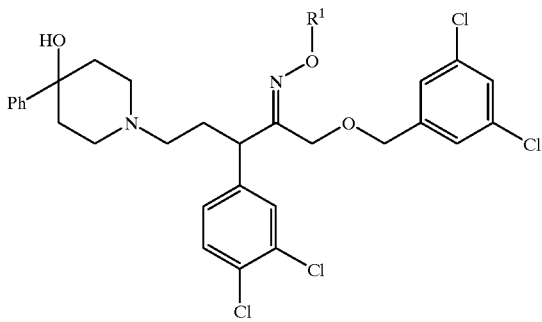

Using the procedures described below, compounds of the structural formula above were prepared, wherein the definitions of $R^1$ are shown in the following table:

| Ex. | $R^1$ | HRMS calc'd (FAB, M + H$^+$) | HRMS Found |
|---|---|---|---|
| 5 | —CH$_2$CN | 634.1198 | 634.1206 |
| 5A | —CH$_2$CH$_2$OH | 639.1351 | 639.1342 |
| 5B | 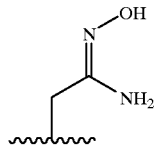 | 667.1351 | 639.1342 |

EXAMPLE 5

Step 1: Prepare the allyl oxime ether of the product of Example 6, Step 7, employing O-allylhydroxylamine HCl as the alkoxyl amine.

Step 2: Remove the silyl protective group in a procedure similar to that described in Example 6, Step 8.

Step 3: Alkylate the hydroxyl group with 3,5-dichlorobenzylbromide in a procedure similar to that in Example 6, Step 9.

Step 4: Treat a solution of the product of step 3 (285 mg, 0.426 mmol) in 80% aqueous EtOH with Pd(PPh$_3$)$_4$ (25 mg, 0.021 mmol, 0.05 eq) and triethylammoniumformate (2.13 mL of 1M solution in THF, 5 eq) and stir at reflux for 4 h. Cool, concentrate and purify by silica gel chromatography (2.5×16.5 cm; hex/EtOAc 1:1 w/2% NEt$_3$) to give 185 mg (0.3095 mmol, 73%) as a film.

Step 5: Treat the product of step 4 in a similar fashion to Example 2, using BrCH$_2$CN as the alkyl halide.

Example 5A: Treat the product of Example 5, step 4, in a similar fashion to Example 2, using 2-bromo-1-(t butyldimethylsiloxy)ethane as the alkyl halide, followed by desilylation (3 h, 23° C.) with 1M TBAF in THF.

Example 5B: Treat the product of Example 5, Step 5, in a similar fashion to Example 4 to obtain the desired product.

EXAMPLE 6

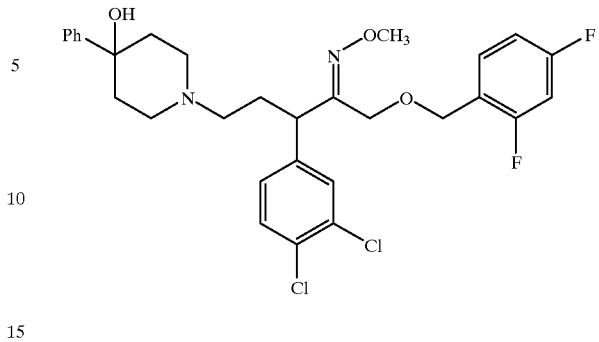

Steps 1–6: Prepare 3-(3,4-dichlorophenyl)-1-[[dimethyl(1,1-dimethyl-ethyl)silyl]oxy]-5-(4-hydroxy-4-phenyl-1-piperidinyl)-2-pentanone as described in U.S. Pat. No. 5,696,267.

Step 7: Treat a solution of the product of Step 6 (6.6 g, 12.3 mmol) and NaOAc (6.05 g, 73.8 mmol) in EtOH (110 mL) and H$_2$O (27 mL) with NH$_2$OCH$_3$•HCl. Stir the resulting solution for 12–18 hours at room temperature. Concentrate under reduced pressure and partition the resulting residue between CH$_2$Cl$_2$ (100 mL) and H$_2$O (100 mL). Extract the aqueous layer with CH$_2$Cl$_2$ (3×100 mL), dry the combined organic layers over MgSO$_4$, filter and concentrate under reduced pressure to yield the crude product as a pale oil. This product is carried on without purification to the next step. HRMS (FAB, M+H$^+$): m/e cal'd for $[C_{29}H_{43}N_2O_3SiCl_2]^+$: 565.2420, found 565.2410.

Step 8: Treat a solution of the crude oxime from Step 7 (≦12.3 mmol) in THF (400 mL) with TBAF (15.4 mL, 15.4 mmol, 1M in THF) at 0° C. Stir the solution for 2 hours. Quench the reaction with water and extract the aqueous phase with EtOAc (3×100 mL). Dry the combined organic layers over MgSO$_4$, filter and concentrate under reduced pressure to give the crude product as a yellow oil. Purify by silica gel chromatography (column: 7.5 cm×20 cm; pack column in CH$_2$Cl$_2$ and elute using a gradient of 100% CH$_2$Cl$_2$ to 5% CH$_3$OH(NH$_3$)/CH$_2$Cl$_2$) to obtain 16 g (29.9 mmol, 75% from Step 6) of the desired compound as a white solid. HRMS (FAB, M+H$^+$): m/e cal'd for $[C_{23}H_{29}N_2O_3Cl_2]^+$: 451.1555, found 451.1553.

Step 9: Treat a solution of the product of Step 8 (200 mg, 0.44 mmol) in DMF at 0° C. with NaH (12 mg, 0.48 mmol). Stir the resulting mixture for 30 mins at 0° C. Add 2,4-difluorobenzylbromide (60 µL, 0.465 mmol) in one portion and remove cooling bath. Stir the reaction for 12–18 hours at room temperature. Quench the reaction with H$_2$O and extract with EtOAC (3×30 mL). Dry the combined organic layers over MgSO$_4$, filter and concentrate under reduced pressure to give the crude compound as a yellow oil. Purify by silica gel chromatography (column: 2.5 cm×15 cm; pack column in 50% EtOAc/Hexane and elute using a gradient of 50–100% EtOAc/Hexane) to obtain 128mg (0.22 mmol, 50% ) of the title compound as a pale oil. HRMS (FAB, M+H$^+$): m/e cal'd for $[C_{30}H_{33}N_2O_3Cl_2F_2]^+$: 577.1836, found 577.1832.

EXAMPLE 7

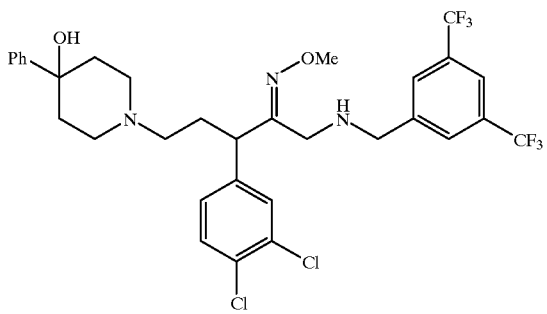

Step 1: Add the product of Example 6, Step 8 (1.8 g) and TFA (0.31 μL) to o iodoxybenzoic acid (2.24 g) in DMSO (20 mL). Stir the mixture for 2 h and add ice/$H_2O$ (50 mL), conc. $NH_4OH$ soln. (5 mL) and EtOAc (50 mL). Stir the mixture and filter to remove solids. Wash the solid residue with $H_2O$ (2×20 mL) and EtOAc (2×20 mL). Combine the filtrates, separate the organic layer and wash with $H_2O$ (2×25 mL), dry over $MgSO_4$, filter and evaporate to give 3-(3,4-dichlorophenyl)-5-(4-hydroxy-4-phenyl-1-piperidinyl)-2-(2-methoxyimino)pentanal (1.8 g) as a foamy solid.

Mass spectrum (FAB): 449.

Step 2: Treat the product of Step 1 (0.2 g) in $CF_3CH_2OH$ (5 mL) with 3 Å molecular sieves (1.0 g) and 3,5-bistrifluoromethylbenzylamine (0.14 g). Stir the mixture for 90 min. and add $NaBH_3CN$(0.12 g). After 18 h. filter the reaction mixture through a pad of Celite, rinse the Celite with MeOH (10 mL) and evaporate the combined filtrates. Partition the residue between $CH_2Cl_2$ (15 mL) and 20% KOH (15 mL). Separate the organic layer and extract the aqueous layer with $CH_2Cl_2$ (2×20 mL). Combine the organic extracts, dry over $MgSO_4$, filter and evaporate to give a solid. Purify the crude by silica gel chromatography eluting with $NH_3$/MeOH/$CH_2Cl_2$ mixtures to give the title compound (0.1 g). HRMS (FAB, M+H$^+$): m/e calc'd for $[C_{32}H_{34}N_3O_6Cl_2F_6]^+$: 676.1932, found 676,1940.

EXAMPLE 7A:

3-(3,4-Dichlorophenyl)-5-(4-hydroxy4-phenyl-1-piperidinyl)-1 -[[(2-methoxyphenyl)methyl]amino]-2-pentanone O-methyloxime.

Using the product of Example 7, Step 1 as starting material, prepare the compound of Example 7A using 2-methoxybenzylamine in a procedure similar to that described in Example 7, Step 2. HRMS (FAB, M+H$^+$): m/e calc'd for $[C_{31}H_{37}N_3O_3Cl_2]^+$: 570.2290, found 570.2291

EXAMPLE 8

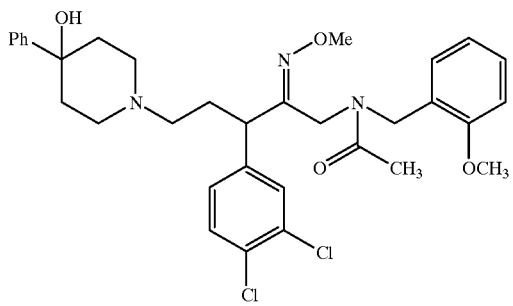

Treat the product of Example 7A (50 mg) in $CH_2Cl_2$ (5 mL) with HOBT (12.4 mg) and AcOH (1 mL) and cool to 0° C. To the cold solution, add DEC (17.6 mg) and stir for a further 18 h. Wash the reaction mixture with 10% $NH_4OH$ soln. (3 mL). Reextract the aqueous layer with $CH_2Cl_2$ (3×3 mL), combine the organic portions, dry over $MgSO_4$, filter and evaporate to give a solid. Purify the crude by by silica gel chromatography eluting with $NH_3$/MeOH/$CH_2Cl_2$ mixtures to give the title compound (0.042 g).

Analysis: Calc'd for $C_{33}H_{39}N_3O_4Cl_2$. $0.5H_2O$; C, 63.76, H, 6.49, N, 6.76. Found: C, 63.83, H, 6.85, N, 6.95.

EXAMPLE 9

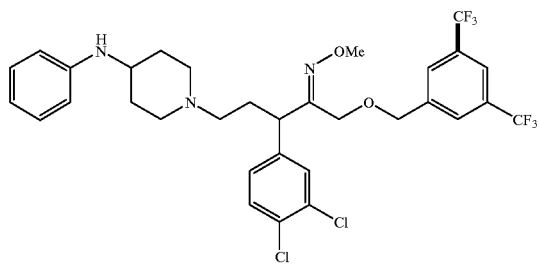

Step 1–7: Prepare 1-[[3,5-bis(trifluoromethyl)phenyl]methoxy]-3-(3,4-dichlorophenyl)-5-hydroxy-2-pentanone O-methyloxime as described in U.S. Pat. No. 5,696,267.

Step 8:

Dissolve oxalyl chloride (2.01 g, 15.82 mmol) in dry $CH_2Cl_2$ (30 mL) and cool to –78° C. under $N_2$, add DMSO (2.47 g, 31.64 mmol) in dry $CH_2Cl_2$ (12 mL) dropwise and stir at –78° C. for 15 mins. Add the product of Step 7 (6.56 g, 12.66 mmol) in dry $CH_2Cl_2$ (20 mL) dropwise and stir at –78° C. for 3 h. Add diisopropylethylamine (4.91 g, 37.97 mmol) and stir at –78° C. for 1 h. Warm slowly to 0° C. and stir at 0° C. for 30 mins. Add water (150 mL) and extract with $CH_2Cl_2$. Wash combined organic extracts with saturated aqueous NaCl, dry ($MgSO_4$), filter, and concentrate to give 6.53 g (12.66 mmol, 100%) of a yellow oil. MS (FAB): m/e 516 (M+1).

Step 9:

Dissolve the product (1.05 g, 2.03 mmol) of Step 8 and 4-phenylamino-piperidine (1.08 g, 6.13 mmol) in $CF_3CH_2OH$ (10 mL), add crushed 3A sieves (1 g) and $NaBH_3CN$(0.26 g, 4.07 mmol), and stir at 23° C. for 4 h. Concentrate and add water (60 mL) and EtOAc (60 mL).

Filter through Celite, separate layers of filtrate and extract aqueous solution with EtOAc. Dry combined organic extracts (MgSO$_4$), filter and concentrate. Purify by chromatography (200 mL of flash silica gel; eluant:3% CH$_3$OH—CH$_2$Cl$_2$). Combine appropriate fractions and concentrate to give 0.98 g (1.45 mmol, 66%) of the title compound as a yellow oil. MS (FAB): m/e 676 (M+1)

The following compound of formula 9A is prepared by reacting the product of Example 9, Step 8, with an appropriate amine according to the procedure of Example 9, Step 9:

9A

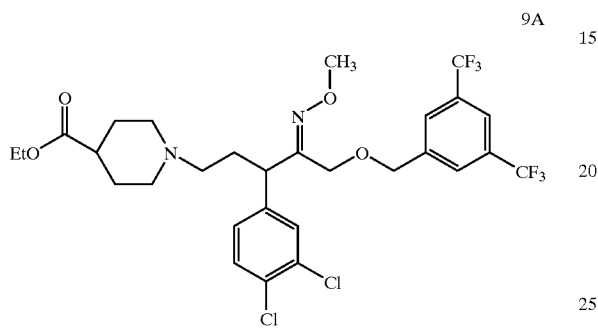

MS(FAB): m/e 657 (M+1)

EXAMPLE 10

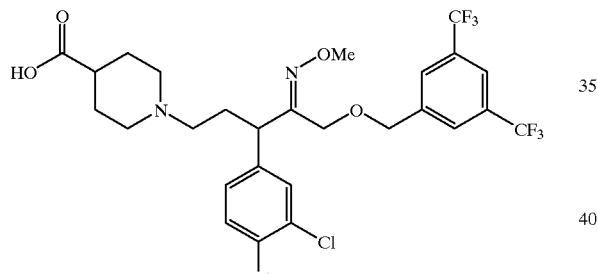

Dissolve the product (0.380 g, 0.578 mmol) of Example 9A in THF (3 mL) and CH$_3$OH (1 mL). Add 1 N KOH (2.7 mL, 2.70 mmol) and reflux for 16 h. Cool to 23° C. and add 1 N HCl (5 mL) and water (20 mL). Extract with CH$_2$Cl$_2$ (3×20 mL), wash combined organic extracts with saturated aqueous NaCl, dry (MgSO$_4$), filter and concentrate to give 0.312 g (0.496 mmol, 86%) of the title compound as a yellow foam. MS (FAB): m/e 629 (M+1)

EXAMPLE 11

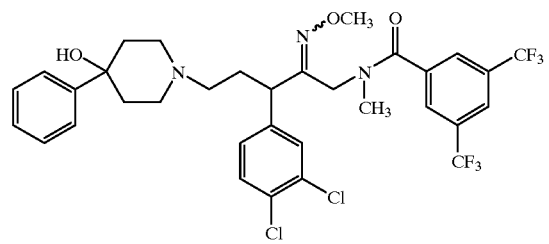

Step 1:

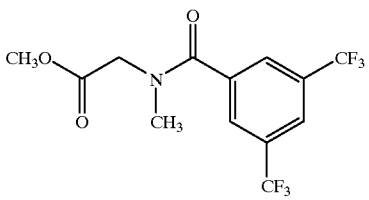

Treat a suspension of sarcosine methyl ester hydrochloride (6.02 g, 43 mmole) in CH$_2$Cl$_2$ (250 ml) at 0° C. with 3,5-bistrifluoromethyl benzoyl chloride (7.7 ml, 42.5 mmole) and Et$_3$N(12.5 ml, 89.7 mmole). Stir the mixture at 20° C. for 1 h. Add water (150 ml) to the mixture and separate the organic layer. Dry (MgSO$_4$) and concentrate the organic layer to give crude product. Purify by silica gel chromatography (eluant: EtOAc:hexane (6:4)) to obtain the product 12 g (81%).

Step 2:

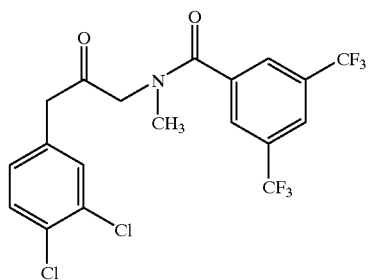

Treat a solution of 3,4-dichlorophenyl acetic acid (4.15 g, 20 mmole) in anhydrous THF (50 ml) at −60° C. with [(CH$_3$)$_3$Si]$_2$NLi (46.2 ml, 46.2 mmole) and slowly warm the mixture to 0° C. for 4h. Transfer this solution to a solution of the product of Step 1 (5.46 g, 16 mmole) in anhydrous THF (8 ml) at −30° C. Warm the reaction to −10° C. over 1 h, stir at 0° C. for 1 h and at 20° C. for 4h. Add 50% of aqueous HOAc (15 ml) and extract with EtOAc. Separate the organic layer, dry (MgSO$_4$) and concentrate to give the crude product. Purifiy by silical gel chromatography (eluant: hexane/EtOAc, 6:4) to give 5.21 g (69%) of the product. HRMS (FAB, M+H$^+$)=mre calc'd for [C$_{19}$H$_{14}$NO$_2$Cl$_2$F$_6$]$^+$= 472.0306, found 472.0306

Step 3:

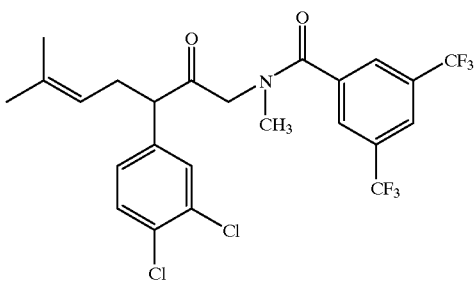

Treat a solution of the product of Step 2 (0.96 g, 2 mmole) in THF (6 ml) at −78° C. with [(CH$_3$)$_3$Si]$_2$NLi (2.5 ml, 2.5 mmole) and stir at −78° C. for 25 h. Add a solution of 1-bromo-3-methyl-2-butene (0.42 g) in THF (1 ml) to the above anion solution at −78° C., slowly warm the solution to 0° C. and stir at 20° C. for 2 h. Add saturated NH$_4$Cl solution (5 ml), extract with EtOAc twice wash the combined EtOAc extracts with brine, dry (MgSO$_4$) and concentrate to give a crude product. Purify by column chromatography (silica gel; eluant: EtOAc:hexane, 2:8) to obtain 1 g of product (87%). MS (FAB, M+H$^+$) m/e 540.

Step 4:

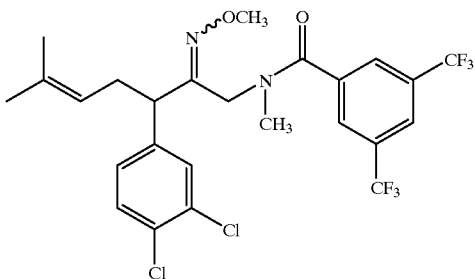

Treat a solution of the product of Step 3 (0.22 g, 0.4 mmole) in pyridine (3 ml) at 70° C. with methoxylamine HCl (95 mg, 1.14 mmole), stir at 70° C. for 6.5 h and then cool to 20° C. Add water to the reaction mixture, extract the solution with EtOAc, dry (MgSO$_4$) and concentrate the EtOAc extracts to give the crude product. Purify by silica gel chromatography (eluant: hexane:Et$_2$O, 1:1) to give 74 mg (32%) of Z-isomer and 130 mg (56%) of E-isomer oximes. MS (FAB, M+H$^+$)=m/e 569.

Step 5A:

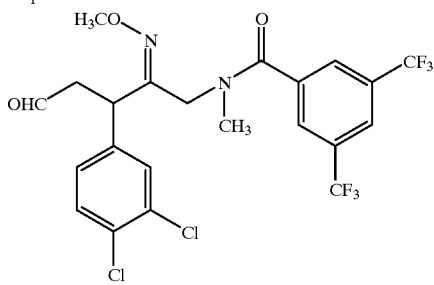

Treat the product of Step 4 (0.387 of E-isomer, 0.68 mmole) in a solution of EtOAc saturated with O$_3$ at −78° C. for 5 min. Purge the solution with N$_2$, add (CH$_3$)$_2$S and warm the solution from −78° C. to 20° C. over 1 h. Concentrate the solution to give the desired aldehyde which is used directly in the next reaction without further purification. MS (FAB.M +H$^+$)=m/e 543.

Step 5B:

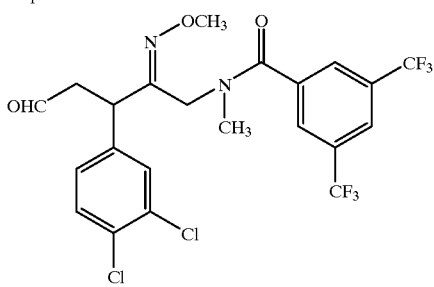

The Z isomer is prepared using a procedure similar to that described in Step 5A employing the Z isomer product of Step 4.

Step 6: Treat the product of Step 5 with 4-hydroxy-4-phenylpiperidine in a procedure similar to that described in Example 9, Step 9, to obtain the title compound (Z isomer) in overall 77% yield. HRMS(FAB,M+H$^+$)=m/e calc'd for [C$_{33}$H$_{34}$N$_3$O$_3$Cl$_2$F$_6$]$^+$:704.1881, found 704.1875.

Example 12

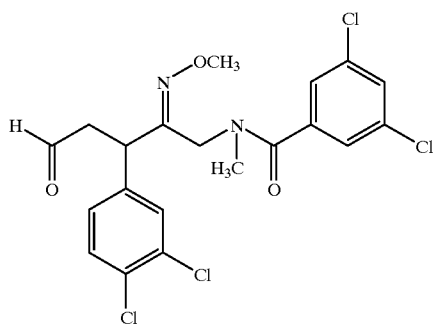

Step 1: Using the procedures of Example 11, substitute 3,5-dichlorobenzoyl chloride in place of 3,5-bistrifluorobenzoyl chloride in Step 1 and proceed through Steps 2, 3, 4 and 5, to obtain the title compound. Alternatively, to prepare optically active material, treat the product of Preparation 6 according to a procedure outlined in Example 13, Step 1.

Step 2: The following compounds of formula 12A to 12S are prepared by reacting the product of Step 1 with an appropriate amine (described in Preparations 3 and 4) according to a procedure similar to Example 9, Step 9. Stereoisomers are separated by HPLC on a chiral column using mixtures of hexane and isopropanol with 0.25% Et$_2$NH added on a Daicel AD and/or OD column.

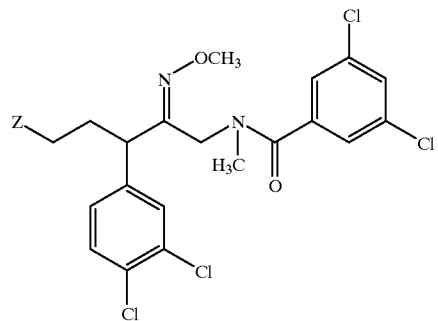
| Example | Z | MS (FAB): m/e |
|---|---|---|
| 12A | 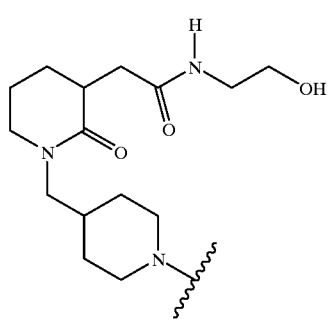 | 758 (M + 1) |
| 12B | 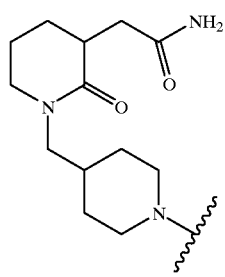 | 714 (M + 1) |
| 12C | 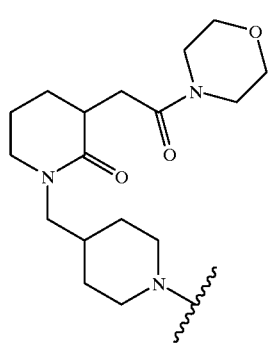 | 784 (M + 1) |

-continued
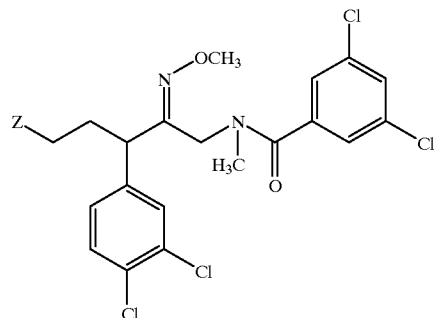
| Example | Z | MS (FAB): m/e |
|---|---|---|
| 12D | 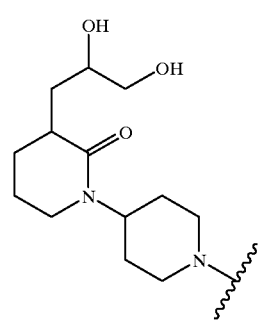 | 717 (M + 1) |
| 12E | 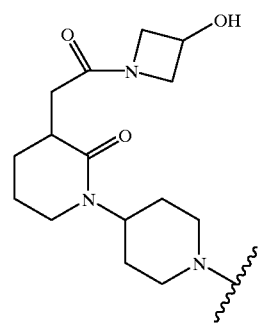 | 756 (M + 1) |
| 12F | 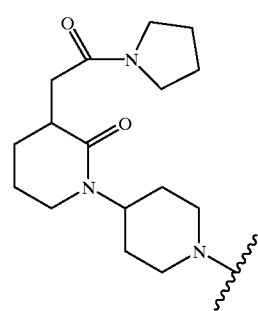 | 755 (M + 1) |
| 12G | 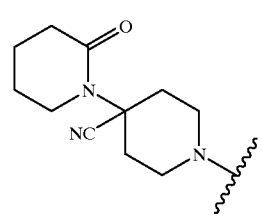 | 668 (M + 1) |

-continued
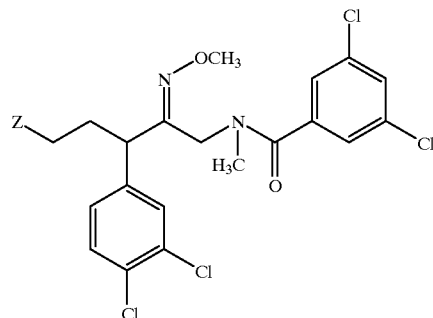
| Example | Z | MS (FAB): m/e |
|---|---|---|
| 12H | 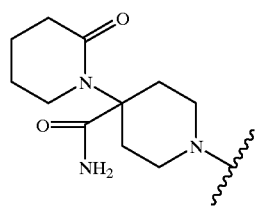 | 668 (M − 17) |
| 12I | 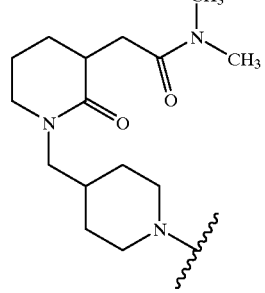 | 742 (M + 1) |
| 12J | 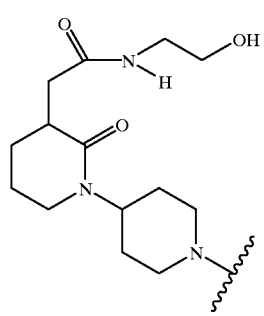 | 744 (M + 1) |
| 12K | 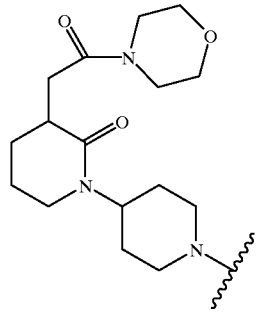 | 770 (M + 1) |

-continued
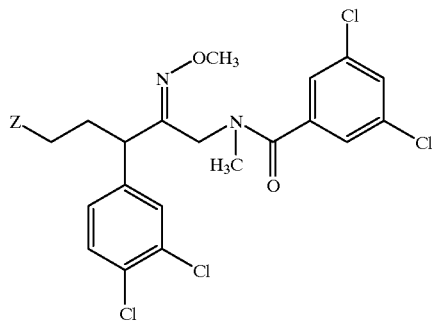
| Example | Z | MS (FAB): m/e |
|---|---|---|
| 12L | (structure with piperidinone, bipiperidine, 4-hydroxypiperidine amide) | 784 (M + 1) |
| 12M | (bipiperidine-piperidinone with N-methoxy amide) | 728 (M + 1) |
| 12N | (4-phenyl-4-hydroxypiperidine) | 636 (M + 1) |
| 12O | (4-phenylpiperidine-4-carbonyl morpholine) | 733 (M + 1) |
| 12P | (bipiperidine-piperidinone with N-methylpiperazine amide) | 783 (M + 1) |
| 12Q | (bipiperidine-piperidinone with thiomorpholine amide) | 786 (M + 1) |

-continued

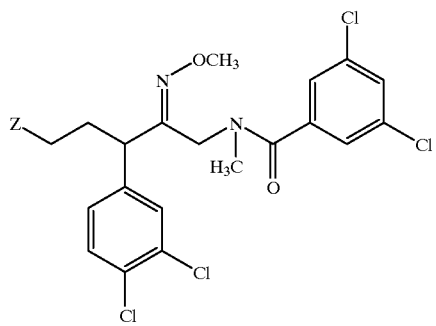

| Example | Z | MS (FAB): m/e |
|---|---|---|
| 12R | 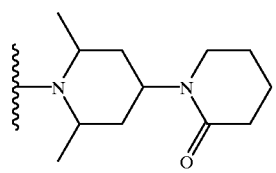 | 669 (M + 1) |

Example 13

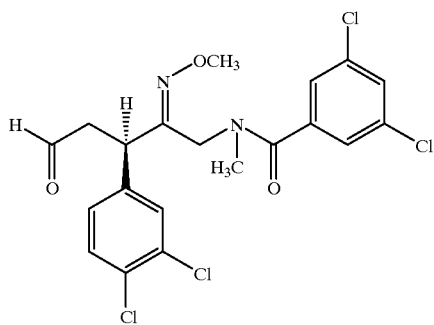

Step 1: Treat the product of Preparation 6 with $CH_3I$ using the procedure of Example 2, followed by a procedure similar to Example 11, Step 5, to obtain the title compound.

Step 2: Prepare the following compounds by reacting the product of Step 1 with an appropriate amine (for 13A to 13C see Preparation 5A–5C, for 13D see Preparation 3O6, for 13F treat the product of Preparation 5, Step 5, using a procedure similar to that described in Preparation 2, Step 4 to give the appropriate amino ester) according to a procedure similar to Example 9, Step 9, substituting $NaB(OAc)_3H$ in place of $NaBH_3CN$ and 1,2-dichloroethane for trifluoroethanol. Prepare 13G by treatment of Example 13D with MCPBA in $CH_2Cl_2$ at 0° C. for 3 h; 13H is similarly prepared by treatment of 13B. Example 13E is prepared from Example 13F using standard saponification conditions similar to those described in Preparation 5, Step 6.

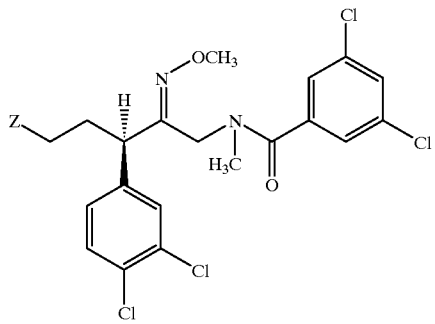

| Ex. | Z | HRMS Found (FAB, M + H+) | Additional Data |
|---|---|---|---|
| 13A | [piperidine-piperidinone-CH2C(O)NMe2] | 726.2145 | $[\alpha]_D^{26} = -41.1°$ (c = 0.6, CH$_2$Cl$_2$) |
| 13B | [piperidine-piperidinone-CH2C(O)NHMe] | 712.1979 | $[\alpha]_D^{26} = -42.1°$ (c = 0.6, CH$_2$Cl$_2$) |
| 13C | [piperidine-piperidinone-CH2C(O)NH2] | 698.1829 | $[\alpha]_D^{26} = -42.2°$ (c = 0.6, CH$_2$Cl$_2$) |
| 13D | [piperidine-piperidinone] | 641.1622 | $[\alpha]_D^{26} = -52.7°$ (c = 0.28, EtOH) |
| 13E | [piperidine-piperidinone-CH2C(O)OH] | 699.1666 | — |
| 13F | [piperidine-piperidinone-CH2C(O)OCH3] | 713.1831 | — |
| 13G | [piperidine N-oxide-piperidinone] | — | MS = 659 (M + 1) |

-continued

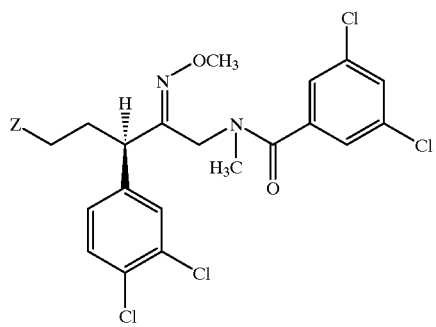

| Ex. | Z | HRMS Found (FAB, M + H⁺) | Additional Data |
|---|---|---|---|
| 13H | 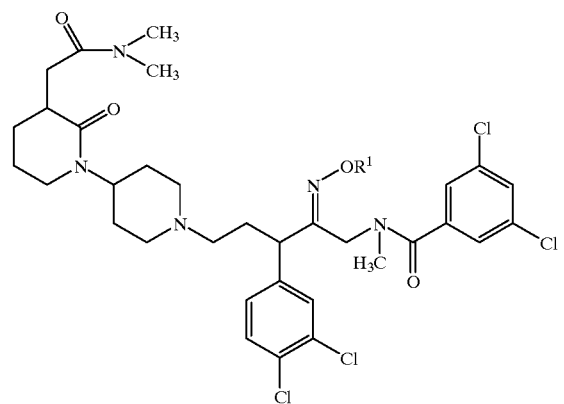 | — | MS = 730 (M + 1) |

EXAMPLE 14

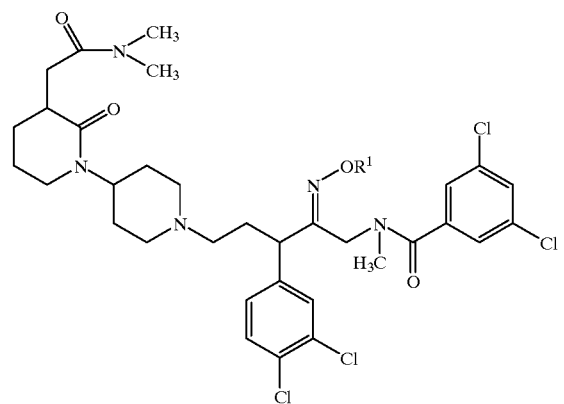

| Example | R1 | MS (FAB): m/e |
|---|---|---|
| 14A | CH₂CH=CH₂ | 754 (M + 1) |
| 14B | H | 714 (M + 1) |
| 14C | CH₂CN | 753 (M + 1) |
| 14D | ⌇—N(OH)—C(NH₂)= | 786 (M + 1) |
| 14E | ⌇—N(OCH₃)—C(NH₂)= | 800 (M + 1) |

Example 14A: Treat the product of Preparation 7 according to a procedure similar to that described in Example 6, Step 8. Proceed in a similar manner as described in Example 9, Steps 8–9, using the product of Preparation 5A or 3A6 in place of 4-phenylamino-piperidine. Proceed in a manner similar to that of Preparation 2, Step 4, optionally substituting HCl for TFA. Acylate the amine according to a procedure similar to Preparation 2, Step 2A, using 3,5 dichlorobenzoyl chloride.

Example 14B: Treat the product of Example 14A using a procedure similar to Example 5, Step 4, to obtain the oxime. Alternatively, for the preparation of optically active material, treat the product of Preparation 6 according to a procedure outlined in Example 11, Step 5B, followed by the procedure of Example 13A, Step 2.

Example 14C: Treat the product of Example 14B with BrCH₂CN according to a procedure similar to Example 2A to give the title compound.

Example 14D: Use a procedure similar to that described in Example 4 using the product of Example 14C to obtain the title compound. The stereoisomers are separated by HPLC on a chiral column using mixtures of hexane and isopropanol with 0.25% Et₂NH added on a Daicel AD and/or OD column.

Example 14E: Treat the product of Example 14C according to a procedure similar to that of Example 18M to obtain the title compound.

EXAMPLE 15

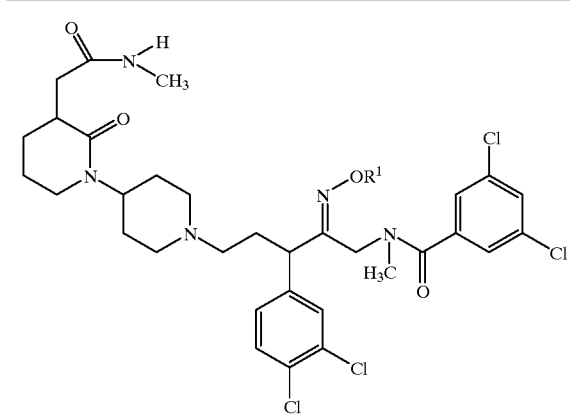

| Example | R1 | MS (FAB): m/e |
|---|---|---|
| 15A | H | 700 (M + 1) |
| 15B | CH$_2$CN | 739 (M + 1) |
| 15C | CH$_2$CH$_2$OH | 744 (M + 1) |
| 15D | ![](structure with C(O)NH$_2$) | 757 (M + 1) |
| 15E | ![](structure with C(O)NHCH$_3$) | 771 (M + 1) |
| 15F | ![](structure with C(=NOH)NH$_2$) | 772 (M + 1) |
| 15G | ![](thiadiazole amide) | 841 (M + 1) |
| 15H | CH$_2$CH$_2$CH$_2$SO$_3$H | 822 (M + 1) |
| 15I | | 796 (M + 1) |
| 15J | | 851 (M + 1) |
| 15K | CH$_2$F | 732 (M + 1) |

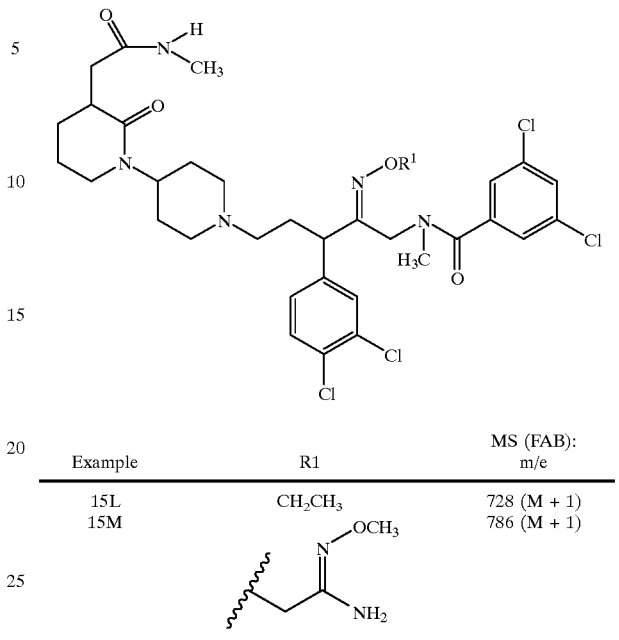

| Example | R1 | MS (FAB): m/e |
|---|---|---|
| 15L | CH$_2$CH$_3$ | 728 (M + 1) |
| 15M | NH$_2$) | 786 (M + 1) |

Example 15A

Step 1: Treat the product of Preparation 7 using a procedure similar to that described in Example 6, Step 8. Proceed in a similar manner as described in Example 9, Steps 8–9, using the product of Preparation 5B or 3B6 in place of 4-phenylamino-piperidine. Proceed in a manner similar to the procedure outlined in Preparation 2, Step 4, optionally substituting HCl for TFA. Acylate the amine according to a procedure similar to Preparation 2, Step 2A, using 3,5 dichlorobenzoyl chloride.

Step 2: Treat the resultant product using a procedure similar to Example 5, Step 4, to obtain the title compound.

Alternatively, for the preparation of optically active material, treat the product of Preparation 6 according to a procedure outlined in Example 11, Step 5, followed by the procedure of Example 13B, Step 2.

Example 15B: Treat the product of Step 2 with BrCH$_2$CN according to a procedure similar to Example 2A to give the title compound.

Example 15C: Alkylate and deprotect the product of Example 15A according to a procedure similar to Example 2B to give the title compound.

Example 15D:

Step 1: Alkylate the product in Example 15A with allylchloroacetate according to a procedure similar to Example 2 to give the resulting allyl ester.

Step 2: Treat a solution of the product of Step 1 according to a procedure similar to that of Example 3 to give the title compound.

Example 15E: Treat a solution of Example 15D, Step 1, with CH$_3$NH$_2$ according to a procedure similar to that of Example 3 to give the title compound.

Example 15F: Use a procedure similar to that described in Example 4 using the product of Example 15B to obtain the title compound. The stereoisomers are separated by HPLC on a chiral column using mixtures of hexane and isopropanol with 0.25% diethylamine added on a Daicel AD and/or OD column.

Example 15G:

Step 1: Deprotect the product of Example 15D, Step 1, using a procedure similar to Example 5, Step 4.

Step 2: Treat a solution of the product of Step 1 (82 mg) in dry CH$_2$Cl$_2$ (1 mL) with NEt$_3$ (41μL), followed by BOP-Cl (36.5 mg). Stir 15 min at 23° C., then add 2-amino-1,3,4-thiadiazole (14 mg). Stir for 2 h, dilute with EtOAc (75 mL) and wash with 10% citric acid followed by H$_2$O, and then by saturated NaHCO$_3$. Dry the organic layers (Na$_2$SO$_4$), filter, concentrate and purify by silica gel chromatography to give the title compound.

Example 15H: Alkylate the product of Example 15A using a procedure similar to that described in Example 2 using 1,3-propane sultone in place of methyl bromoacetate to obtain the title compound.

Example 15I: Couple the product of Example 15G, Step 1, with H$_2$NCH$_2$CN using a procedure similar to that in Example 8 to give the title compound.

Example 15J: Couple the product of Example 15G, Step 1, with H$_2$NCH$_2$SO$_3$H using a procedure similar to that in Example 8 to give the title compound.

Example 15K: Alkylate the product of Example 15A using a procedure similar to that described in Example 2 using BrCH$_2$F in place of methyl bromoacetate to obtain the title compound.

Example 15L: Treat the product of Example 15A with iodoethane according to a procedure similar to Example 2 to give the title compound.

Example 15M: Treat the product of Example 15B according to a procedure similar to that of Example 18M to obtain the title compound.

EXAMPLE 16

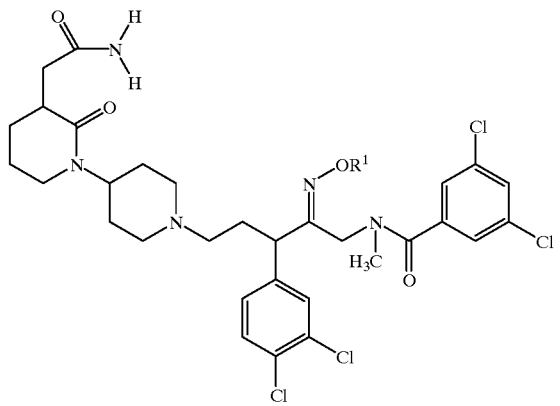

| Example | R1 | Physical Data |
|---|---|---|
| 16A | H | MS = 687 (M + 1) |
| 16B | CH$_2$CN | — |
| 16C | CH$_2$CH$_2$OH | — |
| 16D | 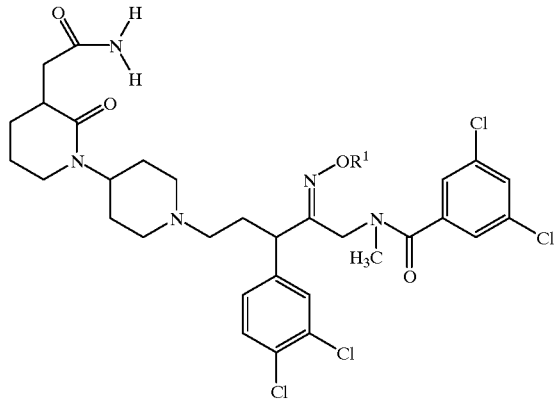 | — |
| 16E | | — |
| 16F | | — |
| 16G | | — |
| 16H | CH$_2$CH$_2$CH$_2$SO$_3$H | — |
| 16I | | — |
| 16J | | — |
| 16K | CH$_2$F | — |
| 16L | CH$_2$CH$_3$ | — |
| 16M | | — |

Example 16A:

Step 1: Treat the product of Preparation 7 using a procedure similar to that described in Example 6, Step 8. Proceed in a similar manner as described in Example 9, Steps 8–9, using the product of Preparation 5C or 3C$_6$ in place of 4-phenylamino-piperidine. Proceed in a manner similar to the procedure outlined in Preparation 2, Step 4, optionally substituting HCl for TFA. Acylate the amine according to a procedure similar to Preparation 2, Step 2A, using 3,5 dichlorobenzoyl chloride.

Step 2: Treat the resultant product using a procedure similar to Example 5, Step 4, to obtain the title compound.

Alternatively, for the preparation of optically active material, treat the product of Preparation 6 according to a procedure outlined in Example 11, Step 5, followed by the procedure of Example 13C, Step 2.

Example 16B: Treat the product of Step 2 with the BrCH$_2$CN according to a procedure similar to Example 2A to give the title compound.

Example 16C: Alkylate and deprotect the product of Example 16A according to a procedure similar to Example 2B to give the title compound.

Example 16D:
Step 1: Alkylate the product in Example 16A with allylchloroacetate according to a procedure similar to Example 2 to give the resulting allyl ester.
Step 2: Treat a solution of the product of Step 2 according to a procedure similar to that of Example 3 to give the title compound.

Example 16E Treat a solution of Example 16D, Step 1, with CH$_3$NH$_2$ according to a procedure similar to that of Example 3 to give the title compound.

Example 16F: Use a procedure similar to that described in Example 4 using the product of Example 16B to obtain the title compound. The stereoisomers are separated by HPLC on a chiral column using mixtures of hexane and isopropanol with 0.25% Et$_2$N added on a Daicel AD and/or OD column.

Example 16G:
Step 1: Deprotect the product of Example 16D, Step 1, using a procedure similar to Example 5, Step 4.
Step 2: Treat the product of Step 1 according to a procedure similar to Example 15G, Step 2, to give the title compound.

Example 16H: Alkylate the product of Example 16A using a procedure similar to that described in Example 2 using 1,3-propane sultone in place of methyl bromoacetate to obtain the title compound.

Example 16I: Couple the product of Example 16G, Step 1, with H$_2$NCH$_2$CN using a procedure similar to that in Example 8 to give the title compound.

Example 16J: Couple the product of Example 16G, Step 1, with H$_2$NCH$_2$SO$_3$H using a procedure similar to that in Example 8 to give the title compound.

Example 16K: Alkylate the product of Example 16A using a procedure similar to that described in Example 2 using BrCH$_2$F in place of methyl bromoacetate to obtain the title compound.

Example 16L: Treat the product of Example 16A, Step 2 with CH$_3$CH$_2$ according to a procedure similar to Example 2 to give the title compound.

Example 16M: Treat the product of Example 16B according to a procedure similar to Example 18M to obtain the title compound.

EXAMPLE 17

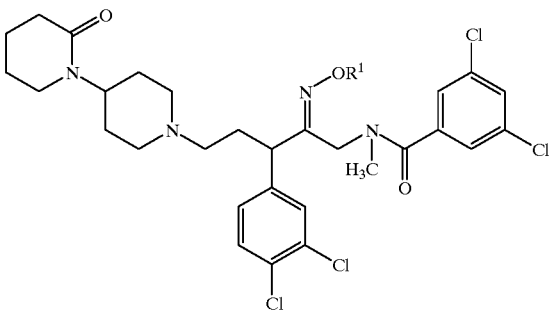

| Example | R1 | HRMS calc'd (FAB, M + H$^+$) | HRMS Found |
|---|---|---|---|
| 17A | H | 627.1463 | 627.1457 |
| 17B | CH$_3$ | 641.1620 | 641.1622 |
| 17C | CH$_2$CH$_2$OH | 671.1725 | 671.1733 |
| 17D | CH$_2$CN | 666.1572 | 666.1591 |
| 17E | (N-OH, NH$_2$) | 699.1787 | 699.1778 |
| 17F | (O, NH$_2$) | 684.1678 | 684.1639 |
| 17G | (O, N(CH$_3$)$_2$) | 712.1991 | 712.1979 |

-continued
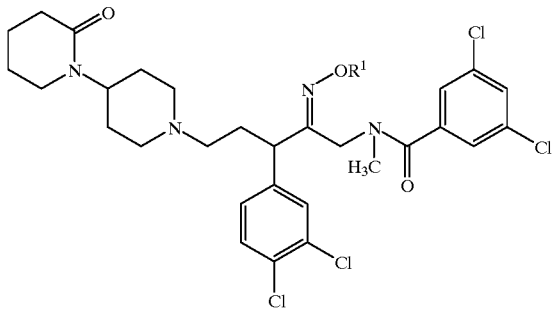
| Example | R1 | HRMS calc'd (FAB, M + H⁺) | HRMS Found |
|---|---|---|---|
| 17H | ![amide NHMe] | 698.1834 | 698.1829 |
| 17I | ![amide-thiadiazole] | 768.1460 | 768.1466 |
| 17J | CH$_2$CH$_2$CH$_2$OH | 685.1882 | 685.1882 |
| 17K | CH$_2$CH$_2$CH$_2$SO$_3^-$NH$_4^+$ | 749.1501 | 749.1508 |
| 17L | ![N-hydroxy amide] | 700.1627 | 700.1618 |
| 17M | ![methylurea] | 741.2256 | 741.2263 |
| 17N | ![methylsulfonyl butyl] | 747.1708 | 747.1716 |
| 17O | ![methylsulfonyl propyl] | 733.1552 | 733.1553 |
| 17P | ![methylsulfinyl butyl] | 731.1759 | 731.1754 |
| 17Q | ![N-methoxy amide] | 714.1784 | 714.1795 |

-continued

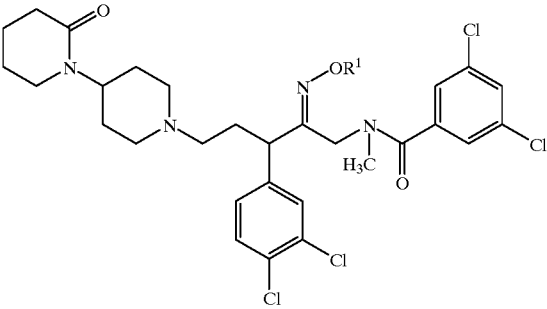

| Example | R1 | HRMS calc'd (FAB, M + H⁺) | HRMS Found |
|---|---|---|---|
| 17R | ![structure with OCH3, N-OCH3, H] | 728.1940 | 728.1953 |
| 17S | CH$_2$F | 659.1526 | 659.1520 |
| 17T | ![structure with OCH3, NH2] | | |

Example 17A:
Step 1: Treat the product of Preparation 7 using a procedure similar to that described in Example 6, Step 8. Proceed in a similar manner as described in Example 9, Steps 8–9, using the product of Preparation 306 in place of 4-phenylamino-piperidine. Proceed in a manner similar to the procedure outlined in Preparation 2, Step 4, optionally substituting HCl for TFA. Acylate the amine according to a procedure similar to Preparation 2, Step 2A, using 3,5 dichlorobenzoyl chloride.
Step 2: Treat the resultant product using a procedure similar to Example 5, Step 4, to obtain the title compound.

Alternatively, for the preparation of optically active material, treat the product of Preparation 6 according to a procedure outlined in Example 11, Step 5, followed by the procedure of Example 13D, Step 2.

Example 17B: Alkylate Example 17A with CH$_3$1 according to a procedure similar to Example 2 to give the title compound.

Example 17C: Alkylate and deprotect the product of Example 17A according to a procedure similar to Example 2B to give the title compound.

Example 17D: Alkylate Example 17A with BrCH$_2$CN according to a procedure similar to Example 2A to give the title compound.

Example 17E: Use a procedure similar to that described in Example 4, using the product of 1 7D to obtain the title compound.

Example 17F:
Step 1: Alkylate Example 17A with allylchloroacetate according to a procedure similar to Example 2 to give the resulting allyl ester.
Step 2: Treat a solution of the product of Step 1 according to a procedure similar to that of Example 3 to give the title compound.

Example 17G: Treat a solution of Example 17F, Step 1, with (CH$_3$)$_2$NH according to a procedure similar to that of Example 3 to give the title compound.

Example 17H: Treat a solution of Example 17F, Step 1, with CH$_3$NH$_2$ according to a procedure similar to that of Example 3 to give the title compound.

Example 17I:
Step 1: Deprotect the product of Example 1 7F, Step 1, using a procedure similar to Example 5, Step 4.
Step 2: Treat the product of Step 1 according to a procedure similar to Example 15G, Step 2, to give the title compound.

Example 17J: Alkylate Example 17A with 3-bromo-1-t-butyidimethylsilyloxy propane and deprotect using a procedure similar to that described in Example 2B to obtain the title compound.

Example 17K: Alkylate Example 17A using a procedure similar to that described in Example 2 using 1,3-propane sultone in place of methyl bromoacetate to obtain the title compound.

Example 17L:
Step 1: Alkylate the product of Example 17A with methyl bromoacetate using a procedure similar to that described in Example 2 to obtain the methyl ester.
Step 2. Treat the product of Step 1 according to a procedure similar to that in Example 4 to give the title compound.

Example 17M:
Step 1: Alkylate the product of Example 17A with bromopropylphthalimide using a procedure similar to that described in Example 2C to obtain the protected propylamine.
Step 2. Treat the product of Step 1 with (CH$_3$)NH$_2$ according to a procedure similar to that in Example 3 to give the primary amine.
Step 3: Treat the product of Step 2 (150 mg) in CH$_2$Cl$_2$ (3 mL) with methyl isocyanate (14.7 mg) and stir for 1 h.

Evaporate the solvent and purify by silica gel chromatography using $CH_2Cl_2/CH_3OH$ saturated with ammonia to provide 137 mg (86%) of the title compound.

Example 17N:

Step 1: Cool a solution of Example 17J (1.0 g) in $CH_2Cl_2$ (20 mL) and then treat with $NEt_3$ (507 µL) and mesyl chloride (170 µL). Warm the solution to 0° C. and stirr for 30 min. Pour into $EtOAc/NaHCO_3$. Wash the organic layer with $H_2O$, brine and dry $(Na_2SO_4)$. Remove the solvent to provide the mesylate (quantitative).

Step 2: Treat a solution of the product of Step 1 in dry DMF with $NaSCH_3$. Stir the solution for 45 min, then pour the mixture into into $EtOAc$/aqueous $NaHCO_3$. Wash the organic layer with $H_2O$ and brine, dry $(Na_2SO_4)$ and purify by silica gel chromatography using $EtOAc/NEt_3$ to provide 282 mg (86%) of the methyl sulfide.

Step 3: Dissolve the product of Step 2 (64 mg) in THF (2 mL) and treat with t-butanol (500 µL), osmium tetroxide (56 µL of 2.5% solution in t-butanol), and NMO (31.6 mg) and stir the mixture for 2 h at 23° C. Pour the mixture into into $EtOAc$/aqueous $NaHSO_4$. Wash the organic layer with saturated aqueous $NaHCO_3$ and brine, dry $(Na_2SO_4)$, filter, concentrate and purify by silica gel chromatography using $EtOAc/NEt_3$ to provide 57 mg (85%) of the title compound.

Example 17O: Alkylate and deprotect the product of Example 17A according to a procedure similar to Example 17J substituting 2-bromo-1-t-butyidimethylsilyloxy ethane for 3-bromo-1-t-butyidimethylsilyloxy propane. Convert the product to the methyl sulfone according to a procedure similar to that described in Example 17N.

Example 17P: Dissolve the product of Example 17N Step 2 (128 mg) in $CH_2Cl_2$ (5 mL) and treat with $ReOCl_3(PPh_3)_4$ (7.5 mg) and phenyl sulfoxide (51 mg). Stir for 3 h at 23° C., then add $ReOCl_3(PPh_3)_4$ (7.5 mg) and phenyl sulfoxide (51 mg) and stir at 23° C. for 15 h. Add $H_2O$ (20 mL) and extract with $CH_2Cl_2$. Dry the organic layer with $MgSO_4$ and concentrate. Purify using silica gel chromatography ($EtOAc/NEt_3/CH_3OH$ as eluant) to provide 95 mg (72%) of the title compound.

Example 17Q: Alkylate the product of Example 17A with the product of Example 18L, Step 2, using a procedure similar to that described in Example 18L, Step 3, to obtain the title compound.

Example 17R: Treat the product of Example 17L with excess diazomethane in $Et_2O$ to obtain the title compound.

Example 17S: Alkylate the product of Example 17A using a procedure similar to that described in Example 2 using $BrCH_2F$ in place of methyl bromoacetate to obtain the title compound.

Example 17T: Treat the product of Example 17D according to a procedure similar to that of Example 18M to obtain the title compound.

EXAMPLE 18

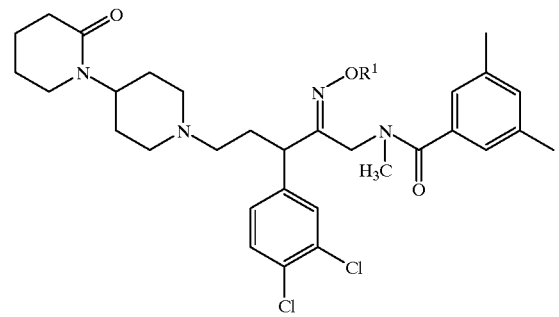

| Example | $R^1$ | MS (FAB): m/e |
|---|---|---|
| 18A | H | 587 (M + 1) |
| 18B | $CH_3$ | 601 (M + 1) |
| 18C | $CH_2CH_2OH$ | 631 (M + 1) |
| 18D | $CH_2CN$ | 626 (M + 1) |
| 18E | [structure with N-OH and NH2] | 659 (M + 1) |
| 18F | [structure with amide and thiadiazole] | 728 (M + 1) |
| 18G | $CH_2CH_2CH_2OH$ | 645 (M + 1) |
| 18H | [structure with morpholine amide] | 714 (M + 1) |
| 18I | [structure with N-methylpiperazine amide] | 728 (M + 1) |
| 18J | [structure with thiomorpholine amide] | 730 (M + 1) |
| 18K | [structure with thiazole amide] | 727 (M + 1) |

-continued

| Example | R¹ | MS (FAB): m/e |
|---------|----|----|
| 18L | (acetamide with N-OMe group) | 674 (M + 1) |
| 18M | (amidine with N-OMe and NH₂) | 673 (M + 1) |
| 18N | (ethyl carbamate with NHMe) | 688 (M + 1) |

Example 18A:

Step 1: Treat the product of Preparation 7 using a procedure similar to that described in Example 6, Step 8. Proceed in a similar manner as described in Example 9, Steps 8–9, using the product of Preparation 306 in place of 4-phenylaminopiperidine. Proceed in a manner similar to the procedure outlined in Preparation 2, Step 4, optionally substituting HCl for TFA. Acylate the amine according to a procedure similar to Preparation 2, Step 2A, using 3,5-dimethylbenzoyl chloride.

Step 2: Treat the resultant product using a procedure similar to Example 5, Step 4, to obtain the title compound.

Alternatively, for the preparation of optically active material, treat the product derived from a procedure similar to that of Preparation 6, Steps 1 and 2, substituting 3,5-dimethylbenzoyl chloride for 3,5-dichlorobenzoyl chloride in Step 1 and resolving the product of Step 2 in a procedure similar to that described in Preparation 6, Step 4B. Continue with the procedure outlined in Example 11, Step 5, followed by the procedure of Example 13D, Step 2.

Example 18B: Alkylate Example 18A with CH₃ according to a procedure similar to Example 2 to give the title compound.

Example 18C: Alkylate and deprotect the product of Example 18A using a procedure similar to Example 2B to give the title compound.

Example 18D: Alkylate Example 18A with BrCH₂CN according to a procedure similar to Example 2A to give the title compound.

Example 18E: Use a procedure similar to that described in Example 4 using the product of 18D to obtain the title compound.

Example 18F:

Step 1: Alkylate Example 18A with allylchloroacetate according to a procedure similar to Example 2 to give the allyl ester.

Step 2: Deprotect the product of Step 1 using a procedure similar to Example 5, Step 4.

Step 3: Couple the product of Step 2 with 2-amino-1,3,4-thiadiazole using a procedure similar to Example 15G, Step 2 to give the title compound.

Example 18G: Alkylate Example 18A with 3-bromo-1-t-butyldimethylsilyloxy propane and deprotect using a procedure similar to that described in Example 2B to obtain the title compound.

Example 18H: Treat the product of Example 18F, Step 1, with morpholine at 65° C. using a procedure similar to that in Example 3 to give the title compound.

Example 18I: Treat the product of Example 18F, Step 1, at 23° C. with n-methylpiperazine using a procedure similar to that in Example 3 to give the title compound.

Example 18J: Couple the product of Example 18F, Step 2, with thiomorpholine using a procedure similar to that in Example 8 to give the title compound.

Example 18K: Couple the product of Example 18F, Step 2, with 2-aminothiazole using a procedure similar to that in Example 18F, Step 3, to give the title compound.

Example 18L:

Step 1: Treat a solution of CH₃ONH₂•HCl (2.5g) in H₂O (40 mL) with NaHCO₃ (5g). Cool to 0° C. and add a solution of ClCH₂COCl (2.4 mL) in THF (20 mL) at a rate to maintain the internal temperature at 0–3° C. Upon complete addition, warm to 23° C. and stir for 2 h. Adjust pH to 5 (Na₂CO₃), remove THF in vacuo, add NaCl and extract with CH₂Cl₂. Dry the organic layer (Na₂SO₄), filter and concentrate to give the α-chloroamide.

Step 2: Treat a solution of the product of Step 1 (131 mg) in acetone (1 mL) with NaI (158 mg). Stir for 7 h at 23° C., remove the solvent in vacuo, redissolve in THF, filter through Celite and concentrate to give the iodo-amide.

Step 3: Alkylate Example 18A with the product of Example 18L, Step 2, using a procedure similar to that described in Example 2 using 2.5 eq. of NaH to obtain the title compound.

Example 18M: Use a procedure similar to that described in Example 4 using the product of 18D and the following modifications: substitute CH₃ONH₂•HCl for HONH₂•HCl, use 2,2,2-trifluoroethanol as the solvent, and stir at 70° C. for 1 week to obtain the title compound.

Example 18N: Treat the product of 18C according to a procedure similar to Example 17M, Step 3.

EXAMPLE 19

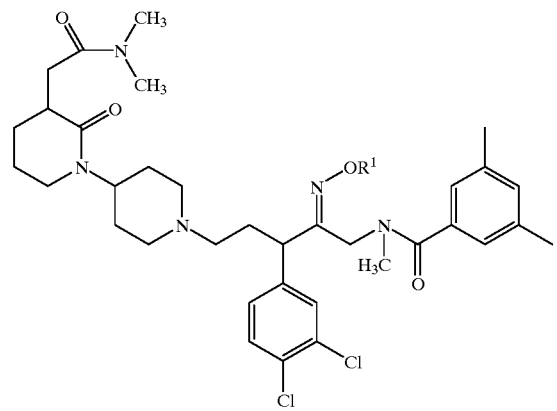

| Example | R1 | MS (FAB): m/e |
|---|---|---|
| 19A | H | 672 (M + 1) |
| 19B | CH₂CN | 711 (M + 1) |
| 19C | ⸺CH₂C(=NOH)NH₂ | 744 (M + 1) |
| 19D | ⸺CH₂C(=O)NH-(1,3,4-thiadiazol-2-yl) | 813 (M + 1) |
| 19E | ⸺CH₂C(=O)NH-OMe | 759 (M + 1) |

Example 19A:
Step 1: Treat the product of Preparation 7 using a procedure similar to that described in Example 6, Step 8. Proceed in a similar manner to Example 9, Steps 8–9, using the product of Preparation 5A or 3A6 in place of 4-phenylamino-piperidine. Proceed in a manner similar to the procedure outlined in Preparation 2, Step 4, optionally substituting HCl for TFA. Acylate the amine according to a procedure similar to Preparation 2, Step 2A, using 3,5-dimethylbenzoyl chloride.
Step 2: Treat the product of Step 1 using a procedure similar to Example 5, Step 4, to obtain the title compound.

Alternatively, for the preparation of optically active material, treat the product derived from a procedure similar to that of Preparation 6, Steps 1 and 2, substituting 3,5-dimethylbenzoyl chloride for 3,5-dichlorobenzoyl chloride in Step 1 and resolving the product of Step 2 in a procedure similar to that described in Preparation 6, Step 4B. Continue with the procedure outlined in Example 11, Step 5, followed by the procedure of Example 13A, Step 2.

Example 19B: Alkylate the product in Example 19A with BrCH₂CN using a procedure similar to Example 2A to give the title compound.

Example 19C: Use a procedure similar to that described in Example 4 using the product of Example 19B to obtain the title compound.

Example 19D:
Step 1: Alkylate the product in Example 19A with allylchloroacetate according to a procedure similar to Example 2 to give the allyl ester.
Step 2: Treat the product of Step 1 using a procedure similar to Example 5, Step 4.
Step 3: Couple the product of Step 2 with 2-amino-1,3,4-thiadiazole according to a procedure similar to Example 15G, Step 2, to give the title compound.

Example 19E: Alkylate the product of Example 19A with the product of
Example 18L, Step 2, using a procedure similar to that described in Example 2 using 2.5 eq. of NaH to obtain the title commpound.

EXAMPLE 20

| Example | R¹ | MS (FAB): m/e |
|---|---|---|
| 20A | ⸺CH₂C(=NOH)NH₂ | 686 (M + 1) |
| 20B | CH₂CH₂OH | 658 (M + 1) |

Example 20A:
Step 1: Treat the product of Preparation 7 using a procedure similar to that described in Example 6, Step 8. Proceed in a similar manner to Example 9, Steps 8–9, using 4-hydroxy-4-phenylpiperidine in place of 4-phenylamino-piperidine. Proceed in a manner similar to the procedure of Preparation 2, Step 4, optionally substituting HCl for TFA. Acylate the amine according to a procedure similar to Preparation 2, Step 2A, using 3,5-dimethyoxybenzoyl chloride.
Step 2: Treat the product of Step 1 using a procedure similar to Example 5, Step 4.
Step 3: Alkylate the product of Step 2 with BrCH₂CN according to a procedure similar to Example 2A to give the title compound.
Step 4: Use a procedure similar to that described in Example 4 using the product of Step 3 to obtain the title compound.

Example 20B: Alkylate the product of Example 20A, Step 2 with 2-bromo-1-t-butyldimethylsilyloxy ethane and deprotect using a procedure similar to that described in Example 2B to obtain the title compound.

EXAMPLE 21

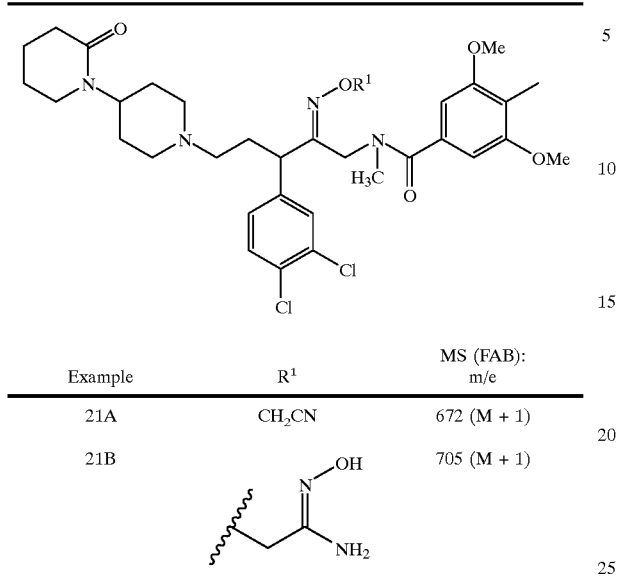

| Example | R¹ | MS (FAB): m/e |
|---------|-----|---------------|
| 21A | CH₂CN | 672 (M + 1) |
| 21B | ![structure](N-OH, NH₂) | 705 (M + 1) |

Example 21A:
Step 1: Treat the product of Preparation 7 using a procedure similar to that described in Example 6, Step 8. Proceed in a similar manner as described in Example 9, Steps 8–9, using the product of Preparation 306 in place of 4-phenylamino-piperidine. Proceed in a manner similar to the procedure outlined in Preparation 2, Step 4, optionally substituting HCl for TFA. Acylate the amine according to a procedure similar to Preparation 2, Step 2A, using 4-methyl-3,5-dimethoxybenzoyl chloride.
Step 2: Treat the product of Step 1 using a procedure similar to Example 5, Step 4.
Step 3: Alkylate the product of Step 2 with BrCH₂CN using a procedure similar to Example 2A to give the title compound.
Example 21B: Treat the product of Example 21A using a procedure similar to that described in Example 4 to obtain the title compound.

EXAMPLE 22

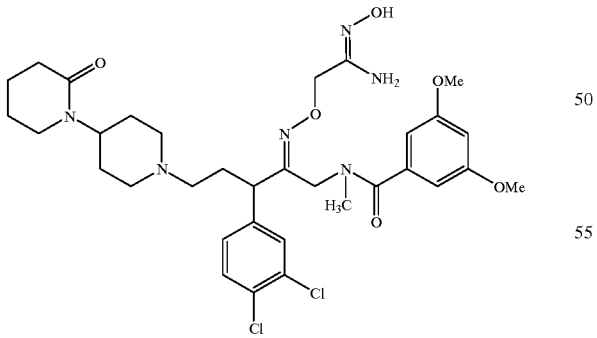

Use a procedure similar to that described in Example 20A using the product of Preparation 306 in place of 4-hydroxy-4-phenylpiperidine in Step 1 to obtain the title compound. HRMS (FAB, M+H⁺): m/e calc'd: 691.2778, found 691.2769.

EXAMPLE 23

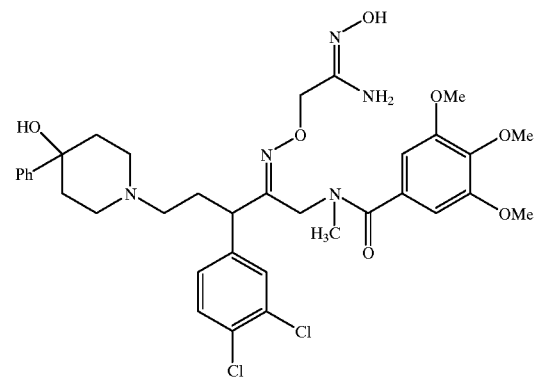

Use a procedure similar to that described in Example 20A using 3,4,5-trimethoxybenzoyl chloride as the acid chloride in Step 1 to obtain the title compound; MS (FAB): m/e 716 (M+1).

EXAMPLE 24

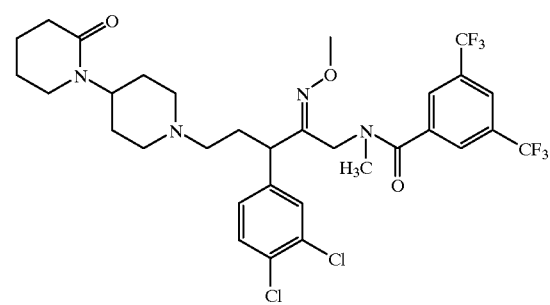

Use a procedure similar to that described in Example 11, using the product of Preparation 306 as the amine in Step 6 to obtain the title compound. HRMS (FAB, M+H⁺): m/e calc'd: 709.2147 found 709.2138.

EXAMPLE 25

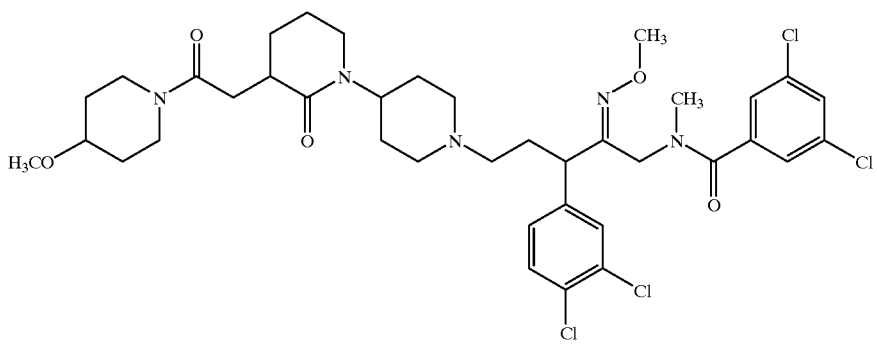

Using a procedure similar to that of Example 2, methylate product of Example 3H5, replacing methyliodide with methylbromoacetate. Deprotect the resulting product and couple to the product of Example 12, Step 1, using the proccedure of Example 9, Step 9, to obtain the title compound. HRMS (FAB, M+H+): m/e calc'd: 798.2537; found 798.2538.

EXAMPLE 26

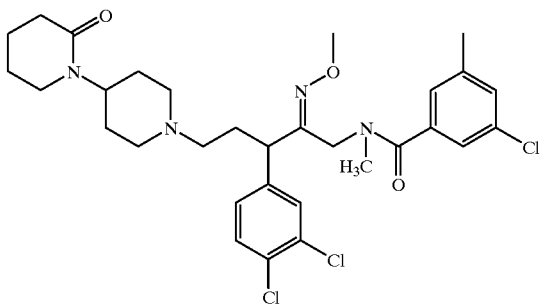

Use a procedure similar to that described in Example 17B using 3-chloro-5-methyl-benzoyl chloride instead of 3,5-dichlorobenzoyl chloride (Step 1, Example 17A) to obtain the title compound. HRMS (FAB, M+H+): m/e calc'd: 621.2166, found 621.2178

EXAMPLE 27

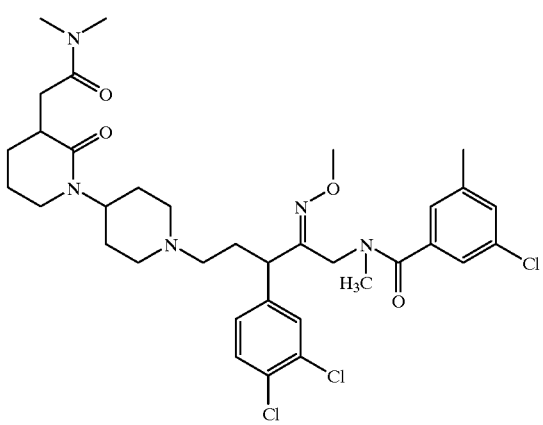

Use a procedure similar to that described in Example 13A using 3-chloro-5-methyl-benzoyl chloride instead of 3,5-dichlorobenzoyl chloride to obtain the title compound. HRMS (FAB, M+H+): m/e calc'd: 706.2694, found 706.2701

EXAMPLE 28

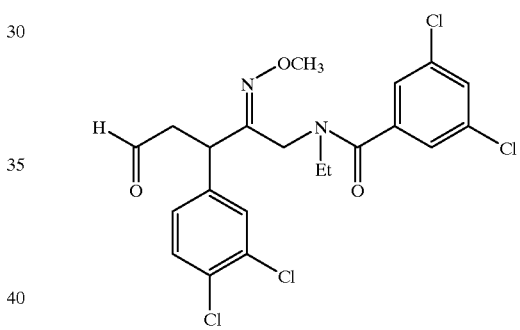

Step 1: Condense glycine with 3,5-dichlorobenzoic acid according to a procedure similar to Example 8. Treat the resulting amide with NaH followed by iodoethane according to Example 2. Treat the resulting material with diazomethane to give N-ethyl-N-(3,5-dichlorobenzoyl)glycine methyl ester.

Step 2: Using the procedures of Example 11, Steps, 2–5, substituting the product of Step 1 for the product of Example 11, Step 1. Optically active material may be prepared using procedures similar to Preparation 6.

The following compounds are prepared by reacting the product of

Step 2 with an appropriate amine (for 28A to 28C, see Preparation 5A–5C; for 28D, see Preparation 3O6) according to a procedure similar to Example 9, Step 9, substituting NaB(OAc)$_3$H for NaBH$_3$CN and optionally substituting 1,2-dichloroethane for 2,2,2-trifluoroethanol.

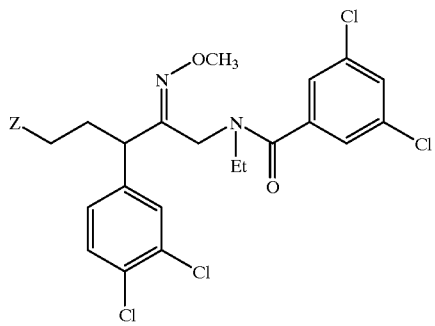

| Example | Z | Data |
|---|---|---|
| 28A | [piperidine-piperidinone-CH2-C(O)NMe2] | — |
| 28B | [piperidine-piperidinone-CH2-C(O)NHMe] | MS (FAB): m/e 728 (M + 1) |
| 28C | [piperidine-piperidinone-CH2-C(O)NH2] | HRMS: calc'd: 712.1991 found: 712.1986 |
| 28D | [piperidine-piperidinone] | — |

EXAMPLE 29

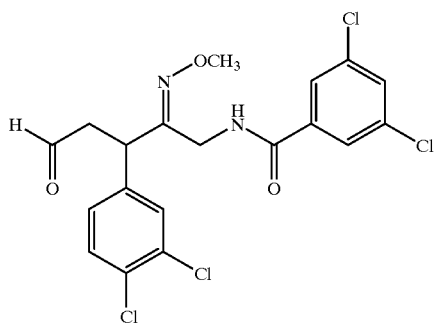

Step 1: Add carbonyldiimidazole (24 g) to a solution of allyl-3,4-dichlorophenyl acetic acid (30.6 g) in anhydrous THF (600 mL). Stir the reaction mixture at 23° C. for 1 hr. In a separate flask, under $N_2$, dissolve potassium t-butoxide (16.8 g) in anhydrous THF (425 mL). Cool the solution to 0° C. and add $CH_3NO_2$ (200 mL) over 30 min. Add the acyl imidazole solution to the potassium nitronate solution via addition funnel while keeping the internal temperature between 0° C. and 5° C. Remove the cooling bath and stir at 23° C. for 2 days. Cool the reaction mixture to 0° C. and pour into cold 1 M HCl (500 mL). Separate the organic layer, dry ($MgSO_4$) and concentrate to give 34 g of orange oil. MS (Cl+/$CH_4$) m/e 288 (M+1).

Step 2: Cool a solution of the product of Step 1 (12.2 g) in THF (34 mL) and HOAc (34 mL) to 0° C. and add $H_2O$ (17 mL). Add powdered Zn (15.6 g) in portions over 15 min. Stir the reaction mixture 15 mmn at 0° C. then warm to 23° C. Heat the reaction mixture to 40° C. for 3 min. Remove the heat and pour into $H_2O$ (150 mL) and THF (100 mL). Filter the mixture and wash the solids with THF and $H_2O$. Concentrate the filtrate and wash the resulting orange material with $Et_2O$ and $CH_2Cl_2$. Concentrate the filtrate to give 15.5 g orange oil. MS (Cl +/$CH_4$) m/e 259 (M+1).

Step 3: Cool a solution of the product of Step 2 (15.5 g) in THF (55 mL) and $H_2O$ (10 mL) to 0° C. and add 3,5-dichlorobenzoyl chloride (8.2 g), Hunig's base (12 mL) and DMAP (0.25 g). Warm the reaction mixture to 23° C. and stir for 16 h. Add EtOAc (300 mL) and wash with $H_2O$ (30 mL ), 1 M HCl (3×30 mL ), $H_2O$ (2×30 mL) and brine (2×40 mL), dry ($MgSO_4$), and concentrate. Purify ($SiO_2$; elute with gradient of 4% EtOAc/hexanes to 25% EtOAc/hexanes) to give 8.8 g of a solid. MS (Cl+/$CH_4$) m/e 432 (M+1).

Step 4: Treat a solution of the product of Step 3 (5.7 g, 13 mmol) in EtOH (100 mL) and H₂O (25 mL) with CH₃ONH₂•HCl (5.54 g, 66.3 mmol) and stir at 23° C. for 2 days. Concentrate the mixture and add EtOAc (200 mL) and H₂O (20 mL). Separate the layers and wash the organic layer with 1 M NaHCO₃ (2×20 mL) and brine (20 mL), dry (MgSO₄) and concentrate to an oil. Purify (SiO₂; elute with a gradient of 4% EtOAc/hexanes to 15% EtOAc/hexanes to give 1.8 g of clear oil. MS (Cl+/CH4) m/e 461 (M+1)

Step 5: Treat the product of Step 4 according to a procedure similar to Example 11, Step 5, to obtain the title compound. MS (FAB): m/e 464 (M+1).

The following compounds of formula 29A to 29D are prepared by reacting the product of Step 5 with an appropriate amine (for 29A to 29C, see Preparation 5A–5C; for 29D, see Preparation 3O6) according to a procedure similar to Example 9, Step 9.

EXAMPLE 30

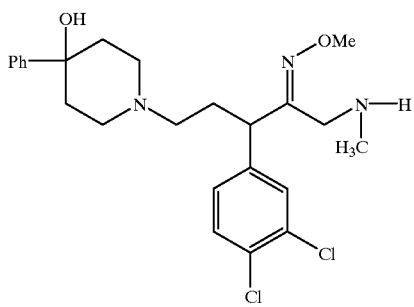

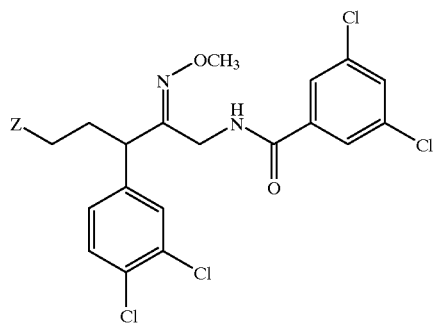

| Example | Z | MS (FAB): m/e |
|---|---|---|
| 29A | (piperidine-piperidinone-CH₂C(O)NMe₂) | — No Sch # |
| 29B | (piperidine-piperidinone-CH₂C(O)NHMe) | 700 (M + 1) |
| 29C | (piperidine-piperidinone-CH₂C(O)NH₂) | 686 (M + 1) |
| 29D | (piperidine-piperidinone) | 629 (M + 1) |

Treat the crude product from Example 7, Step 1, (1.65 g) with CH₃NH₂ according to a procedure similar to Example 7, Step 2, to give the desired product (0. 6 g). MS(FAB): m/e 464.

Treat the product from Step 1 with the appropriate carboxylic acid according to a procedure similar to Example 8 to give the following compounds:

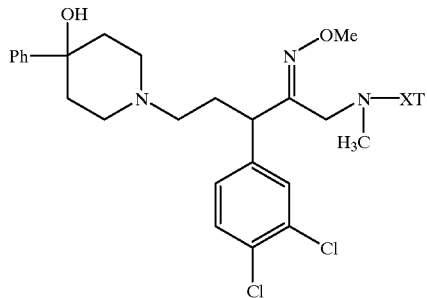

| Example | Carboxylic Acid | XT | MS (FAB): m/e |
|---|---|---|---|
| 30A | 2-chloro-6-methyl-isonicotinic acid | 2-chloro-6-methyl-pyridin-4-yl carbonyl | 617 (M + 1) |
| 30B | 2,6-dimethyl-isonicotinic acid | 2,6-dimethyl-pyridin-4-yl carbonyl | 597 (M + 1) |
| 30C | 2,6-dichloro-isonicotinic acid | 2,6-dichloro-pyridin-4-yl carbonyl | 637 (M + 1) |
| 30D | 2-dimethylamino-6-methyl-isonicotinic acid | 2-dimethylamino-6-methyl-pyridin-4-yl carbonyl | 626 (M + 1) |
| 30E | 2-chloro-6-methoxy-isonicotinic acid | 2-chloro-6-methoxy-pyridin-4-yl carbonyl | 633 (M + 1) |

-continued
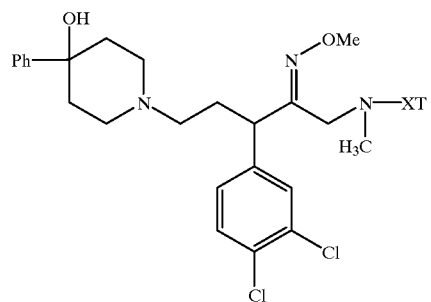
| Example | Carboxylic Acid | XT | MS (FAB): m/e |
|---|---|---|---|
| 30F | | | 658 (M + 1) |
| 30G | | | 628 (M + 1) |
| 30H | | | 596 (M + 1) |
| 30I | | | 600 (M + 1) |

EXAMPLE 31

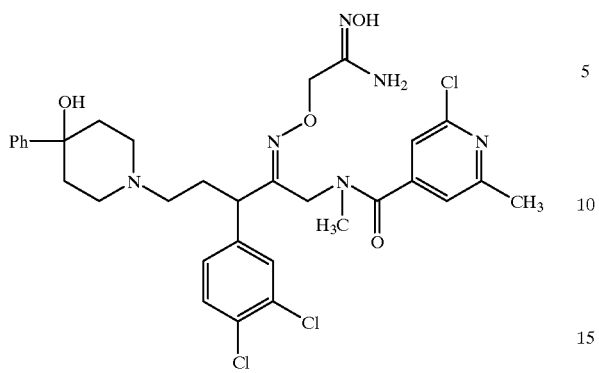

Step 1: Treat the product of Preparation 7 according to a procedure similar to that described in Example 6, Step 8. Proceed in a similar manner as described in Example 9, Steps 8–9, using 4-phenyl-4-hydroxypiperidine in place of 4-phenylamino-piperidine.
Step 2: Treat the product of Step 1 using a procedure similar to Example 5, Step 4.
Step 3: Treat the product of Step 2 in a similar procedure to that of Preparation 2, Step 4.
Step 4: Treat the product of Step 3 (8.4 g) with 2-chloro-6-methylpyridine-4-carboxylic acid (3.84 g), according to a procedure similar to Example 8 to give product (5.9 g).
Step 5: Treat the product of Step 4 (3.65 g) with $BrCH_2CN$ (0.725 g) according to a procedure similar to Example 2A to give the product (1.9 g). Step 6: Treat the product of Step 5, (1.8 g) using a procedure similar to Example 4, to give the title compound (1.31 g). MS(FAB): m/e 675 (M+1).

EXAMPLE 32

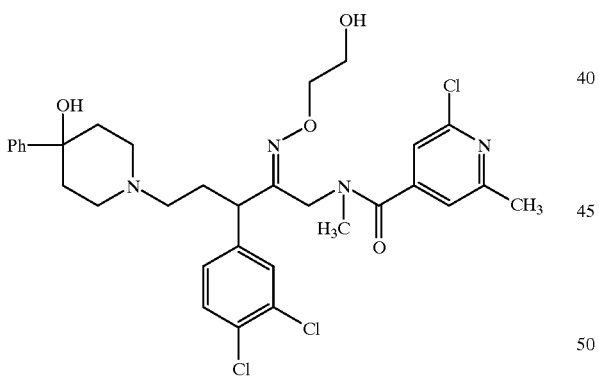

Alkylate and deprotect the product of Example 31, Step 4, using a procedure similar to Example 2B, to give the product. MS(FAB): m/e 647 (M+1).

EXAMPLE 33

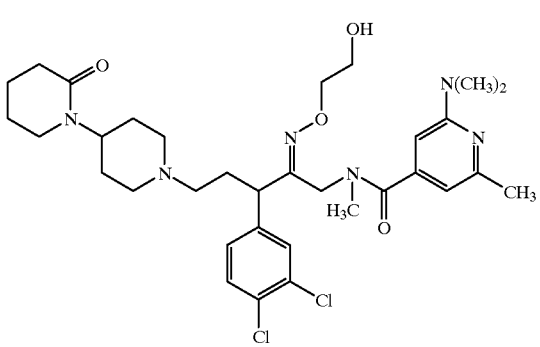

The title compound is prepared in a similar manner to the procedures of Example 32 by substituting 2-chloro-6-methylpyridine-4-carboxylic acid with 2-(dimethylamino)-6-methylpynidine4-carboxylic acid and the product of Preparation 3O6 for 4-hydroxy4-phenyl piperidine. MS(FAB): m/e 661 (M+1).

EXAMPLE 34

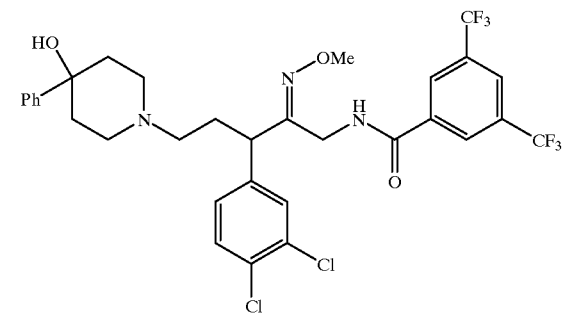

Treat the crude product from Example 7, Step 1, according to a procedure similar to Example 30, substituting $NH_4OAc$ for $MeNH_2$ in Step 1 and using 3,5-bis(trifluoromethyl)benzoic acid in Step 2 to give the title compound. MS(FAB): m/e 690.

EXAMPLE 35

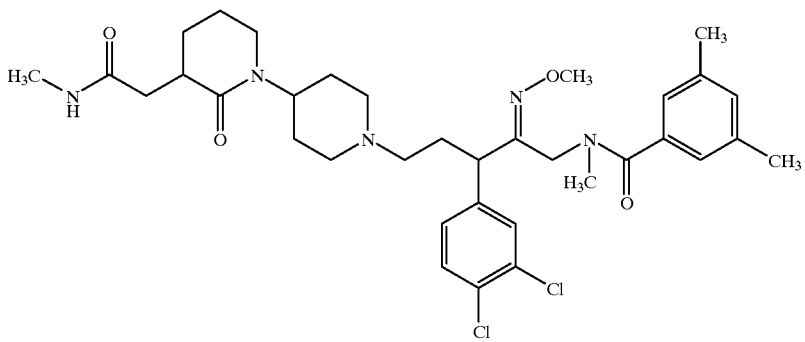

Use a procedure similar to that described in Example 18B using the product of Preparation 5B in place of the product of Preparation 3O6 to obtain the title compound. HRMS (FAB): m/e 672 (M+1).

EXAMPLE 36

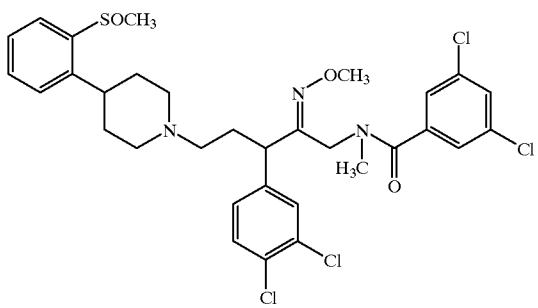

Step 1: 4-Piperidone hydrochloride (50 g) in saturated NaHCO$_3$ solution (1 L) was treated with a dioxane (30 mL) solution of benzyloxycarbonyl-chloride (53.4 mL). The solution was stirred for 18 h at room temperature then extracted with EtOAc (2×500 mL). The organic fractions were combined, washed with 1 N HCl (500 mL) and brine (500 mL), dried over MgSO$_4$, filtered and evaporated to afford 1-benzyloxycarbonyl-4-piperidone (75 g).

Step 2: 2-Bromothioanisole (13.7 g) in TMF (120 mL) was cooled to −78° C. (internal temperature) and treated with n-BuLi (36.5 mL, 2.5 M hexane solution). After 10–15 min., a THF (120 mL) solution of the product of Step 1 (12.5 g), also at −78° C., was added via a cannula. The combined mixture was stirred for a further 18 h, during which time it warmed to room temperature. The solution was treated with saturated NH$_4$Cl solution (250 mL), EtOAc (250 mL) and the organic layer separated. The aqueous portion was extracted with additional EtOAc (2×250 mL). The organic extracts were combined, washed with H$_2$O (250 mL) and brine (250 mL), dried over MgSO$_4$, filtered and evaporated to give an oil. Silica gel chromatography, eluting with EtOAc/hexane mixtures, gave 1-benzyloxycarbonyl-4-hydroxy-4-(2-methylthiophenyl)piperidine (9.61 g).

Step 3: The product of Step 2 (5.1 g) in CH$_2$Cl$_2$ (50 mL) was treated sequentially with trifluoroacetic acid (8.9 mL) and triethylsilane (34.5 mL). After 18 h, the solution was treated with saturated NaHCO$_3$ (150 mL). After a further 1 h, the organic layer was separated and the aqueous extracted with CH$_2$Cl$_2$ (100 mL). The organic extracts were combined, dried over Na$_2$SO$_4$, filtered and evaporated. The crude product was purified by silica gel chromatography, eluting with EtOAc/hexane mixtures to give 1-benzyloxycarbonyl-4(2-methylthiophenyl)piperidine (3.3 g).

Step 4: The product of Step 3 (2.55 g) in CH$_2$Cl$_2$ (30 mL) was cooled to 0° C. and treated with mCPBA (60%, 2.16 g) and stirred for 1 h. The reaction mixture was treated with ice (20 g), saturated NH$_4$OH solution (20 mL) and stirred for 10 minutes. The organic layer was separated and the aqueous layer re-extracted with CH$_2$Cl$_2$ (2×30 mL). The combined organic portions were dried over MgSO$_4$, filtered and evaporated to give a gum. Silica gel chromatography, eluting with EtOAc/CH$_2$Cl$_2$ mixtures, gave 1-benzyloxycarbonyl-4-(2-methylsulfinylphenyl)piperidine (0.5 g).

Step 5: The product of Step 4 (0.5 g) was treated with trifluoroacetic acid (10 mL) and heated at reflux temperature for 45 minutes. The reaction mixture was cooled, diluted with toluene (40 mL) and evaporated. This procedure was repeated two more times. The residue was treated with CH$_2$Cl$_2$ (70 mL) and adjusted to alkaline pH via addition of NH$_4$OH solution. The organic layer was separated, dried over MgSO$_4$, filtered and evaporated to give 4-(2-methylsulfinylphenyl)piperidine (0.3 g).

Step 6: Using a procedure similar to Example 9, Step 9, the product of Step 5 is coupled to the appropriate O-methyloxime to obtain the title compound. Mass Spec (FAB) 684 (100%).

Using the procedures of Steps A through E of Example 36, starting with 3-bromothioanisole and 4-bromothioanisole, the corresponding 4-(3-methylsulfinylphenyl) piperidine and 4-(4-methylsulfinylphenyl)piperidines were obtained.

EXAMPLE 37

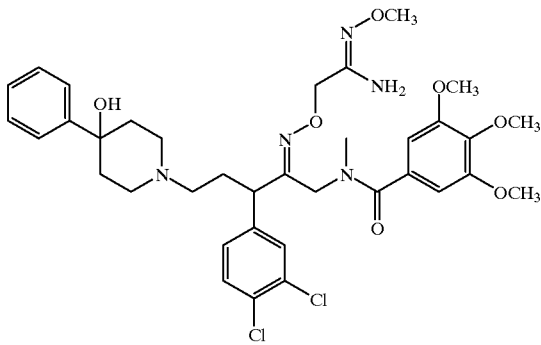

Step 1: Treat the product of Preparation 7 as described in Example 20A, acylating the amine using 3,4,5-trimethoxybenzoyl chloride.

Step 2: Treat the product of Step 1 using a procedure similar to Example 5, Step 4.

Step 3: Alkylate the product of Step 2 with BrCH$_2$CN according to a procedure similar to Example 2A.

Step 4: Treat a solution of the product of Step 3 (2.5 g) in CH$_3$OH (37 mL) with NaOCH$_3$ (200 mg). Stir for 18 h. Treat the resulting solution with CH$_3$ONH$_2$•HCl and stir for 3 h. Remove the solvent and re-suspend in CH$_2$Cl$_2$, dry over MgSO$_4$, filter, concentrate in vacuo and purify by silica gel chromatography (5×20 cm; 5% CH$_3$OH/CH$_2$Cl$_2$) to give 2.2 g of the desired product as a white foam. HRMS (FAB) 730.2774 (M+H$^+$).

The following formulations exemplify some of the dosage of this invention. In each, the term "active compound" refers to a ound of formula 1.

EXAMPLE A

Tablets

| No. | Ingredient | mg/tablet | mg/tablet |
|---|---|---|---|
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
|  | Total | 300 | 700 |

Method of Manufacture

Mix Item Nos. 1 and 2 in suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weight on a suitable tablet machine.

EXAMPLE B

Capsules

| No. | Ingredient | mg/tablet | mg/tablet |
|---|---|---|---|
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
|  | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

EXAMPLE C

Sterile Powder for Injection

| Ingredient | mg/vial | mg/vial |
|---|---|---|
| Active sterile powder | 100 | 500 |

For reconstitution add sterile water for injection or bacteriostatic water for injection.

The in vitro and in vivo activity of the compounds of formula I can be determined by various procedures known in the art, such as a test for their ability to inhibit the activity of the NK$_1$ agonist Substance P, an isolated hamster trachea NK$_2$ assay, a test of the effect of NK$_1$ antagonists on Substance P-induced airway microvascular leakage, measurement of NK$_2$ activity in vivo in guinea pigs, measurement of bronchoconstriction due to NKA, and neurokinin receptor binding assay(s). Typical procedures are described in WO96/34857, published Nov. 7, 1996. NK$_3$ activity is determined by following a procedure similar to that described in the literature, e.g., *Molecular Pharmacol.*, 48 (1995), p. 711–716.

% Inhibition is the difference between the percent of maximum specific binding (MSB) and 100%. The percent of MSB is defined by the following equation, wherein "dpm" is disintegrations per minute:

$$\% \ MSB = \frac{(dpm \ \text{of unknown}) - (dpm \ \text{of nonspecific binding})}{(dpm \ \text{of total binding}) - (dpm \ \text{of nonspecific binding})} \times 100$$

It will be recognized that compounds of formula I exhibit NK$_1$, NK$_2$ and/or NK$_3$ antagonist activity to varying degrees, e.g., certain compounds have strong NK$_1$ antagonist activity, but weaker NK$_2$ and NK$_3$ antagonist activity, while others are strong NK$_2$ antagonists, but weaker NK$_1$ and NK$_3$ antagonists. While compounds with approximate equipotency are preferred, it is also within the scope of this invention to use compounds of with unequal NK$_1$/NK$_2$/NK$_3$ antagonist activity when clinically appropriate.

Preferred compounds of the invention have a Ki≦10 nM for the NK$_1$ receptor. Also preferred are compounds of formula I having a Ki≦10 nM for the NK$_2$ receptor. Also preferred are compounds having a Ki≦10 nM for each of the NK$_1$ and NK$_2$ receptors. More preferred are compounds having a Ki≦2 nM for the NK$_1$ receptor and a Ki ≦2 nM for the NK$_2$ receptor. Compounds of the invention tested for NK$_3$ have Ki's in the range of 0.05 to 50 nM. The compound of Example 11, the only amide specifically disclosed in U.S. Pat. No. 5,696,267, has a Ki of 3.6 for the NK$_1$ receptor and a Ki of 9.2 for the NK$_2$ receptor.

Using the test procedures described above, the following data (Ki) were obtained for exemplified compounds:

| Ex. | Ki (NK$_1$) (nM) | Ki (NK$_2$) (nM) |
|---|---|---|
| 12E | 0.4 | 0.2 |
| 12F | 0.6 | 0.8 |
| 12K | 0.9 | 0.5 |
| 12L | 0.5 | 0.9 |
| 13A | 0.8 | 0.2 |

-continued
| Ex. | Ki (NK$_1$) (nM) | Ki (NK$_2$) (nM) |
| --- | --- | --- |
| 13B | 0.9 | 0.3 |
| 13C | 0.4 | 0.2 |
| 13D | 1.1 | 0.7 |
| 13E | 0.4 | 0.6 |
| 13F | 0.2 | 0.3 |
| 13G | 1.5 | 0.4 |
| 13H | 2.6 | 0.4 |
| 14B | 0.3 | 0.8 |
| 14D | 0.3 | 0.2 |
| 14E | 0.2 | 0.4 |
| 15A | 0.2 | 0.7 |
| 15B | 1.7 | 0.8 |
| 15D | 0.4 | 0.5 |
| 15E | 0.50 | 1.0 |
| 15F | 0.4 | 0.8 |
| 15G | 0.9 | 1.3 |
| 15H | 0.2 | 0.4 |
| 15I | 0.8 | 1.0 |
| 15J | 0.7 | 4.3 |
| 15K | 0.5 | 0.2 |
| 15L | 1.0 | 1.4 |
| 15M | 0.2 | 0.3 |
| 16A | 0.2 | 0.7 |
| 17A | 0.5 | 3.0 |
| 17E | 0.7 | 0.7 |
| 17K | 3.3 | 2.7 |
| 17S | 0.8 | 0.8 |
| 18B | 0.8 | 0.4 |
| 18D | 0.4 | 0.4 |
| 18E | 0.4 | 0.4 |
| 18J | 0.3 | 3.4 |
| 18M | 0.2 | 0.4 |
| 19C | 0.2 | 0.2 |
| 19D | 0.9 | 1.4 |
| 19E | 0.6 | 1.8 |
| 21B | 6 | 0.5 |
| 23 | 0.8 | 0.5 |
| 25 | 0.9 | 0.7 |
| 26 | 1.0 | 1.3 |
| 27 | 0.7 | 1.2 |
| 28B | 0.8 | 1.0 |
| 28C | 0.4 | 0.6 |
| 29B | 5.2 | 1.3 |
| 29C | 2.6 | 0.7 |
| 30A | 1.4 | 1.9 |
| 31 | 0.4 | 1.8 |
| 35 | 0.6 | 0.3 |
| 36 | 0.8 | 1.0 |
| 37 | 0.7 | 0.7 |
We claim:
1. A compound selected from the group consisting of
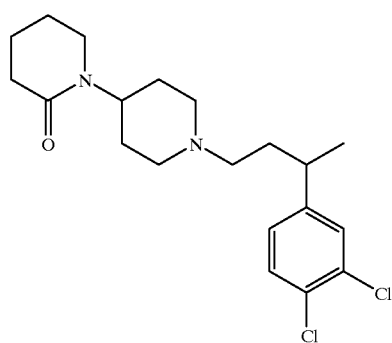
-continued
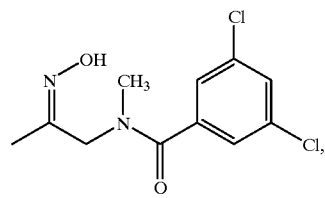
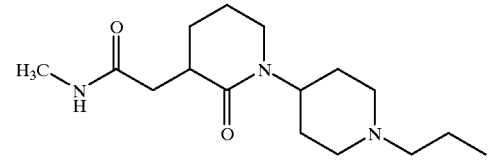
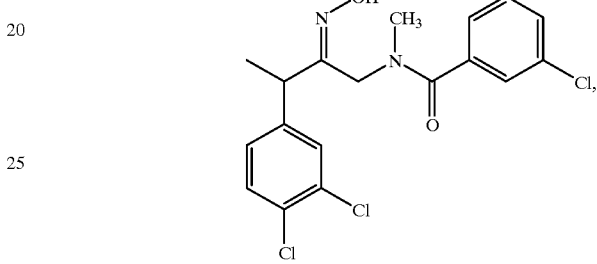
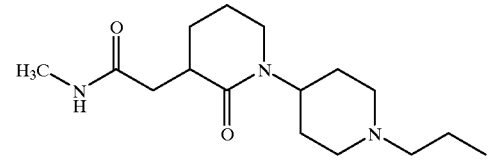
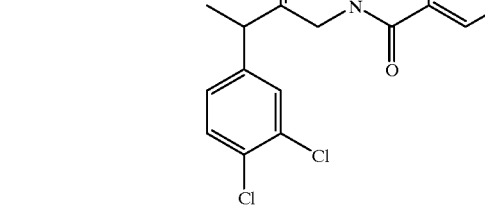
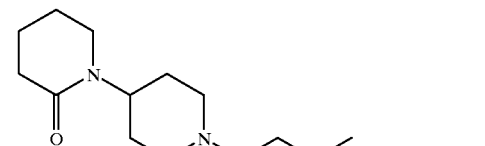
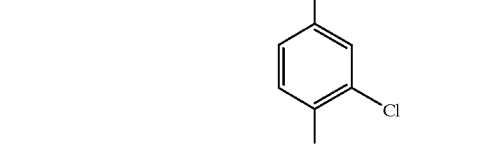

91
-continued
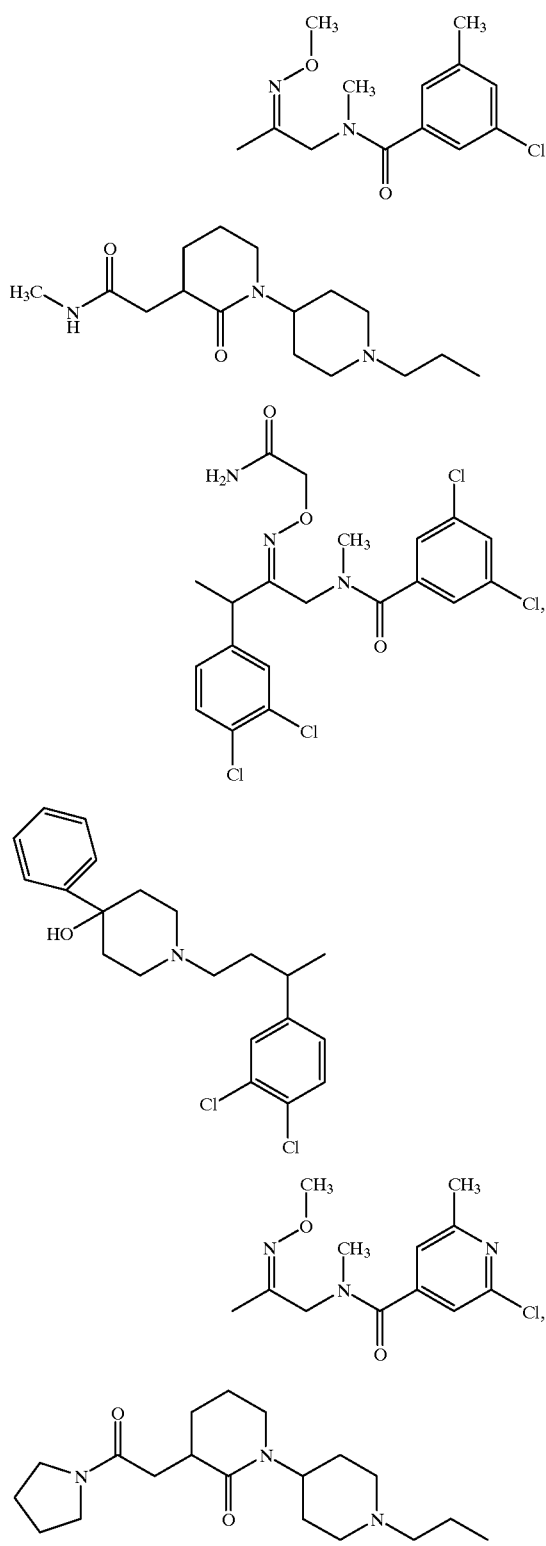
92
-continued
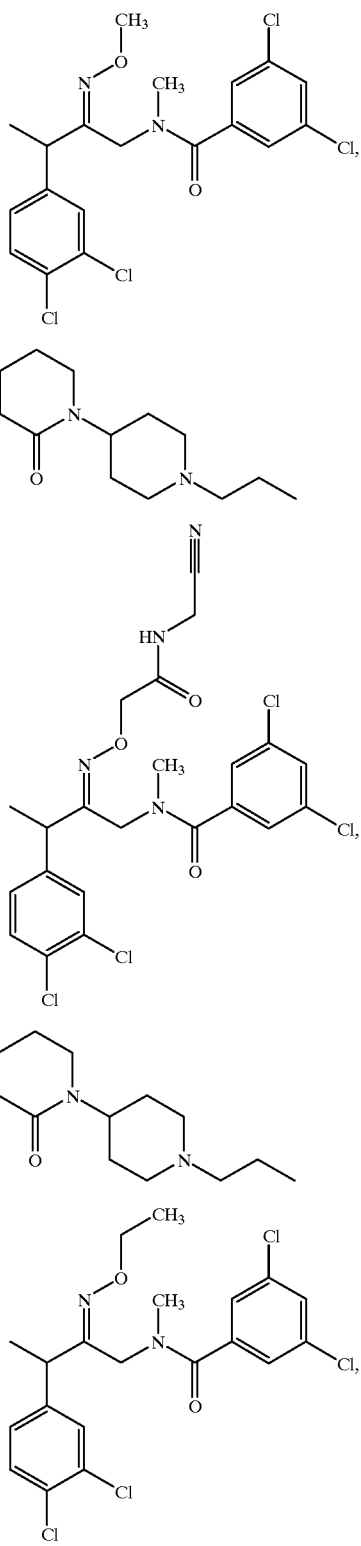

93
-continued
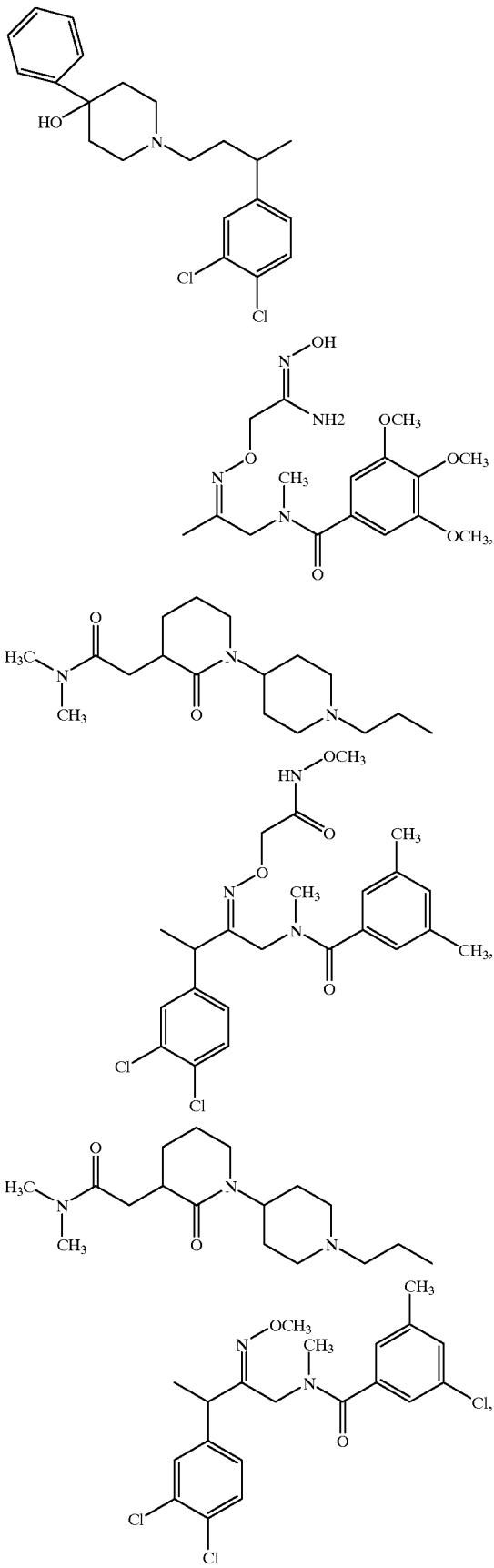
94
-continued
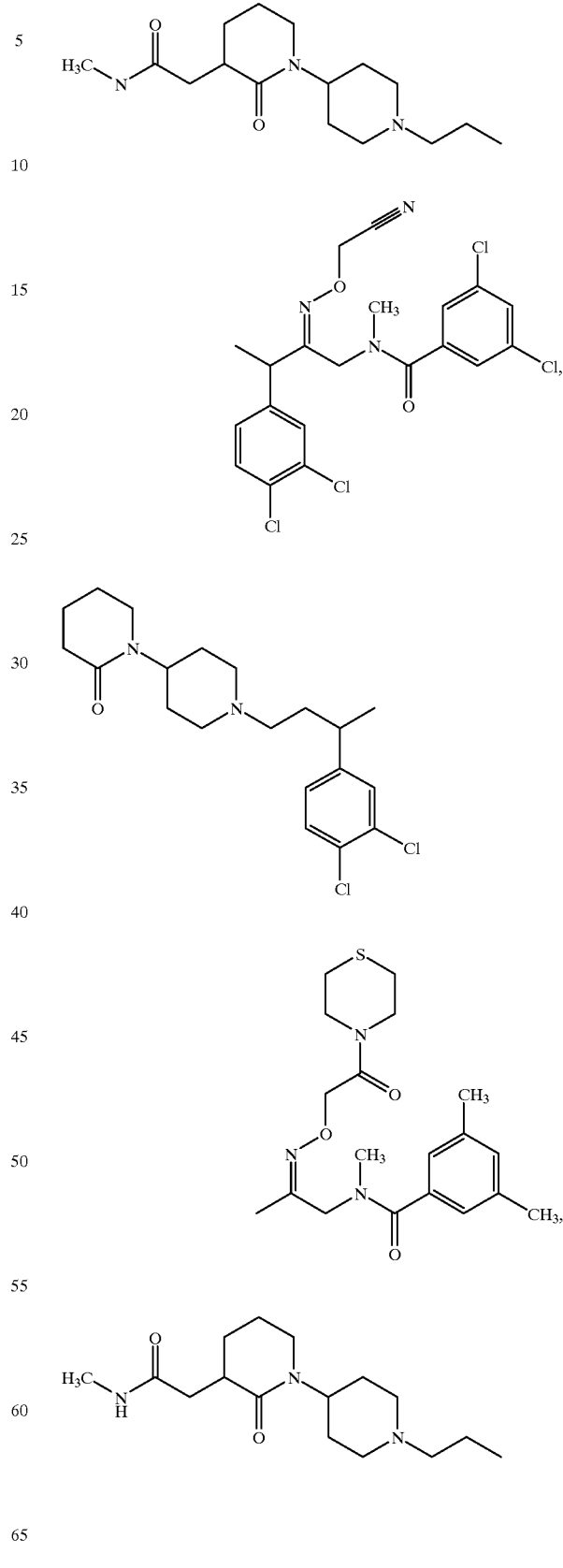

95
-continued
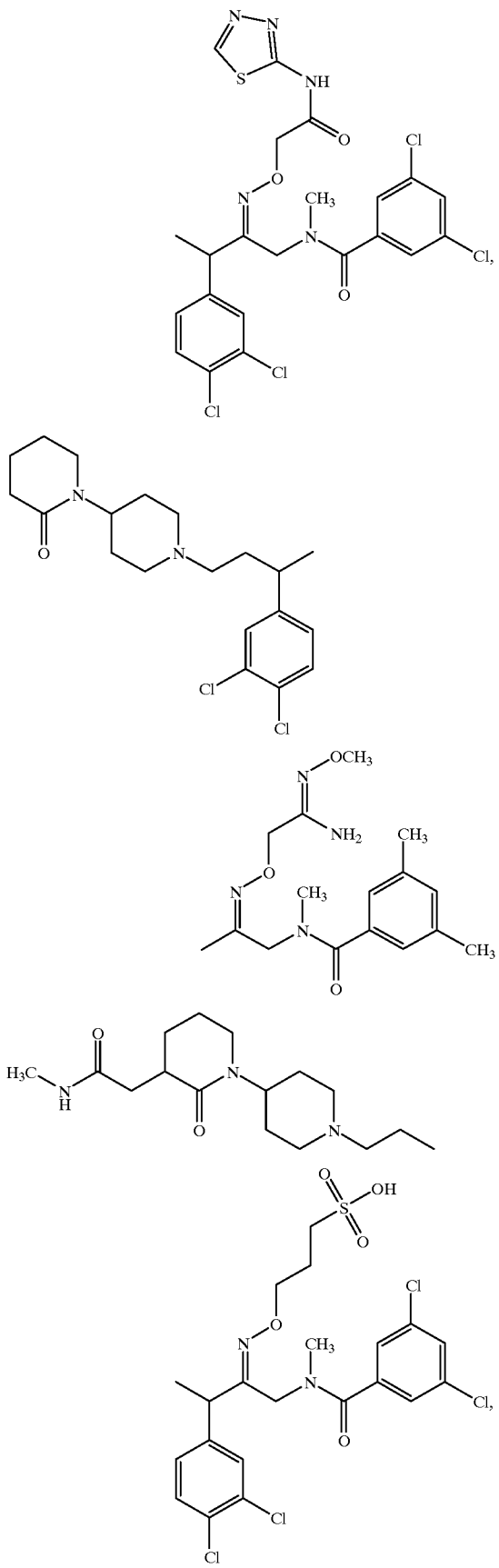
96
-continued
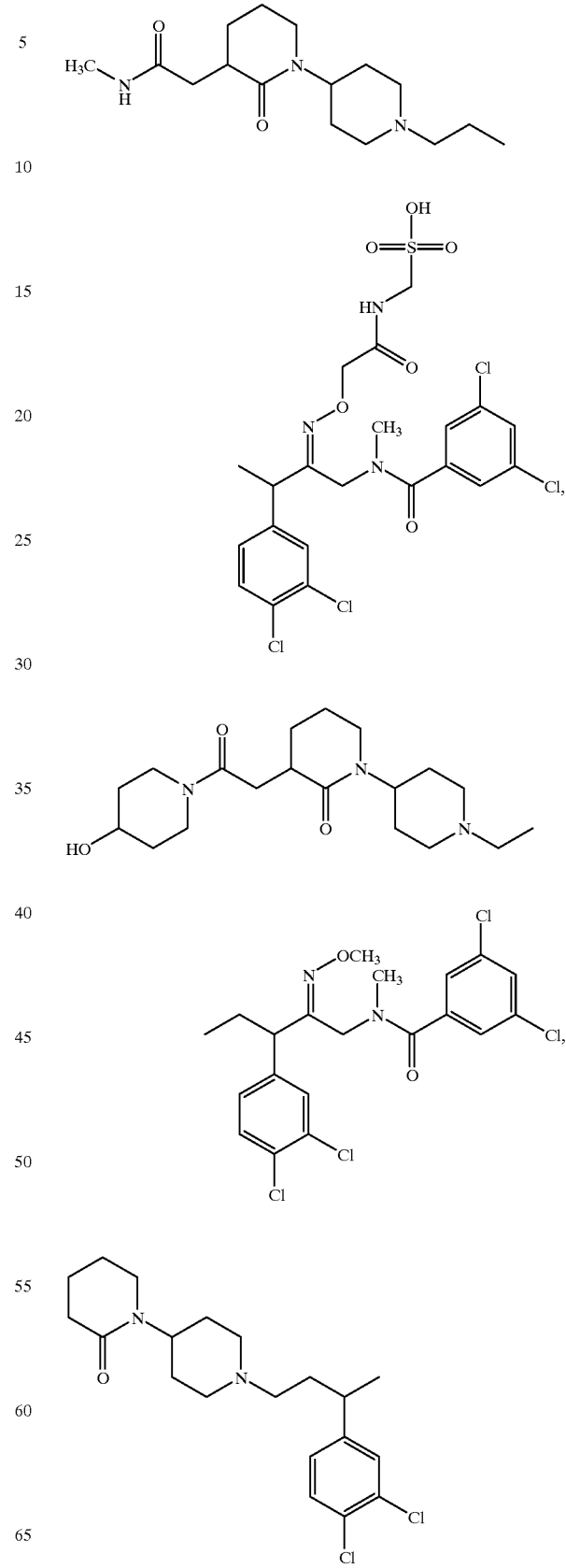

97
-continued
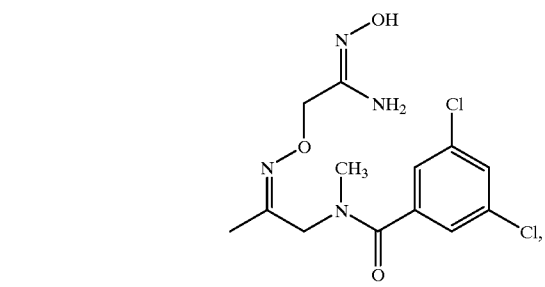
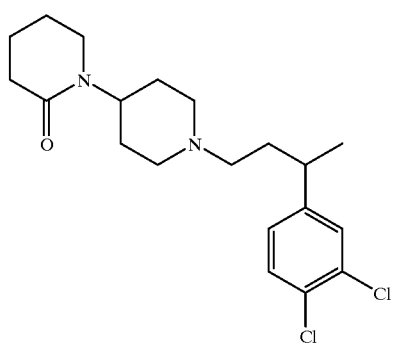
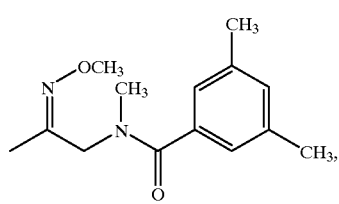
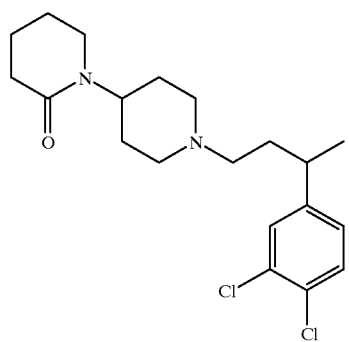
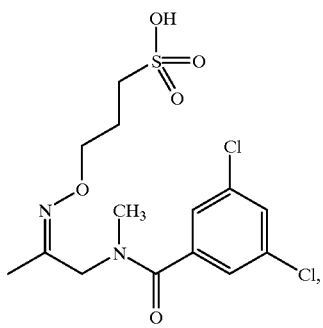
98
-continued
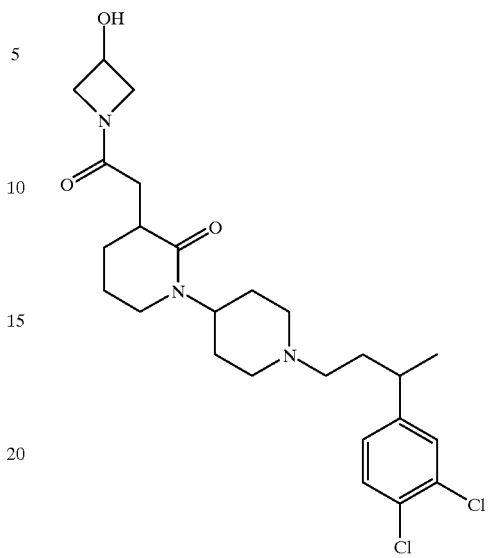
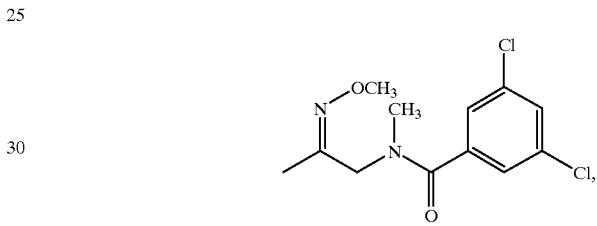
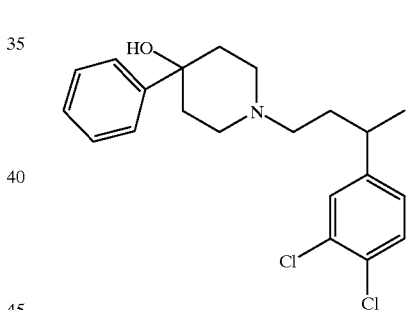
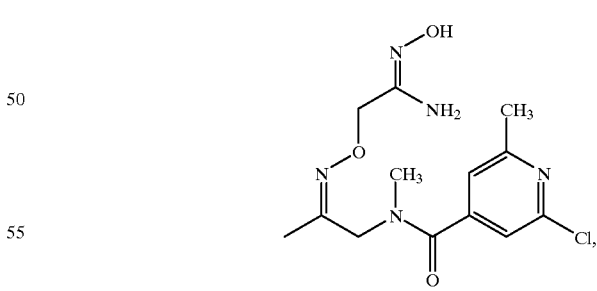
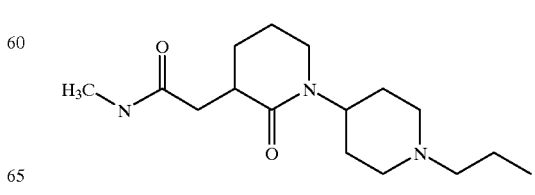

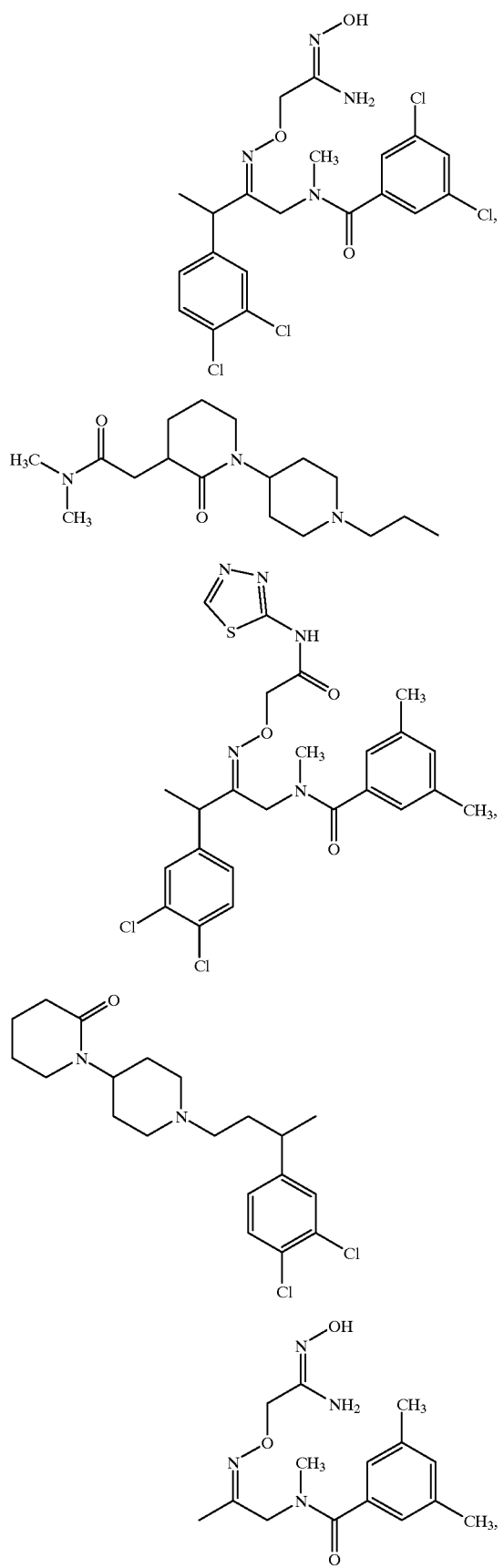
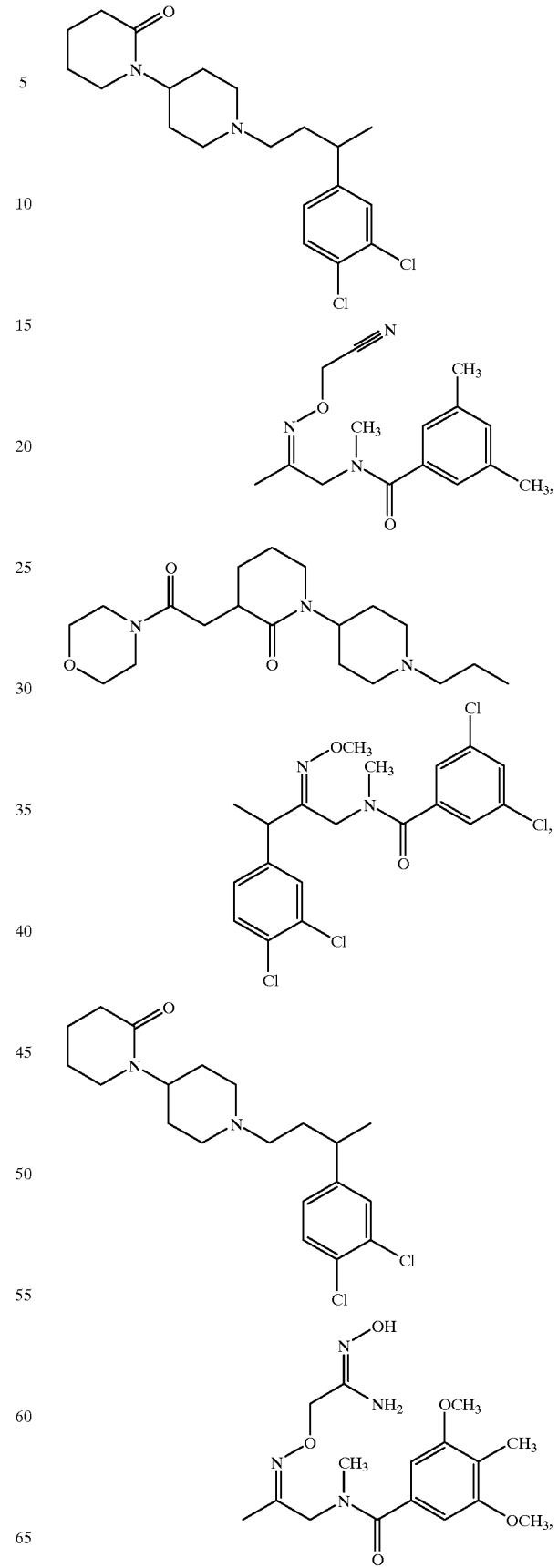

101
-continued
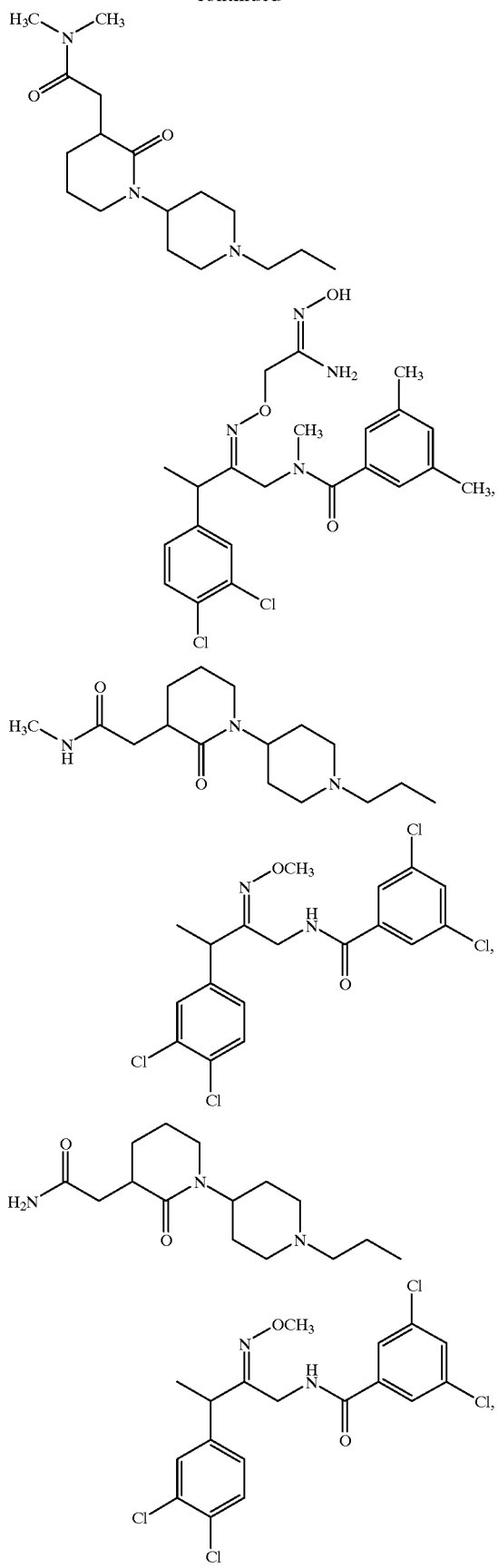
102
-continued
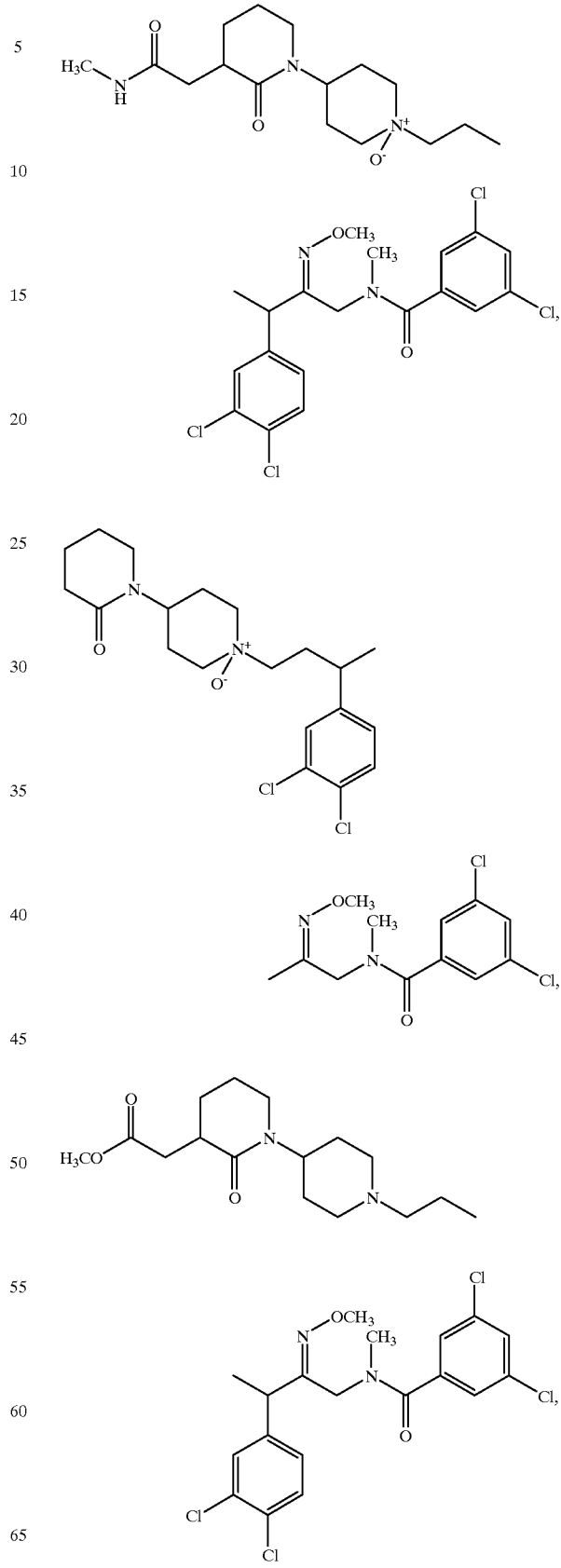

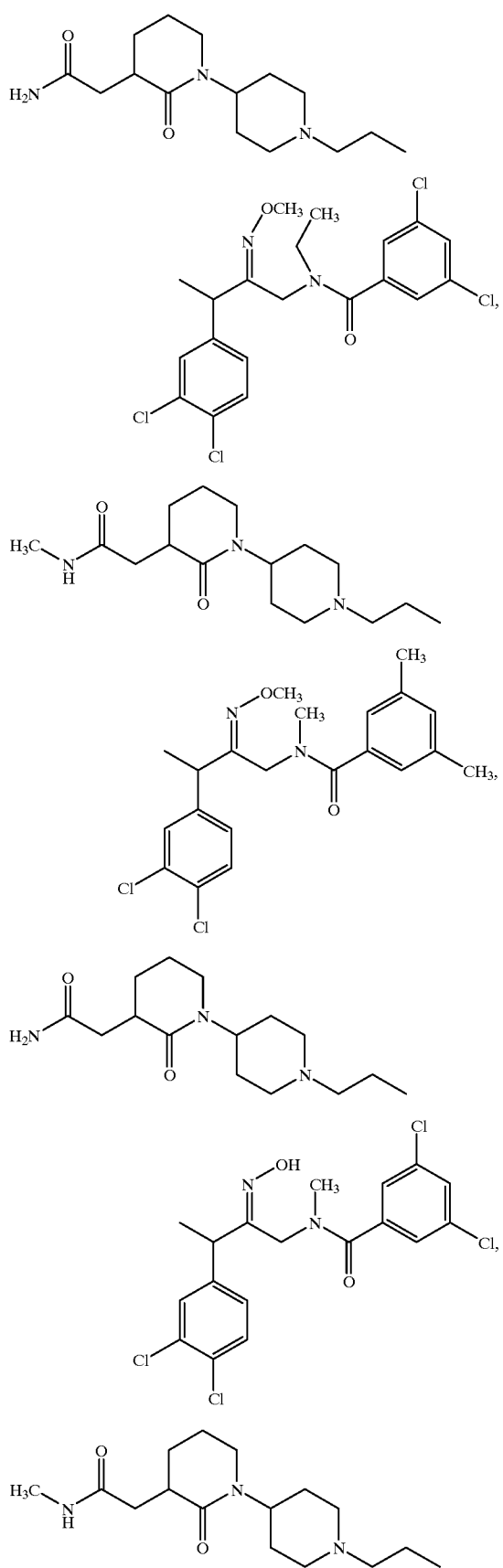
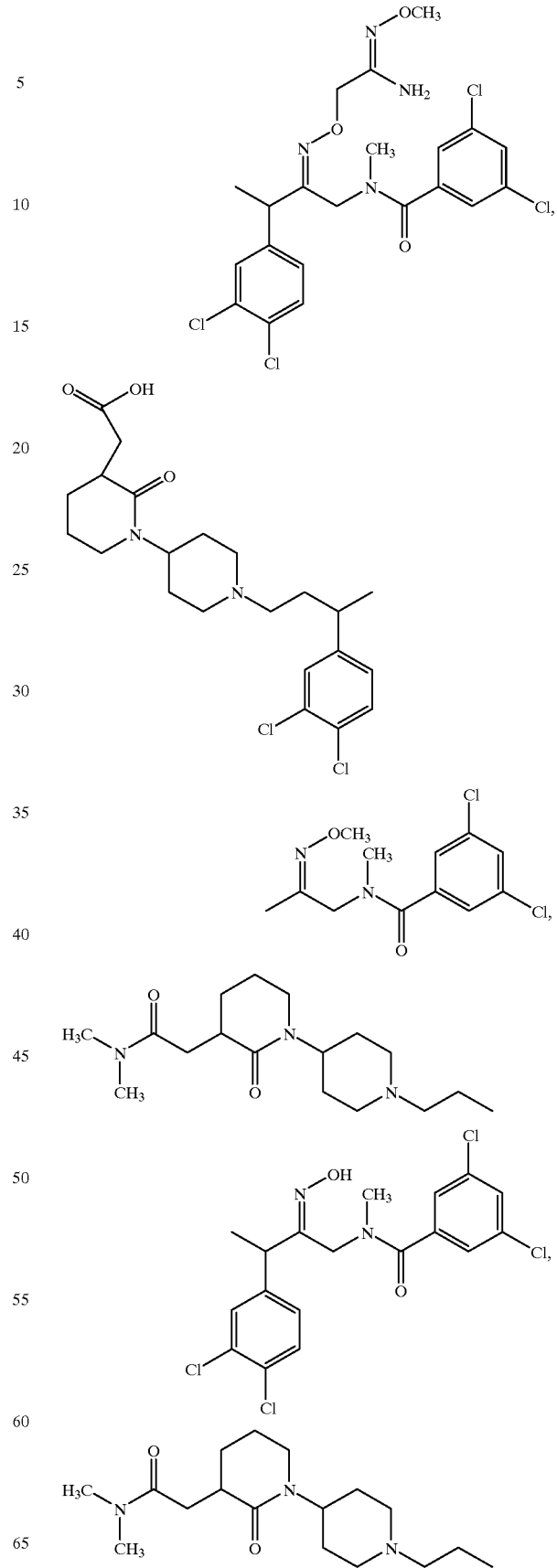

105
-continued
106
-continued
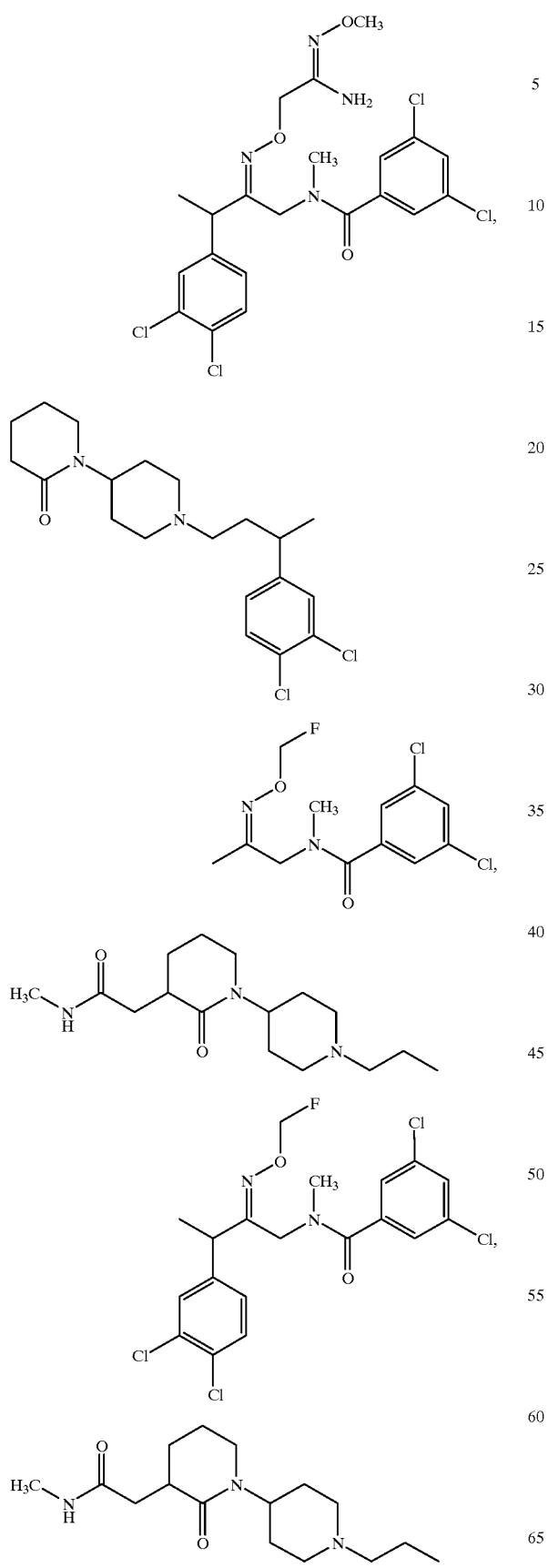

107
-continued
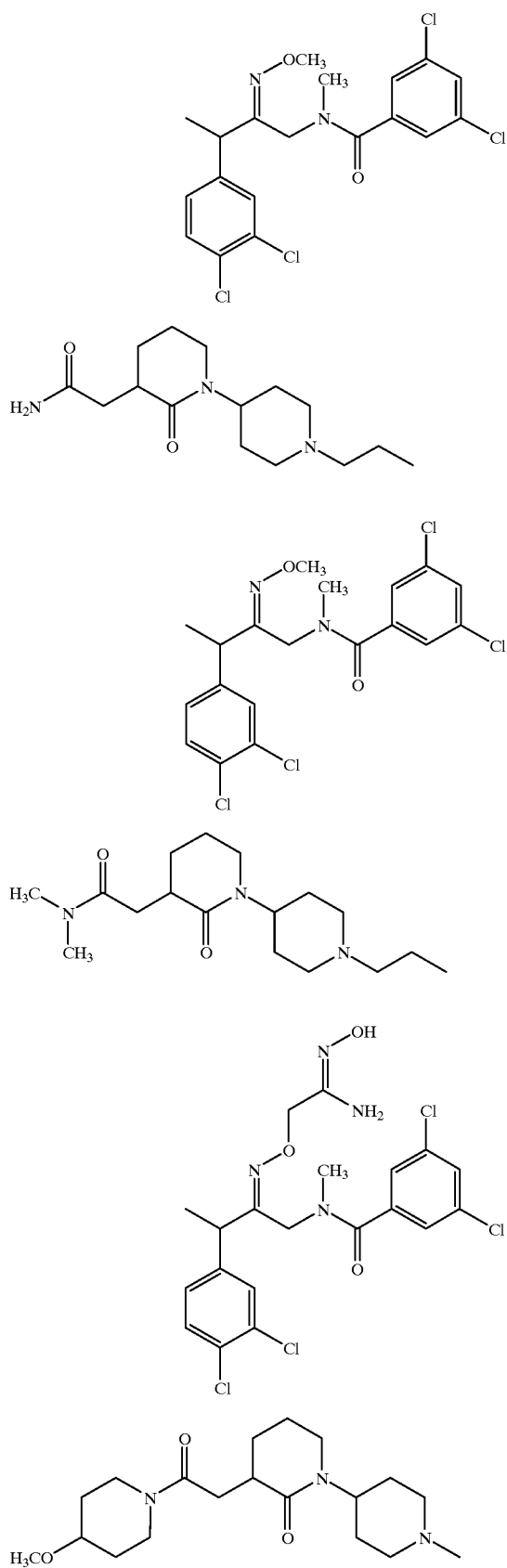
108
-continued
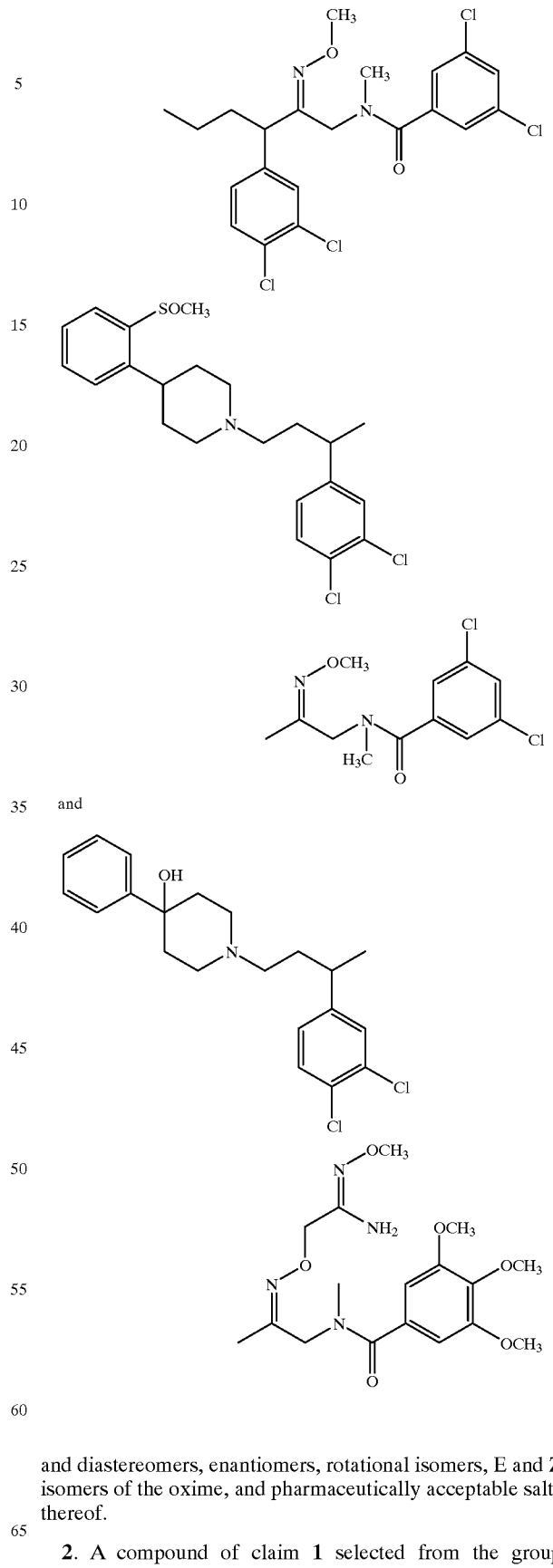
and diastereomers, enantiomers, rotational isomers, E and Z isomers of the oxime, and pharmaceutically acceptable salts thereof.
2. A compound of claim 1 selected from the group consisting of

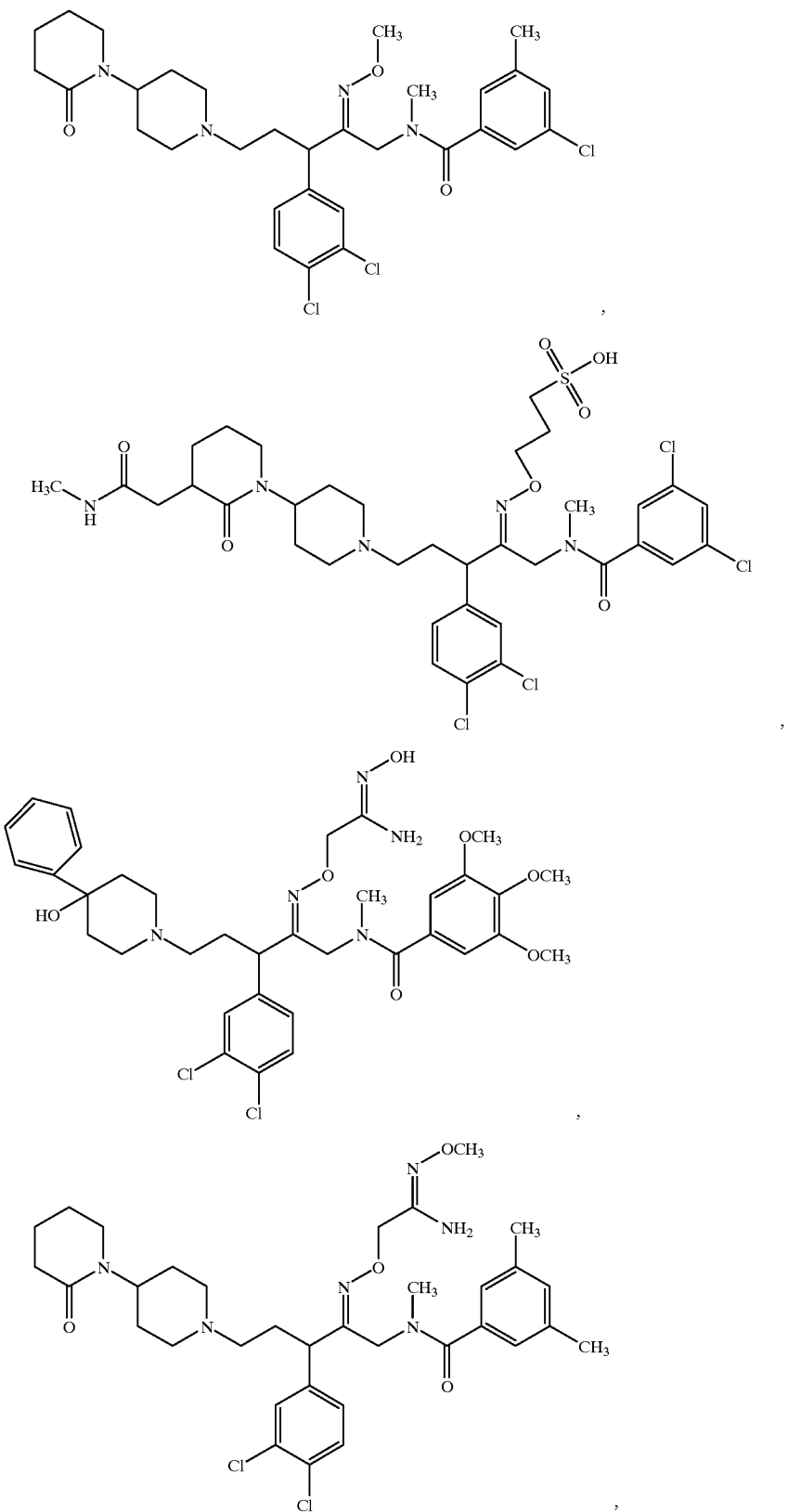

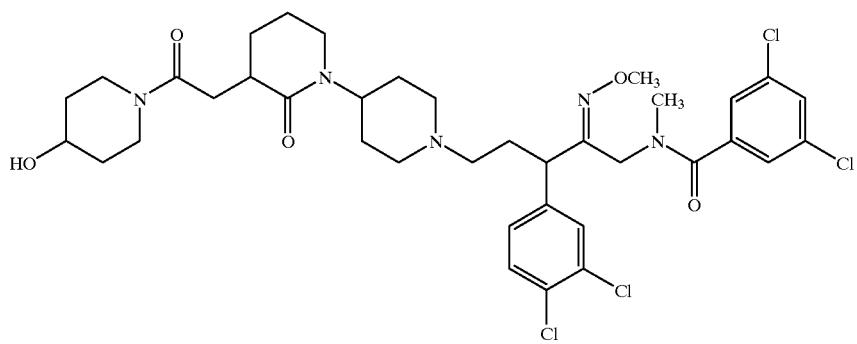
,
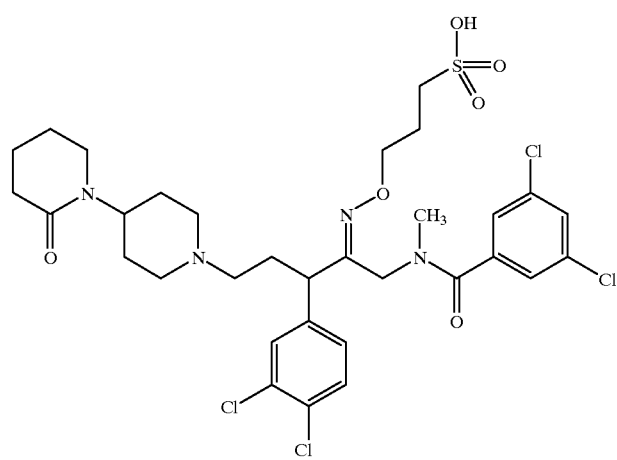
,
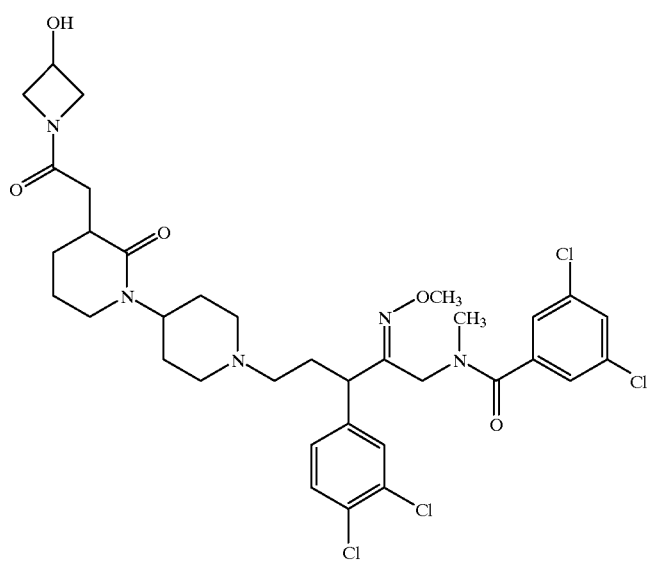
,

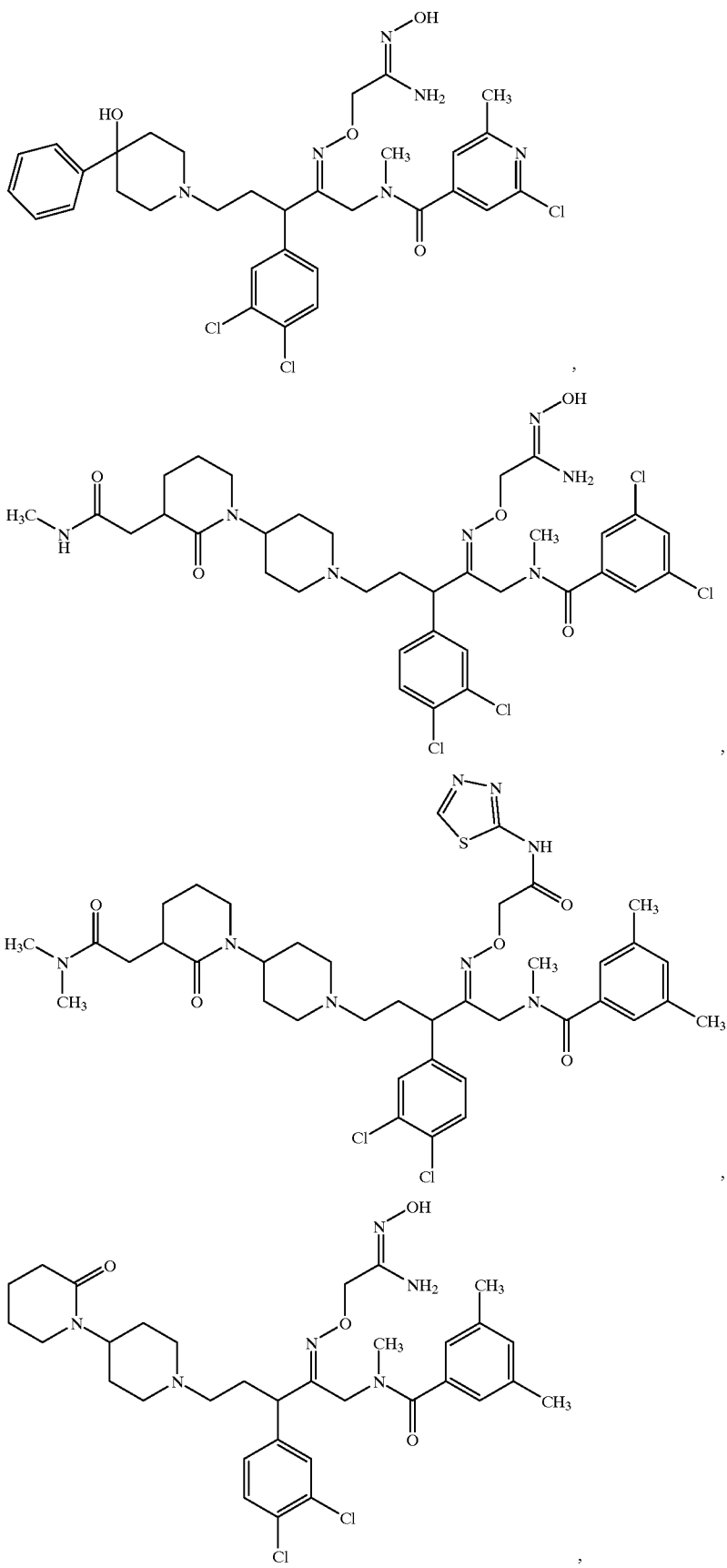

-continued
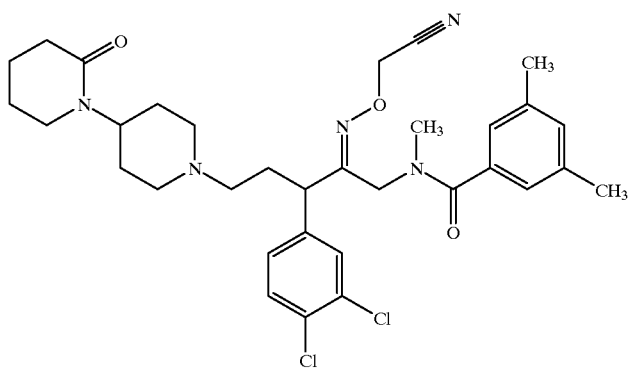
,
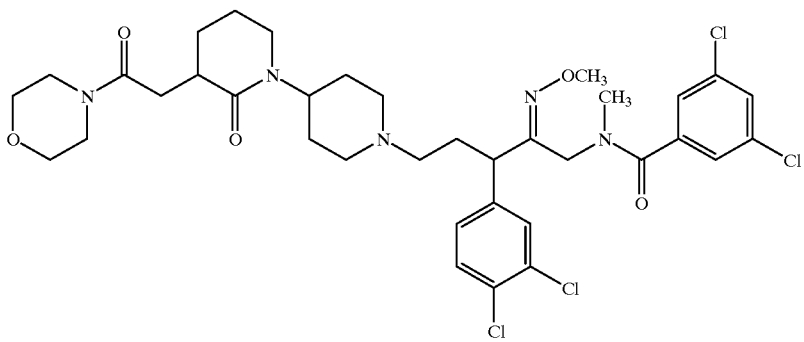
,
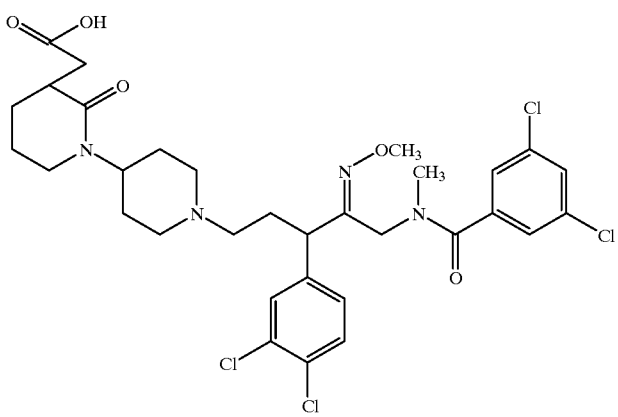
,
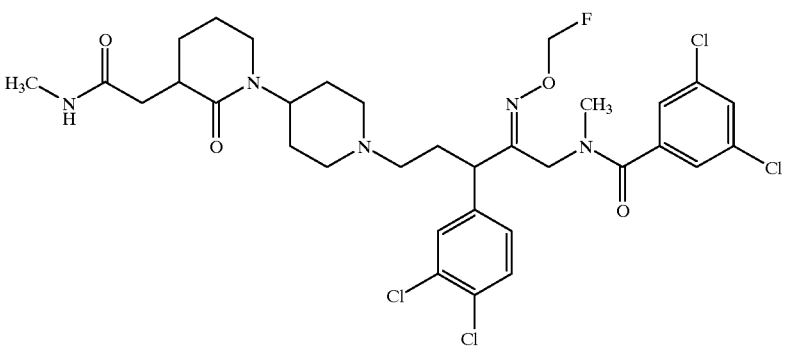
,

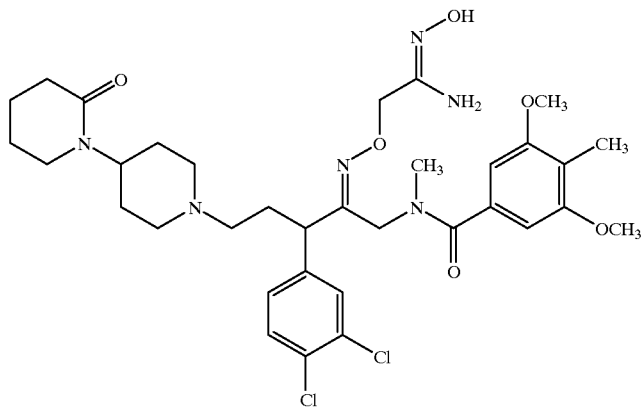,
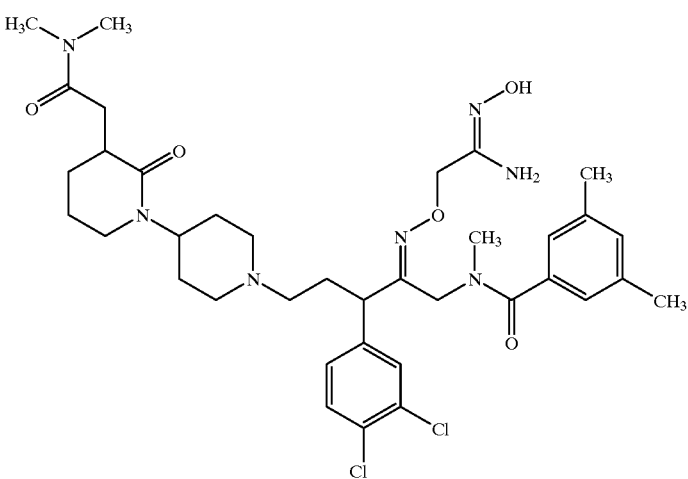,
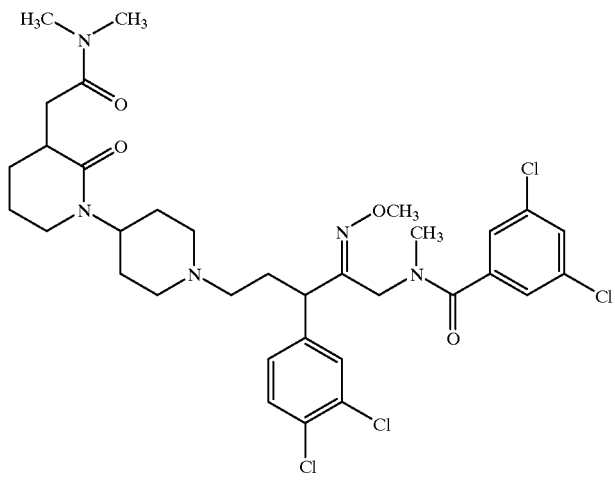,
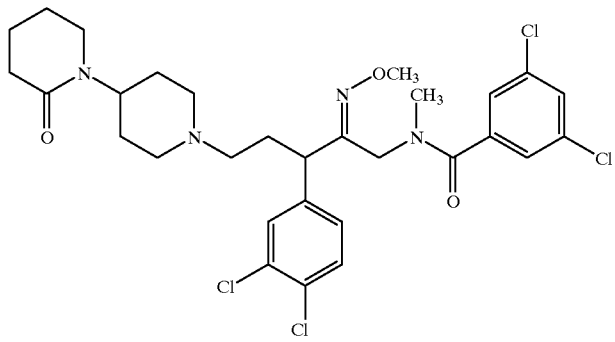,

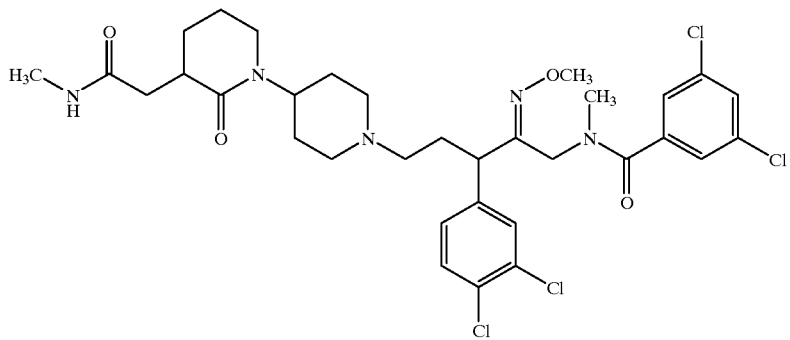
,
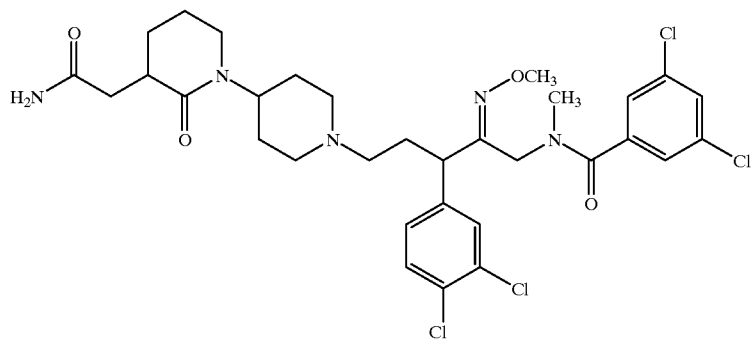
,
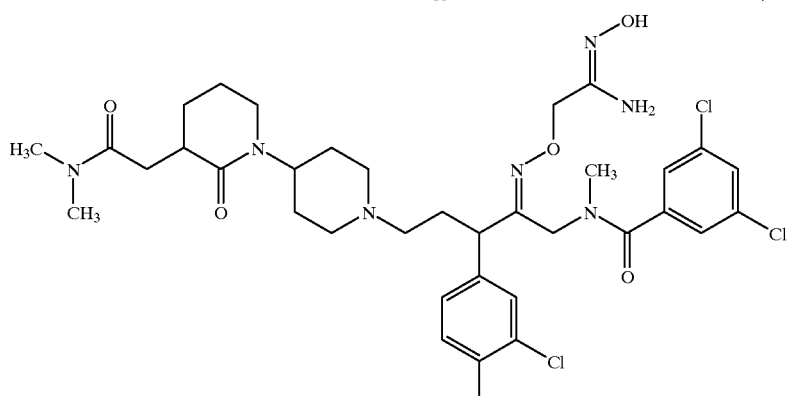
and
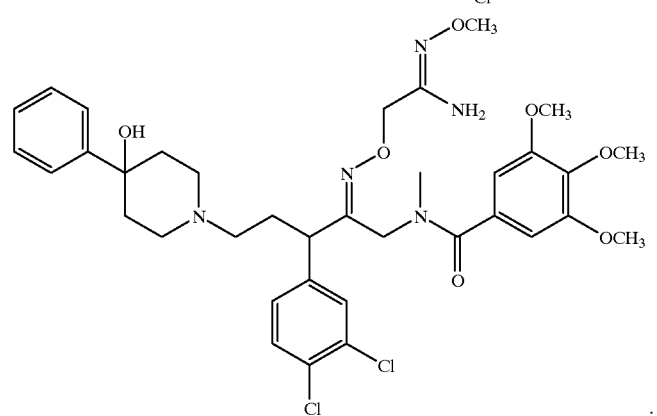
.

3. A compound of claim 2 selected from the group consisting of
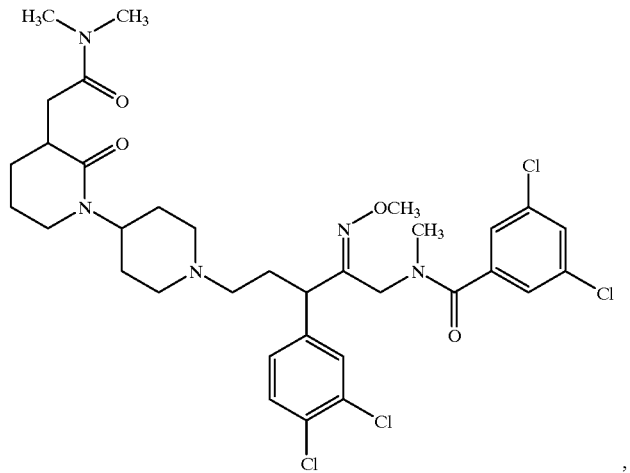
,
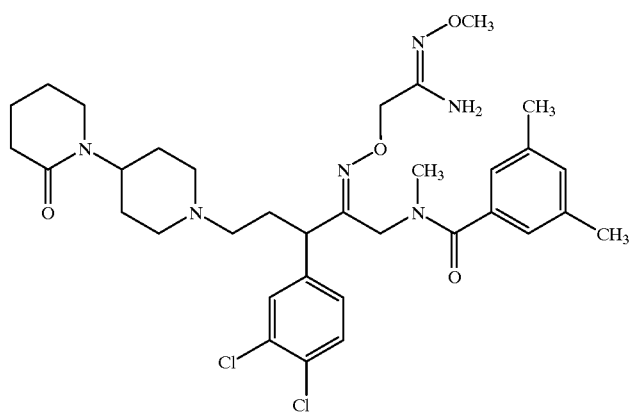
,
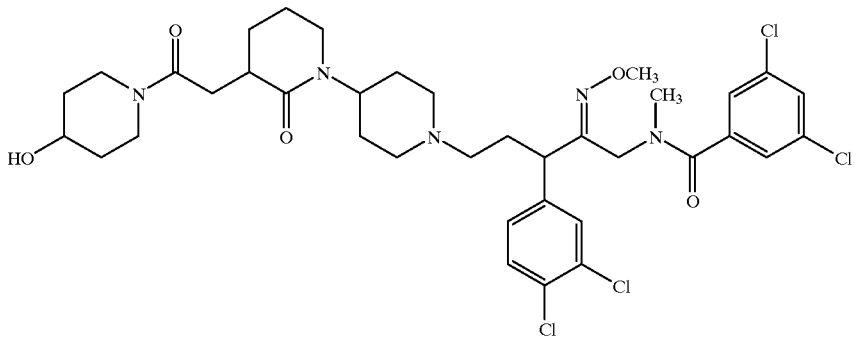
,
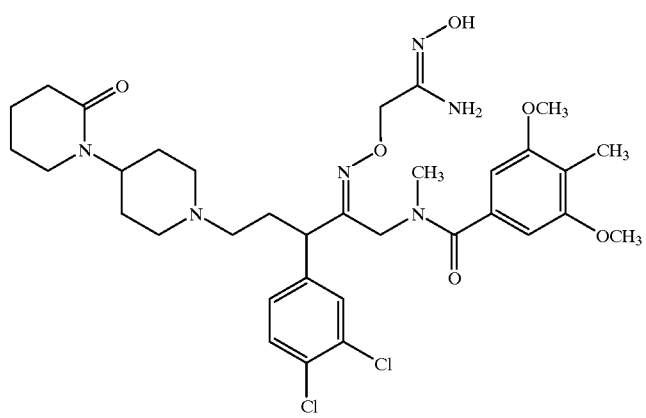
,

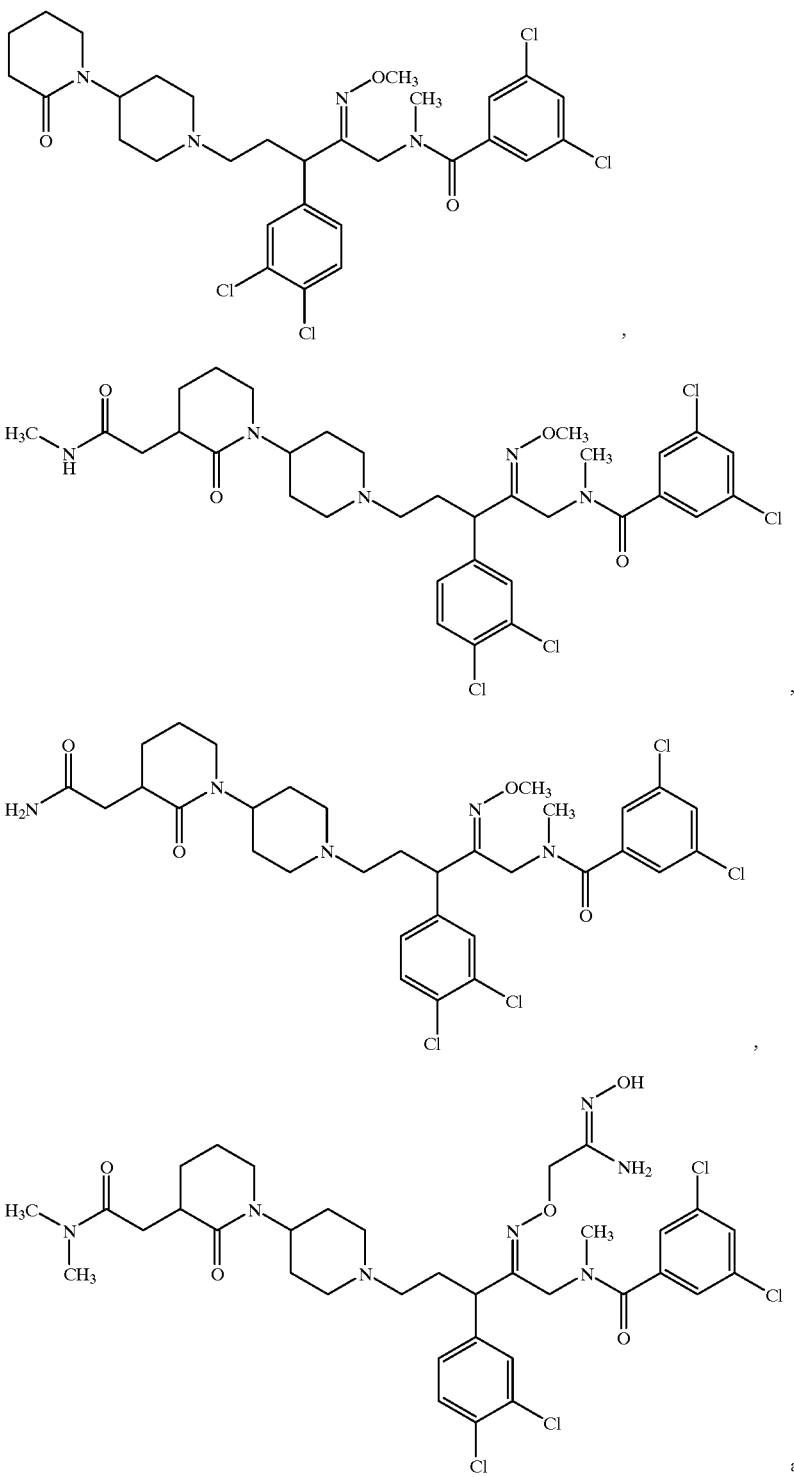

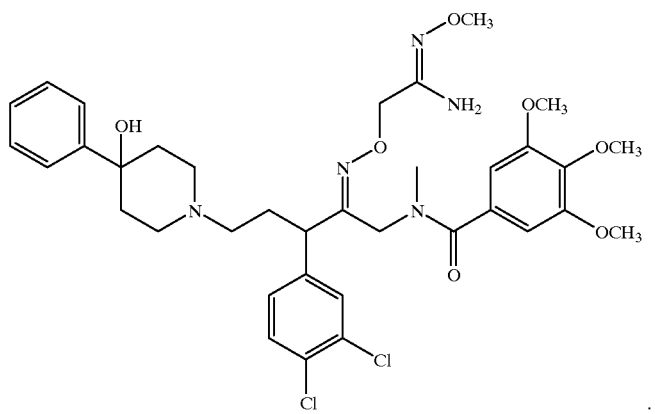
4. A compound of claim 1 which is
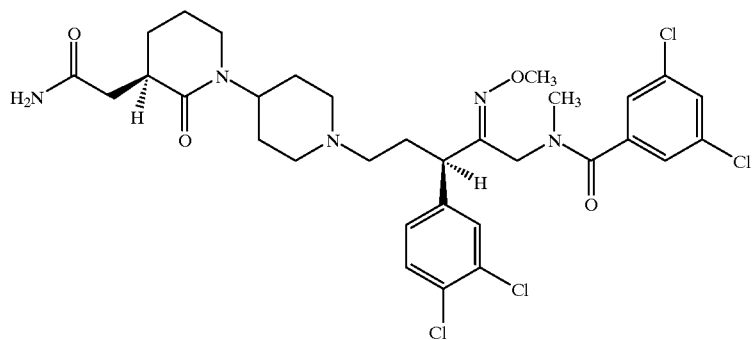
or
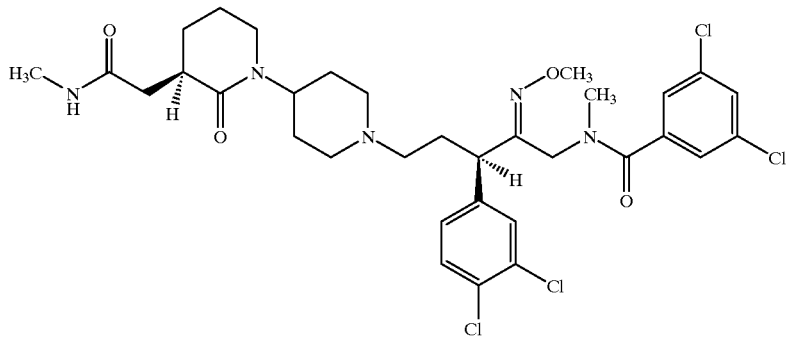
, or a diastereomer, enantiomer, rotational isomer, E and Z isomer of the oxime, or pharmaceutically acceptable salt thereof.

5. A compound represented by the formula

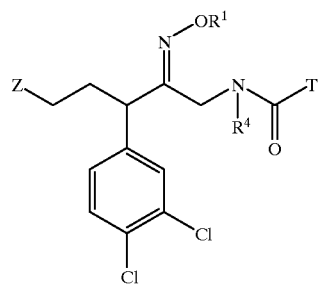

or a diastereomer, enantiomer, rotational isomer or E or Z isomer of the oxime, or a pharmaceutically acceptable salt, thereof, wherein:

T is $R^2$-phenyl or $R^3$-pyridyl;

$R^1$ is H, methyl, ethyl, —$CH_2CN$, —$CH_2C(O)NH_2$, —$(CH_2)_3SO_3H$, —$CH_2C(O)NHCH_3$, —$CH_2C(O)NHOH$, —$CH_2C(O)NHOCH_3$, —$CH_2C(O)NHCH_2CN$, —$CH_2F$, —$CH_2C(O)NHCH_2SO_3H$,

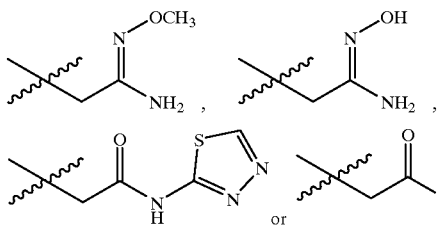

$R^2$ is 2–3 substituents independently selected from the group consisting of chloro, methyl and methoxy;

$R^3$ is 2 to 3 substituents independently selected from the group consisting of chloro and methyl;

$R^4$ is methyl or ethyl; and

Z is

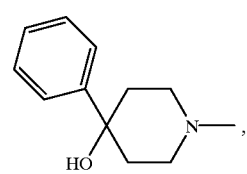

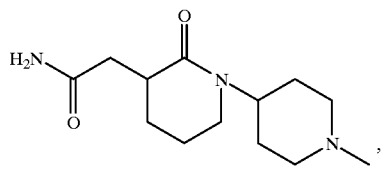

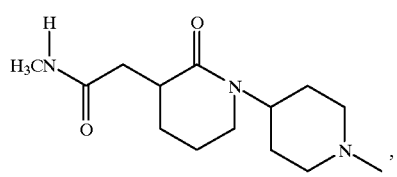

-continued

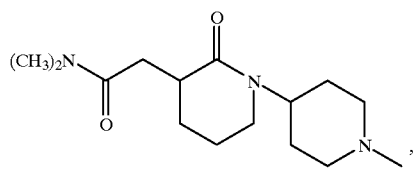

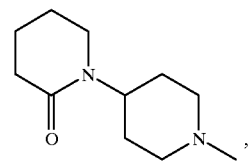

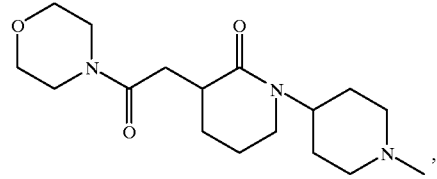

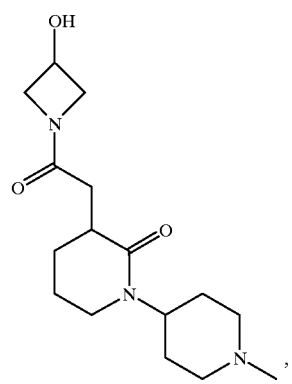

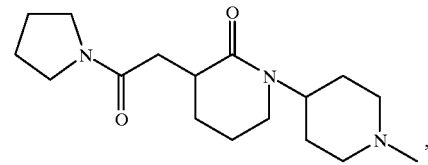

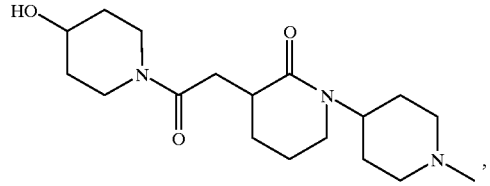

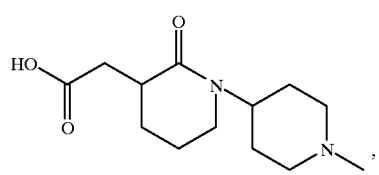

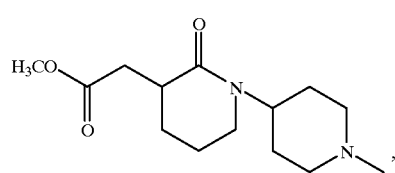

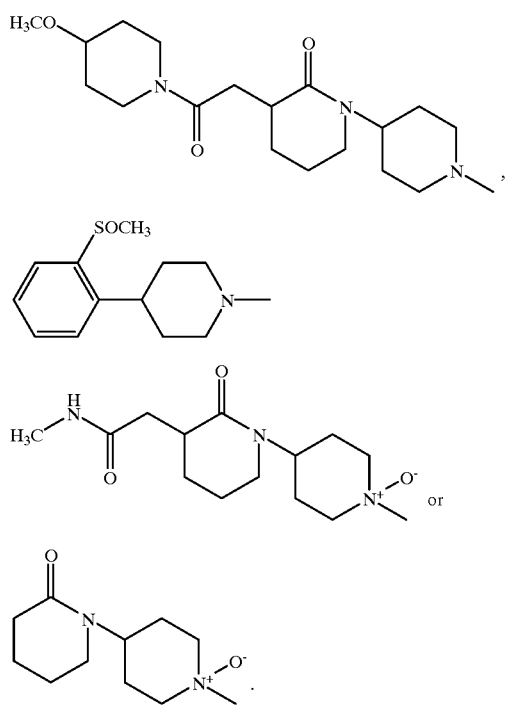
6. A compound of claim 5 wherein T is $R^2$-substituted phenyl, wherein $R^2$ is two chloro substituents, two methyl substituents or two methoxy and one methyl substituent; $R^1$ is methyl, —CH$_2$F, —CH$_2$CN,
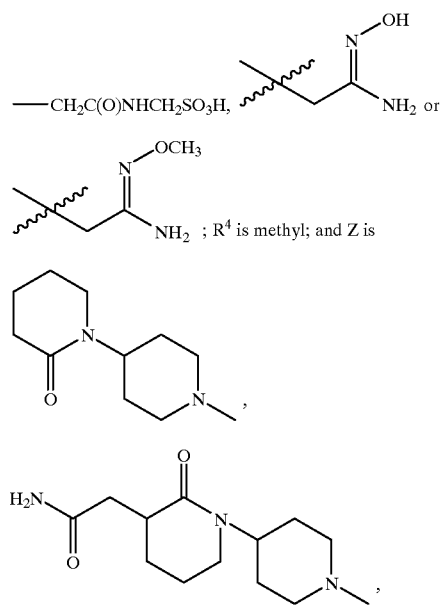
$R^4$ is methyl; and Z is
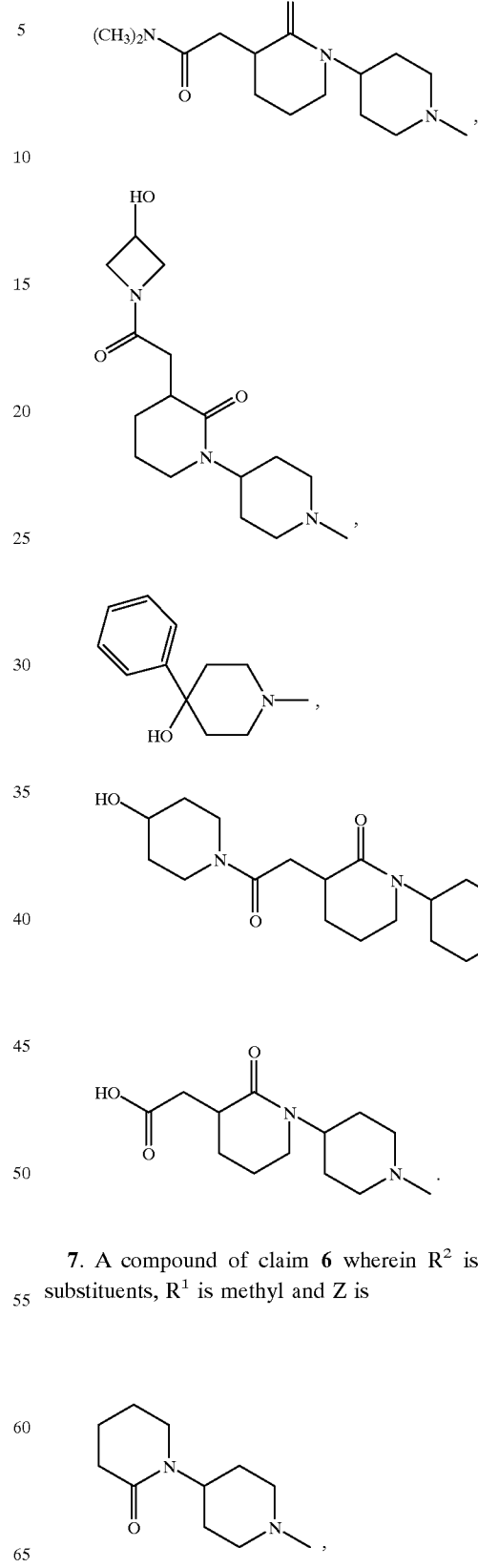
7. A compound of claim 6 wherein $R^2$ is two chloro substituents, $R^1$ is methyl and Z is -continued
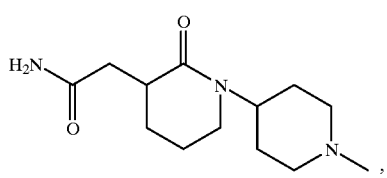
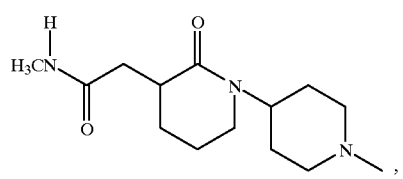
-continued
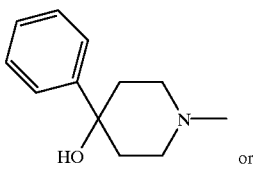
or
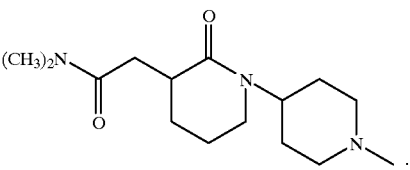
\* \* \* \* \*